US012691182B2

(12) United States Patent
Nittoli et al.

(10) Patent No.: US 12,691,182 B2
(45) Date of Patent: * Jul. 28, 2026

(54) MAYTANSINOID DERIVATIVES, CONJUGATES THEREOF, AND METHODS OF USE

(71) Applicant: Regeneron Pharmaceuticals, Inc., Tarrytown, NY (US)

(72) Inventors: Thomas Nittoli, Pearl River, NY (US); Thomas P. Markotan, Newtown, PA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 410 days.

This patent is subject to a terminal disclaimer.

(21) Appl. No.: 17/889,301

(22) Filed: Aug. 16, 2022

(65) Prior Publication Data

US 2023/0116771 A1 Apr. 13, 2023

Related U.S. Application Data

(63) Continuation of application No. 16/663,251, filed on Oct. 24, 2019, now Pat. No. 11,446,389, which is a continuation of application No. 15/907,142, filed on Feb. 27, 2018, now Pat. No. 10,463,749, which is a continuation of application No. 15/414,537, filed on Jan. 24, 2017, now Pat. No. 9,950,076.

(60) Provisional application No. 62/286,858, filed on Jan. 25, 2016.

(51) Int. Cl.
| | |
|---|---|
| *C07D 498/18* | (2006.01) |
| *A61K 31/537* | (2006.01) |
| *A61K 47/68* | (2017.01) |
| *C07K 16/32* | (2006.01) |
| *C07K 16/40* | (2006.01) |

(52) U.S. Cl.
CPC ........ *A61K 47/6851* (2017.08); *A61K 31/537* (2013.01); *A61K 47/68* (2017.08); *C07D 498/18* (2013.01); *C07K 16/32* (2013.01); *C07K 16/40* (2013.01)

(58) Field of Classification Search
None
See application file for complete search history.

(56) References Cited

U.S. PATENT DOCUMENTS

| | | | |
|---|---|---|---|
| 4,260,608 A | 4/1981 | Miyashita et al. | |
| 4,263,294 A * | 4/1981 | Miyashita | C07D 498/18 |
| | | | 540/462 |
| 4,361,650 A | 11/1982 | Asai et al. | |
| 5,208,020 A | 5/1993 | Chari et al. | |
| 5,714,586 A | 2/1998 | Kunstmann et al. | |
| 6,596,541 B2 | 7/2003 | Murphy et al. | |
| 7,595,292 B2 | 9/2009 | Brocchini et al. | |
| 7,750,116 B1 | 7/2010 | Doronina et al. | |
| 7,939,630 B2 | 5/2011 | Brocchini et al. | |
| 8,816,051 B2 | 8/2014 | Brocchini et al. | |
| 8,877,706 B2 | 11/2014 | Li et al. | |
| 8,889,855 B2 | 11/2014 | Deng | |
| 9,005,598 B2 | 4/2015 | Godwin et al. | |
| 9,950,076 B2 | 4/2018 | Nittoli et al. | |
| 9,951,141 B2 | 4/2018 | Nittoli et al. | |
| 10,463,749 B2 | 11/2019 | Nittoli et al. | |
| 10,570,151 B2 | 2/2020 | Nittoli | |
| 10,772,972 B2 | 9/2020 | Rudge et al. | |
| 11,446,389 B2 * | 9/2022 | Nittoli ................. | C07D 498/18 |
| 2004/0235840 A1 | 11/2004 | Chari et al. | |
| 2005/0169933 A1 | 8/2005 | Steeves et al. | |
| 2007/0258987 A1 | 11/2007 | Francisco et al. | |
| 2008/0171040 A1 | 7/2008 | Ebens et al. | |
| 2008/0305044 A1 | 12/2008 | McDonagh et al. | |
| 2008/0305497 A1 | 12/2008 | Kosmeder et al. | |
| 2009/0068178 A1 | 3/2009 | Crowley et al. | |
| 2009/0280056 A1 | 11/2009 | Dennis et al. | |
| 2010/0129314 A1 | 5/2010 | Singh et al. | |
| 2011/0250133 A1 | 10/2011 | Lattuada et al. | |
| 2012/0058892 A1 | 3/2012 | Braun et al. | |
| 2012/0096572 A1 | 4/2012 | Macdonald et al. | |
| 2012/0276124 A1 | 11/2012 | Bouchard et al. | |
| 2013/0029900 A1 | 1/2013 | Widdison | |
| 2013/0039900 A1 | 2/2013 | Sunahara et al. | |
| 2013/0101546 A1 | 4/2013 | Yurkovetskiy et al. | |
| 2014/0178415 A1 | 6/2014 | Li et al. | |
| 2014/0179917 A1 | 6/2014 | Deng | |
| 2014/0363454 A1 | 12/2014 | Jackson et al. | |
| 2014/0369960 A1 | 12/2014 | Brocchini et al. | |
| 2015/0056222 A1 | 2/2015 | Papadopoulos et al. | |
| 2015/0125473 A1 | 5/2015 | Burt et al. | |

(Continued)

FOREIGN PATENT DOCUMENTS

| | | |
|---|---|---|
| CN | 103 254 311 A | 8/2013 |
| EP | 0 425 235 A2 | 5/1991 |

(Continued)

OTHER PUBLICATIONS

Lowe, Derek; "Not alphafold's fault", Blog "In the Pipeline," entry of Sep. 7, 2022.

(Continued)

*Primary Examiner* — Noble E Jarrell

(74) *Attorney, Agent, or Firm* — FisherBroyles, LLP; Cara L. Crowley-Weber; Liang Zeng Yan

(57) ABSTRACT

Provided herein are maytansinoid compounds, derivatives thereof, conjugates thereof, and methods of treating or preventing proliferative diseases with the same.

18 Claims, 18 Drawing Sheets

(56) References Cited

U.S. PATENT DOCUMENTS

| | | |
|---|---|---|
| 2015/0157736 A1 | 6/2015 | Rabuka et al. |
| 2015/0216994 A1 | 8/2015 | Godwin et al. |
| 2015/0283259 A1 | 10/2015 | Buet et al. |
| 2016/0058882 A1 | 3/2016 | Chari et al. |
| 2016/0354482 A1 | 12/2016 | Nittoli et al. |
| 2016/0375147 A1 | 12/2016 | Nittoli |
| 2017/0121413 A1 | 5/2017 | Nittoli et al. |
| 2017/0209591 A1 | 7/2017 | Nittoli et al. |
| 2018/0289834 A1 | 10/2018 | Nittoli et al. |
| 2018/0312597 A1 | 11/2018 | Nittoli et al. |
| 2019/0151323 A1 | 5/2019 | Nittoli et al. |
| 2020/0121806 A1 | 4/2020 | Nittoli et al. |
| 2021/0087272 A1 | 3/2021 | Kuhnert et al. |

FOREIGN PATENT DOCUMENTS

| | | |
|---|---|---|
| WO | WO 02/094325 A2 | 11/2002 |
| WO | WO 2004/018000 A2 | 3/2004 |
| WO | WO 2004/103272 A2 | 12/2004 |
| WO | WO 2005/010151 A2 | 2/2005 |
| WO | WO 2005/089808 | 9/2005 |
| WO | WO 2006/062779 A2 | 6/2006 |
| WO | WO 2008/122039 | 10/2008 |
| WO | WO 2008/141044 A2 | 11/2008 |
| WO | WO 2009/117277 A2 | 9/2009 |
| WO | WO 2010/010324 | 1/2010 |
| WO | WO 2010/126551 A1 | 4/2010 |
| WO | WO 2010/124797 A1 | 11/2010 |
| WO | WO 2011/018611 | 2/2011 |
| WO | WO 2011/039724 A1 | 4/2011 |
| WO | WO 2011/130598 | 10/2011 |
| WO | WO 2012/005982 A1 | 1/2012 |
| WO | WO 2012/058592 A2 | 5/2012 |
| WO | WO 2012/061590 A1 | 5/2012 |
| WO | WO 2012/156918 A1 | 11/2012 |
| WO | WO 2012/166559 | 12/2012 |
| WO | WO 2012/177837 A2 | 12/2012 |
| WO | WO 2013/043933 A2 | 3/2013 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |
| WO | WO 2013/068874 | 5/2013 |
| WO | WO 2013/075048 A1 | 5/2013 |
| WO | WO 2013/085925 A1 | 6/2013 |
| WO | WO 2013/190272 A1 | 12/2013 |
| WO | WO 2013/190292 A2 | 12/2013 |
| WO | WO 2014/064424 A1 | 5/2014 |
| WO | WO 2014/065661 | 5/2014 |
| WO | WO 2014/080251 | 5/2014 |
| WO | WO 2014/089335 A2 | 6/2014 |
| WO | WO 2014/145090 | 9/2014 |
| WO | WO 2014/194030 | 12/2014 |
| WO | WO 2014/194030 A2 | 12/2014 |
| WO | WO 2014/197849 A2 | 12/2014 |
| WO | WO 2014/197854 | 12/2014 |
| WO | WO 2014/197866 A1 | 12/2014 |
| WO | WO 2015/031396 A1 | 3/2015 |
| WO | WO 2015/081281 A1 | 6/2015 |
| WO | WO 2015/081282 A1 | 6/2015 |
| WO | WO 2015/081857 | 6/2015 |
| WO | WO 2016/160615 | 10/2016 |

OTHER PUBLICATIONS

Reynolds, Fred et al; "A functional proteomic method for biomarker discovery." PLoS One (2011) 6(7) e22471.

Agarwal et al., "A Pictet-Spengler ligation for Protein Chemical Modification", Proc. Natl Acad. Sci., Jan. 2, 2013, vol. 110, No. 1, pp. 46-51.

Akcakanat et al., "Heterogeneous expression of GAGE, NY-ESO-1, MAGE-A and SSX proteins in esophageal cancer: Implications for immunotherapy", Int. J. Cancer, 2006, vol. 118, pp. 123-128.

Auclair et al., "Strategies for stabilizing superoxide dismutase (SOD1), the protein destabilized in the most common form of familial amyotrophic lateral sclerosis", PNAS, Dec. 14, 2010, vol. 107, No. 50, pp. 21394-21399; www.pnas.org/cgi/doi/10.1073/pnas. 1015463107.

Badescu et al., "Bridging Disulfides for Stable and Defined Antibody Drug Conjugates", Bioconjugate Chemistry, May 3, 2014, vol. 25, No. 6, pp. 1124-1136, XP055165403.

Badescu, George: Director Scientific Affairs—Bioconjugation & Protein Engineering, "Producing Better ADCs Using ThioBridge™ Conjugation", ABZENA—Enabling better biopharmaceuticals, World ADC Summit of Oct. 27, 2014, San Diego, 29 pages.

Brocchini et al., "PEGylation of native disulfide bonds in proteins", Nature Protocols, 2006, vol. 1, No. 5, pp. 2241-2252.

Carrico et al., Introducing Genetically Encoded Aldehydes into Proteins, Nature Chemical Biology, Jun. 2007, vol. 3, No. 6, pp. 321-322.

Davis et al., "In Vitro Characterization of the Drug-Drug Interaction Potential of Catabolites of Antibody-Maytansinoid Conjugates", Drug Metabolism and Disposition, Jun. 2012, vol. 40, No. 10, pp. 1927-1934.

Del Rosario et al., "Sulfhydryl Site-Specific Cross-Linking and Labeling of Monoclonal Antibodies by a Fluorescent Equilibrium Transfer Alkylation Cross-Link Reagent", Bioconjugate Chemistry, 1990, vol. 1, No. 1, pp. 51-59, XP002313938.

Dennler et al., "Transglutaminase-Based Chemo-Enzymatic Conjugation Approach Yields Homogeneous Antibody-Drug Conjugates", Bioconjugate Chemistry, 2014, vol. 25, pp. 569-578.

Doronina et al., "Development of potent monoclonal antibody aurostatin conjugates for cancer therapy," Nat. Biotech., 2003, vol. 21, No. 7, pp. 778-785.

Doronina et al., "Enhanced Activity of Monomethylauristatin F through Monoclonal Antibody Delivery: Effects of Linker Technology on Efficacy and Toxicity", Bioconjugate Chem, 2006, vol. 17, pp. 114-124.

Dubowchik et al., "Cathepsin b-labile dipeptide linkers for lysosomal release of doxorubicin from internalizing immunoconjugates: model studies of enzymatic drug release and antigen specific in vitro anticancer activity." Bioconjugate Chem., (2002) vol. 13, pp. 855-869.

Erickson, Hans et al., "Antibody-Maytansinoid Conjugates are Activated in Targeted Cancer Cells by Lysosomal Degradation and Linker-Dependent Intracellular Processing"; Cancer Research, American Association for Cancer Research, US; Apr. 15, 2006; vol. 66, No. 8, pp. 4426-4433, XP008074767.

Fishkin et al., "A novel pathway for maytansinoid release from thioether linked antibody-drug conjugates (ADCs) under oxidative conditions"; Chemical Communications; Jan. 1, 2011; vol. 47, No. 38, p. 10752; XP055152687.

Gondi et al., "Cathepsin B as a cancer target", Expert Opinion on Therapeutic Targets, 2013, vol. 17, No. 3, pp. 281-291, DOI: 10.1517/14728222.2013.740461.

Grumbach et al., "Hydrophilic Interaction Chromatography Using Silica Columns for the Retention of Polar Analytes and Enhanced ESI-S Sensitivity", LCGC, North America 2004, an Advanstar Publication, ID No. 7200001048EN.

Hofer et al., "An Engineered Selenocysteine Defines a Unique Class of Antibody Derivatives", Proc. Natl. Acad. Sci., Aug. 26, 2008, vol. 105, No. 34, pp. 12451-12456.

Hollander et al., "Selection of Reaction Additives Used in the Preparation of Monomeric Antibody-Calicheamicin Conjugates", Bioconjugate Chemistry, 2008, vol. 19, pp. 358-361.

International Search Report and Written Opinion mailed Aug. 28, 2014, for PCT/US2014/29757, 13 pages.

International Search Report and Written Opinion of PCT/US2014/052757 mailed Nov. 28, 2014, 13 pages.

International Search Report and Written Opinion of PCT/US2015/033618 mailed Dec. 21, 2015, 20 pages.

International Search Report and Written Opinion of PCT/US2017/014782 mailed Mar. 20, 2017, 13 pages.

Invitation together with the Search Report and Written Opinion issued by the Singapore Patent office mailed on Aug. 10, 2016, for the Singapore patent application No. 11201507481W; 11 pages.

(56)                References Cited

OTHER PUBLICATIONS

J. A. Davis et al., "In Vitro Characterization of the Drug-Drug Interaction Potential of Catabolites of Antibody-Maytansinoid Conjugates", Drug Metabolism And Disposition, Jun. 2012, 40:10; pp. 1927-1934.

J. A. Reddy et al., Folate Receptor-Specific Antitumor Activity of EC131, a Folate-Maytansinoid Conjugate, Cancer Research, Jul. 1, 2007; vol. 67, No. 12; pp. 6376-6382.

Kawai et al., "Chemical Modification of Ansamitocins 3. Synthesis and Biological Effects of 3 Acyl Esters of Maytansinol", Chemical And Pharmaceutical Bulletin, Pharmaceutical Society of Japan, vol. 32, No. 9, Jan. 1, 1984, pp. 3441-3451, XP008094318.

Phillips et al., "Targeting HER2-Positive Breast Cancer with Trastuzumab-DM1, an Antibody-Cytotoxic Drug Conjugate", Cancer Research, 2008, No. 62, p. 9280-9290. http://cancerres.aacrjournals.org/content/68/22/9280.full-text.pdf.

Pillow et al., "Site-Specific Trastuzumab Maytansinoid Antibody-Drug Conjugates with Improved Therapeutic Activity through Linker and Antibody Engineering", Journal of Medicinal Chemistry, Oct. 9, 2014, vol. 57, No. 19, pp. 7890-7899, XP055268691.

Rabuka et al., "Site-Specific Chemical Protein Conjugation Using Genetically Encoded Aldehyde Tags", Nat. Protocols, Dec. 1, 2012, vol. 7, No. 6, pp. 1052-1067.

Ryan et al., "Polyclonal Antibody Production Against Chito-Oligosaccharides", Food and Agricultural Immunology, 2001, vol. 13, pp. 127-130.

S. C. Jeffrey et al., "Dipeptide-Based Highly Potent Doxorubicin Antibody Conjugates," Bioorganic & Medicinal Chemistry Letters, 2006, vol. 16, pp. 358-362.

Salomon et al., "Sensitive Elisa Method for the Measurement of Catabolites of Antibody-Drug Conjugates (ADCs) in Target Cancer Cells", Molecular Pharmaceutics, Jun. 1, 2015, vol. 12, No. 6, pp. 1752-1761, XP055352192.

Sapra et al., "Monoclonal antibody-based therapies in cancer: Advances and Challenges", Pharmacology & Therapeutics, 2013, vol. 138, pp. 452-469.

Satyanarayanajois et al., "Medicinal chemistry for 2020", Fut. Med. Chem., (Oct. 2011), vol. 3, No. 14, pp. 1765-1786.

Search Report and Written Opinion issued by the Singapore Patent office, mailed on Aug. 10, 2016, for the SG application No. 11201507481W; 9 pages.

Shaunak et al., "Site-specific PEGylation of Native Disulfide Bonds in Therapeutic Proteins", Nature Chemical Biology, Jun. 2006, vol. 2, No. 6, pp. 312-313.

Sun et al., "Design of Antibody-Maytansinoid Conjugates Allows for Efficient Detoxification via Liver Metabolism", Bioconjugate Chemistry, Apr. 20, 2011, vol. 22, No. 4, pp. 728-735, XP055096244.

Tang et al., "The Analysis of Key Factors Related to ADCs Structural Design", Apr. 2019, vol. 10, article 373, DOI: 10.3389/fphar.2019.00373.

Trail, "Antibody Drug Conjugates as Cancer Therapeutics", Antibodies 2013, 2, pp. 113-129; doi:10.3390/antib2010113.

Widdison et al., "Development of Anilino-Maytansinoid ADCs that Efficiently Release Cytotoxic Metabolites in Cancer Cells and Induce High Levels of Bystander Killing", Bioconjugate Chemistry, DOI: 10.1021 / acs.bioconjchem.5b00430, 2015, pp. A-R (18 pages) together with Supporting Information Section, 2015, pp. 1-17.

Widdison et al., "Semisynthetic Maytansine Analogues for the Targeted Treatment of Cancer", Journal of Medicinal Chemistry, American Chemical Society, US; Jul. 13, 2006, vol. 49, No. 14, pp. 4392-4408, XP002679529.

Wolf Philipp, "Anti-psma antibody-drug conjugates and immunotoxins", Chapter 15 of Antibody-drug conjugates and immunotoxins (2012) Gail Phillips (ed), ISBN 978-1-4614-5456-4.

Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., vol. 101, 1979, pp. 395-399.

Zhao et al., "Synthesis and Evaluation of Hydrophilic Linkers for Antibody-Maytansinoid Conjugates", Journal of Medicinal Chemistry, May 26, 2011, vol. 54, No. 10, pp. 3606-3623; XP55046274.

* cited by examiner

MAYTANSINOID DERIVATIVES, CONJUGATES THEREOF, AND METHODS OF USE

CROSS-REFERENCE TO RELATED APPLICATIONS

This application is a continuation of U.S. patent application Ser. No. 16/663,251, filed Oct. 24, 2019, which is a continuation of U.S. patent application Ser. No. 15/907,142, filed Feb. 27, 2018, now U.S. Pat. No. 10,463,749, which is a continuation of Ser. No. 15/414,537, filed Jan. 24, 2017, now U.S. Pat. No. 9,950,076, which claims priority to, and the benefit of, U.S. Provisional Application No. 62/286,858, entitled MAYTANSINOID DERIVATIVES, CONJU-GATES THEREOF AND METHODS OF USE, which was filed Jan. 25, 2016, the entire contents of each of which are herein incorporated by reference in their entireties for all purposes.

FIELD

The present disclosure concerns maytansinoid com-pounds, derivatives thereof, conjugates thereof, and methods of treating or preventing proliferative diseases with the same.

BACKGROUND

Proliferative diseases, for example cancer, are character-ized by the uncontrolled growth of abnormal cells. Current treatments of proliferative diseases include surgery, radia-tion, chemotherapy, hormone-based therapy and/or immu-notherapy. A number of these treatments, particularly che-motherapy, utilize anti-proliferative drugs that limit the spread of the abnormal cells. However, these drugs are typically indiscriminate in their ability to kill cells, affecting both normal and abnormal cells. To address this problem, various approaches to targeted drug delivery have been explored, including the use of conjugates of tumor-targeted probes (such as antibodies or growth factors) with toxins, to selectively target abnormal cells. Antibody drug conjugates (ADCs) are compounds composed of an antibody that is linked, via a chemical linker, to a cytotoxic agent. Such compounds leverage the antibody's binding specificity for its target to deliver a cytotoxic agent to an abnormal cell. Thus, there is a need for anti-proliferative compounds and their conjugates.

SUMMARY

Provided herein are compounds of Formula (I):

(I)

or a pharmaceutically acceptable salt thereof, wherein:

A is a arylene or heteroarylene, optionally substituted as described herein;

L is a linker, optionally substituted as described herein;

BA is a binding agent; and k is an integer from 1 to 30. Also provided herein are stereoisomers of compounds of Formula (I).

Provided herein are also compounds of Formula (II):

(II)

or a pharmaceutically acceptable salt thereof, wherein A is arylene or heteroarylene, optionally substituted as described herein. Also provided herein are stereoisomers of com-pounds of Formula (II).

Provided herein are also compounds of Formula PP5:

PP5 or a salt thereof, wherein A is arylene or heteroarylene, optionally substituted as described herein. Also provided herein are stereoisomers of compounds of Formula PP5.

Furthermore, provided herein are methods of treating proliferative diseases comprising administering the com-pounds described herein.

Furthermore, provided herein are methods of treating proliferative diseases comprising administering the conju-gates described herein.

Furthermore, provided herein are methods of making a compound of Formula (I) comprising contacting a com-pound of Formula P1 with a binding agent,

P1

I

Furthermore, provided herein are methods of making a compound of Formula P1, comprising contacting a compound of Formula (II) with a reactive linker (RL) described herein.

Furthermore, provided herein are methods of making a compound of Formula (II), comprising contacting a compound of Formula PP5 with a suitable reducing agent.

Furthermore, provided herein are methods of making a compound of Formula PP5 comprising contacting a maytansinol with a nitro-phenyl-isocyanate.

BRIEF DESCRIPTIONS OF THE DRAWINGS

FIG. 9 depicts a reaction scheme referenced in Example 1.

FIG. 10 depicts a reaction scheme referenced in Example 2.

FIG. 11 depicts a reaction scheme referenced in Example 3.

FIG. 12 depicts a reaction scheme referenced in Example 4.

FIG. 13 depicts a reaction scheme referenced in Example 5.

FIG. 14 depicts a reaction scheme referenced in Example 6.

FIG. 15 depicts a reaction scheme referenced in Example 7.

FIG. 16 depicts a reaction scheme referenced in Example 8.

FIG. 17 depicts a reaction scheme referenced in Example 9.

DETAILED DESCRIPTION

A. Definitions

Figure 1:
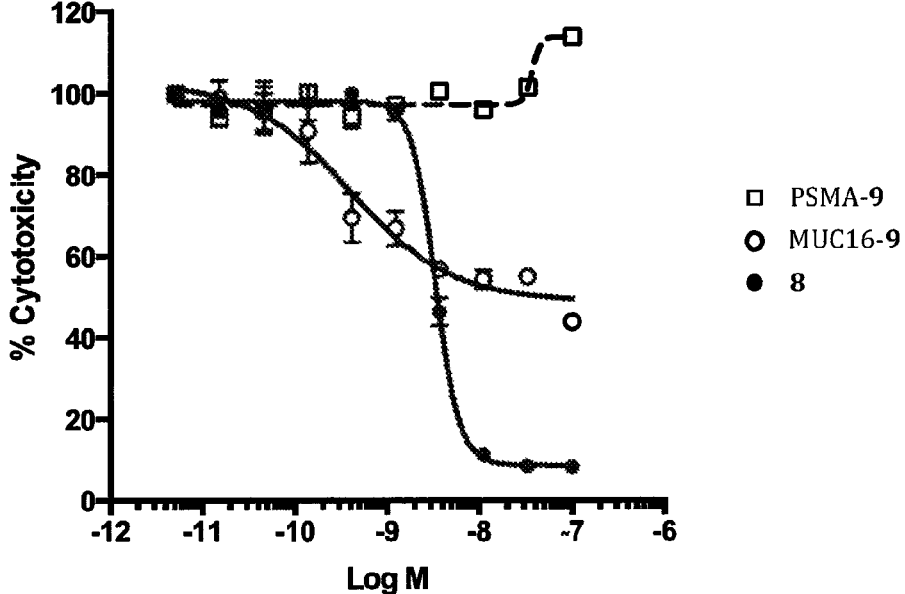
FIG. 1 depicts the plot of % Cell Viability OVCAR3 vs. $Log_{10}$ [M] of certain compounds tested in Example 28.
Figure 2:
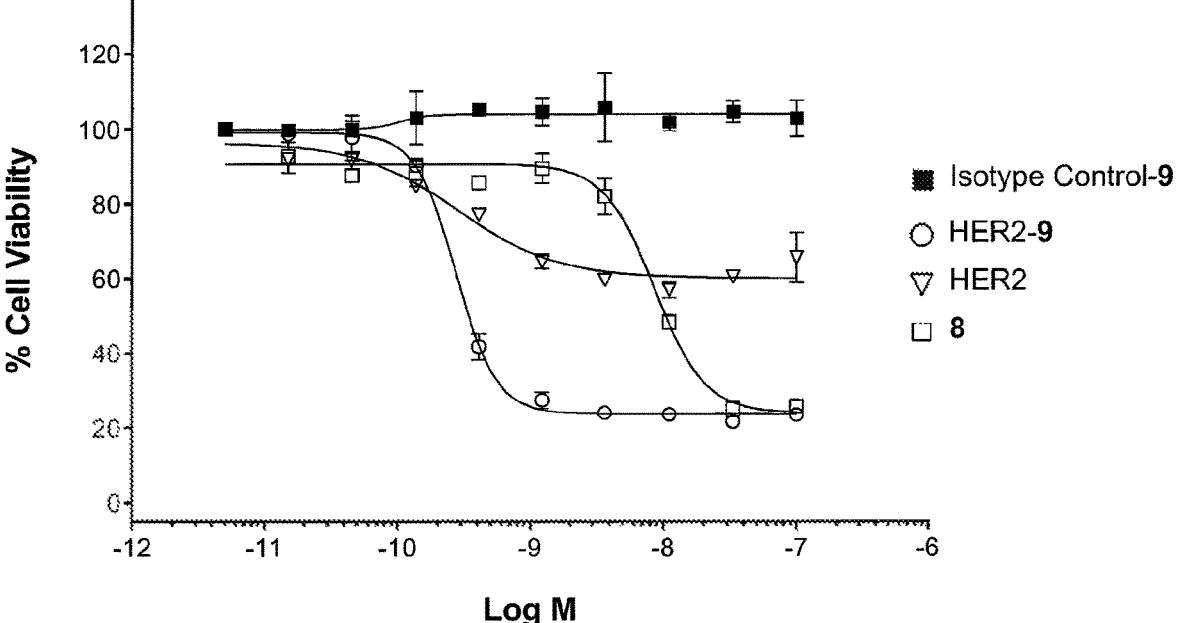
FIG. 2 depicts the plot of % Cell Viability SKBr3 vs. $Log_{10}$ [M] of certain compounds tested in Example 28.
Figure 3:
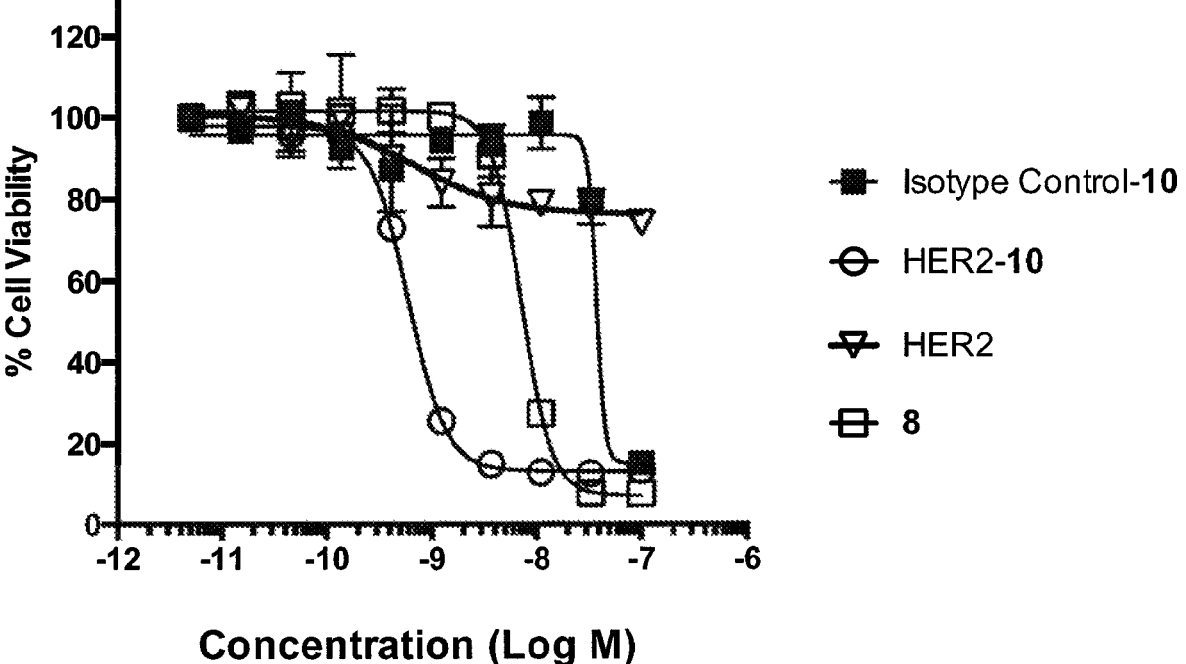
FIG. 3 depicts the plot of % Cell Viability SKBr3 vs. $Log_{10}$ [M] of certain compounds tested in Example 28.
Figure 4:
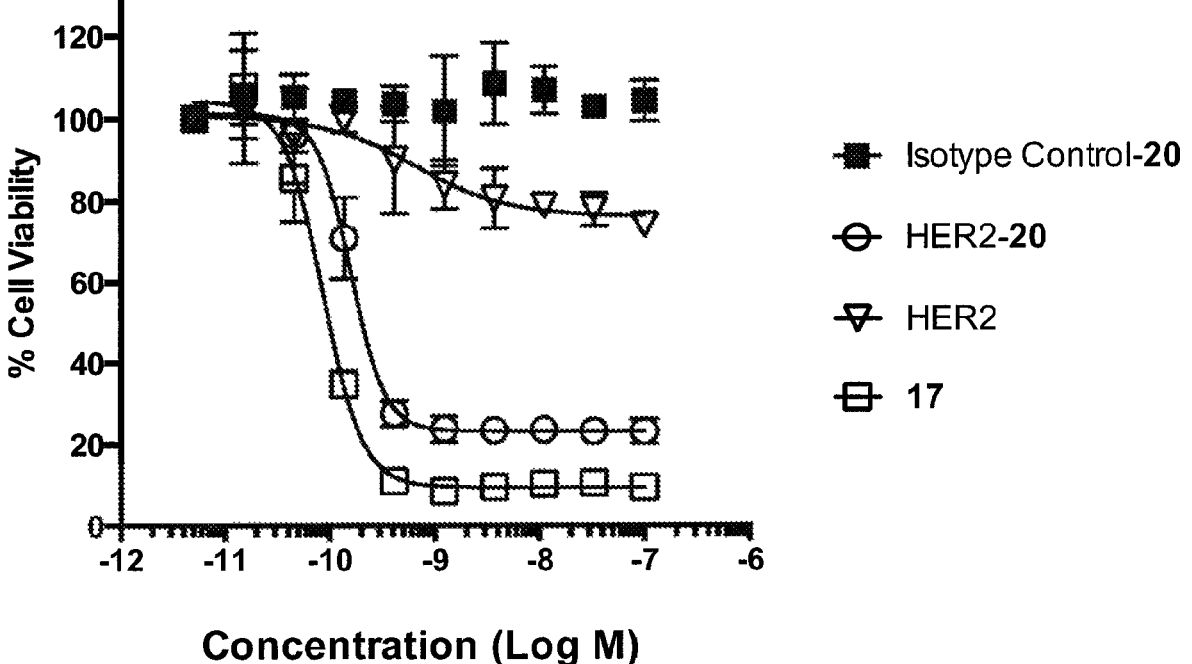
FIG. 4 depicts the plot of % Cell Viability SKBr3 vs. $Log_{10}$ [M] of certain compounds tested in Example 28.
Figure 5:
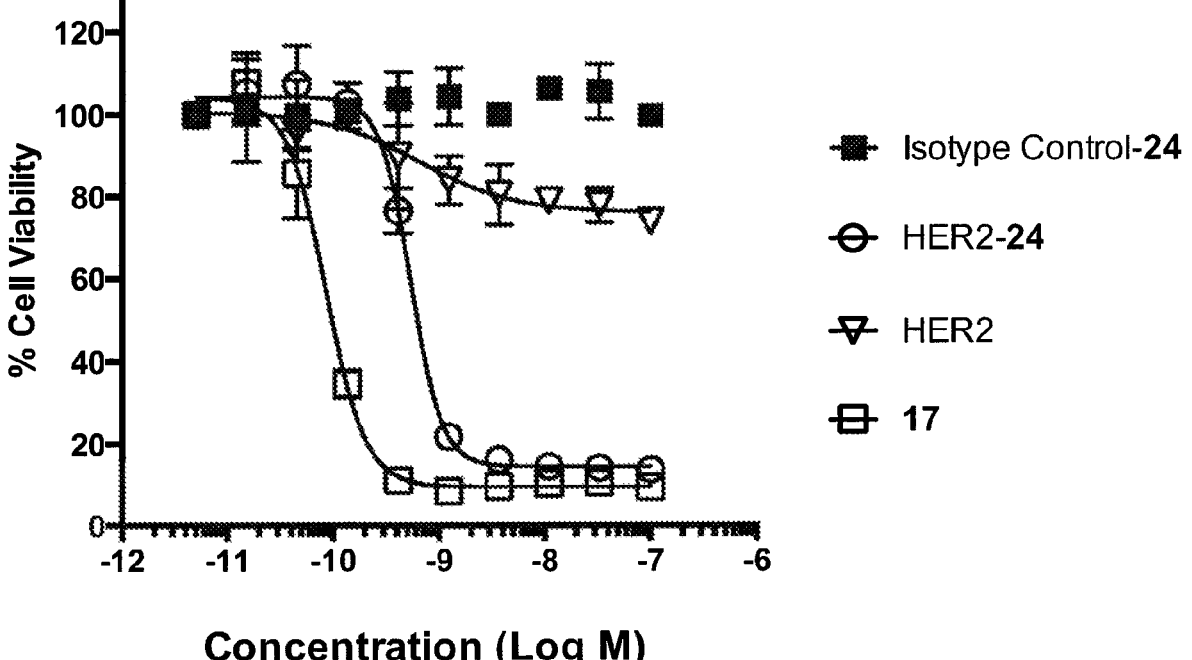
FIG. 5 depicts the plot of % Cell Viability SKBr3 vs. $Log_{10}$ [M] of certain compounds tested in Example 28.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl.

As used herein, "haloalkyl" refers to alkyl, as defined above, wherein the alkyl includes at least one substituent selected from a halogen, e.g., F, Cl, Br, or I.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O. for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are limited to phenyl, naphthyl, fluorenyl, azulenyl, anthryl, phenanthryl, and pyrenyl.

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of aryl moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "alkaryl" refers to an aryl that is substituted with at least one alkyl. Alkaryl is optionally substituted.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkenyl in which one or more carbon atoms are replaced by heteroatoms. Suitable heteroatoms include, but are not limited to, nitrogen, oxygen, and sulfur atoms. Heteroalkyl is optionally substituted.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more carbon ring atoms of the aromatic ring are replaced with an oxygen, sulfur, nitrogen, or phosphorus atom. Heteroarylene is optionally substituted and can be monocyclic or polycyclic, e.g., bicyclic or tricyclic.

As used herein, "optionally substituted," when used to describe a radical moiety, e.g., optionally substituted alkyl, means that such moiety is optionally bonded to one or more substituents. Examples of such substituents include, but are not limited to halo, cyano, nitro, haloalkyl, azido, epoxy, optionally substituted heteroaryl, optionally substituted heterocycloalkyl,

6

-continued wherein $R^A$, $R^B$, and $R^C$ are, independently at each occurrence, a hydrogen atom, alkyl, alkenyl, alkynyl, aryl, alkaryl, arylalkyl, heteroaryl, or heterocycloalkyl, or $R^A$ and $R^B$, together with the atoms to which they are bonded, form a saturated or unsaturated carbocyclic ring, wherein the ring is optionally substituted and wherein one or more ring atoms is optionally replaced with a heteroatom. In some embodiments, $R^A$, $R^B$, and $R^C$ are not hydrogen atoms.

As used herein, "binding agent" refers to any molecule capable of binding with specificity to a given binding partner.

As used herein, "linker" refers to a divalent moiety that covalently links the binding agent to the maytansinoid compounds and derivatives described herein.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refer to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropyl-carbodiimide (DIC), (benzotriazol-1-yloxy)tris(dimethyl-amino)phosphonium hexafluorophosphate (BOP), (benzo-triazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (Py-BrOP), O-(benzotriazol-1-yl)-N,N,N',N'-tetramethyluro-nium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b] pyridinium 3-oxid hexafluorophosphate (HATU), 2-Ethoxy-1-ethoxycarbonyl-1,2-dihydroquinoline (EEDQ), 1-Ethyl-3-(3-dimethylaminopropyl)carbodiimide (EDC), 2-Chloro-1, 3-dimethylimidazolidinium hexafluorophosphate (CIP), 2-chloro-4,6-dimethoxy-1,3,5-triazine (CDMT), and carbo-nyldiimidazole (CDI). In some examples, a carboxylic acid is first converted to an activated carboxylic ester before reacting with an amine to form an amide bond. In certain embodiments, the carboxylic acid is reacted with a reagent. The reagent activates the carboxylic acid by deprotonating the carboxylic acid and then forming a product complex with the deprotonated carboxylic acid as a result of nucleo-philic attack by the deprotonated carboxylic acid onto the protonated reagent. For certain carboxylic acids, this activated ester is more susceptible subsequently to nucleophilic attack by an amine than the carboxylic acid is before it is converted into an activated ester. This results in amide bond formation. As such, the carboxylic acid is described as activated. Exemplary reagents include DCC and DIC.

As used herein, "therapeutically effective amount" refers to an amount (of a compound) that is sufficient to provide a therapeutic benefit to a patient in the treatment or management of a disease or disorder, or to delay or minimize one or more symptoms associated with the disease or disorder.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl), $Zn(OTf)_2$, $ZnCl_2$, $Yb(OTf)_3$, $Sc(OTf)_3$, $MgBr_2$, $NiCl_2$, $Sn(OTf)_2$, $Ni(OTf)_2$, and $Mg(OTf)_2$.

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

has the following structure:

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group, wherein subscript q is an integer from 0 to 4 and in which the positions of substituent $R^1$ are described generically, includes the following groups in which the positions of substituent $R^1$ are described specifically:

-continued in which the positions of substituents other than $R^1$ which are bonded to the cyclic group through a bond between ring atoms are described generically, includes the following groups in which the positions of these substituents other than $R^1$ are described specifically:

In addition and for example, the group,

Also, for example, the group,

-continued in which the positions of substituents other than R$^1$ which are bonded to the cyclic group through a bond between ring atoms are described generically, includes the following groups in which the positions of these substituents other than R$^1$ are described specifically:

In each of these structures in which the positions of the substituents other than R$^1$ are described specifically, the substituent R$^1$ may be bonded to any ring position in the cyclic group or on any ring in the fused ring group which is not occupied by one of these substituents other than R$^1$. The following non-limiting representative illustrations indicate that the cyclic group can be substituted with the indicated substituent at any ring position or on either ring in the fused ring group:

When a group described herein is optionally substituted, the substituent bonded to the group is unsubstituted unless otherwise specified.

As used herein, the phrase "reactive linker," or the abbreviation "RL" refers to a monovalent group that includes a reactive group and spacer group, depicted for example as $$RG\!-\!SP\!-\!\xi$$

wherein RG is the reactive group and SP is the spacer group. As described herein, a reactive linker may include more than one reactive group and more than one spacer group. The spacer group is any divalent moiety that bridges the reactive group to another group, such as a payload. The reactive linkers (RL), together with the payloads to which they are bonded, provide intermediates ("linker-payloads") useful as synthetic precursors for the preparation of the antibody conjugates described herein. The reactive linker contains a reactive group ("RG"), which is a functional group or moiety that is capable of reacting with a reactive portion of another group, for instance, an antibody, modified antibody, or antigen binding fragment thereof, or an enhancement group. The moiety resulting from the reaction of the reactive group with the antibody, modified antibody, or antigen binding fragment thereof, together with the linking group, include the "binding agent linker" ("BL") portion of the conjugate, described herein. In certain embodiments, the "reactive group" is a functional group or moiety (e.g., maleimide or N-hydroxysuccinimide (NHS) ester) that reacts with a cysteine or lysine residue of an antibody or antigen-binding fragment thereof. In certain embodiments, the "reactive group" is a functional group or moiety that is capable of undergoing a click chemistry reaction (see, e.g., click chemistry, Huisgen *Proc. Chem. Soc.* 1961, Wang et al. *J. Am. Chem. Soc.* 2003, and Agard et al. *J. Am. Chem. Soc.* 2004). In some embodiments of said click chemistry reaction, the reactive group is an alkyne that is capable of undergoing a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with alkynes in the absence of copper catalysts. Suitable alkynes also include, but are not limited to, dibenzoazacyclooctyne or (DIBAC)

dibenzocyclooctyne or (DIBO)

biarylazacyclooctynone or (BARAC)

difluorinated cyclooctyne or (DIFO)

substituted, e.g., fluorinated alkynes, aza-cycloalkynes, bicycle[6.1.0]nonyne or (BCN, where R is alkyl, alkoxy, or acyl), and derivatives thereof. Particularly useful alkynes include and Linker-payloads including such reactive groups are useful for conjugating antibodies that have been functionalized with azido groups. Such functionalized antibodies include antibodies functionalized with azido-polyethylene glycol groups. In certain embodiments, such functionalized antibody is derived by treating an antibody having at least one glutamine residue, e.g., heavy chain Gln195, with a compound bearing an azide group, in the presence of the enzyme transglutaminase.

In some examples, the reactive group is an alkyne, e.g., which can react via click chemistry with an azide, e.g., to form a click chemistry product, e.g., or In some examples, the group reacts with an azide on a modified antibody or antigen binding fragment thereof. In some examples, the reactive group is an alkyne, e.g., which can react via click chemistry with an azide, e.g., to form a click chemistry product, e.g., In some examples, the reactive group is an alkyne, e.g., which can react via click chemistry with an azide, e.g., to form a click chemistry product, e.g., or In some examples, the reactive group is a functional group, e.g., which reacts with a cysteine residue on an antibody or antigen-binding fragment thereof, to form a bond thereto, e.g., wherein Ab refers to an antibody or antigen-binding fragment thereof and S refers to the S atom on a cysteine residue through which the functional group bonds to the Ab. In some examples, the reactive group is a functional group, e.g., which reacts with a lysine residue on an antibody or antigen-binding fragment thereof, to form a bond thereto, e.g., wherein Ab refers to an antibody or antigen-binding fragment thereof and NH refers to the NH atom on a lysine side chain residue through which the functional group bonds to the Ab.

B. Conjugates

Provided herein are compounds of Formula (I):

(I)

or a pharmaceutically acceptable salt thereof,
wherein:
    A is arylene or heteroarylene;
    L is a linker;
    BA is a binding agent; and
    k is an integer from 1 to 30.

1. "A" Moieties

In some embodiments, A is arylene. In some embodiments, A is heteroarylene. In some embodiments, the arylene or heteroarylene is substituted with one or more electron withdrawing groups and/or one or more electron donating groups.

In some embodiments, A is a divalent radical of benzene, of pyridine, of naphthalene, or of quinolone, which are optionally substituted.

In some embodiments, A is a divalent radical of benzene which is optionally substituted with a member selected from the group consisting of amino, amido, alkyl, halo, haloalkyl, alkoxy, and haloalkoxy.

In some embodiments, A is a divalent radical of benzene which is optionally substituted with a member selected from the group consisting of alkyl, alkoxy, haloalkyl, and halo. In some embodiments, A is a divalent radical of benzene which is optionally substituted with a member selected from the group consisting of methyl, methoxy, trifluoromethyl, fluoro, chloro, and bromo. In some embodiments, A is a divalent radical of benzene which is optionally substituted with a member selected from the group consisting of halo, haloalkyl, haloalkoxy, alkyl, alkenyl, alkynyl, alkoxy, aryl, alkaryl, arylalkyl, heteroaryl, heteroalkyl, heterocycloalkyl, cyano, nitro, amino, or azido, wherein $R^A$ is alkyl.

In some embodiments A is:

wherein:
    $R^1$, independently at each occurrence, is halo, haloalkyl, haloalkoxy, alkyl, alkenyl, alkynyl, alkoxy aryl, alky alkaryl, heteroaryl, heteroalkyl, heterocycloalkyl, cyano, nitro, amino, or azido,
    wherein $R^A$ is alkyl;
n is an integer from 0 to 4;
m is an integer from 0 to 3;
p is an integer from 0 to 6; and
q is an integer from 0 to 5.
In some embodiments, A is:

wherein:
    $R^1$, independently at each occurrence, is halo, haloalkyl, haloalkoxy, alkyl, alkenyl, alkynyl, alkoxy, aryl, alkaryl, arylalkyl, heteroaryl, heteroalkyl, heterocycloalkyl, cyano, nitro, amino, or azido, wherein $R^A$ is alkyl; and n is an integer from 0 to 4. In some embodiments, n is 0, 1, 2, or 3. In some embodiments, n is 0, 1, or 2. In some embodiments, n is 0 or 1. In some embodiments, n is 1. In some embodiments, A is:

wherein:

$R^1$, independently at each occurrence, is selected from alkyl, alkoxy, halo, haloalkyl, and heterocycloalkyl; and n is an integer from 0 to 4. In some embodiments, n is 0, 1, 2, or 3. In some embodiments, n is 0, 1, or 2. In some embodiments, n is 0 or 1. In some embodiments, n is 1. In some embodiments, A is:

wherein:

$R^1$, independently at each occurrence, is halo, haloalkyl, haloalkoxy, alkyl, alkenyl, alkynyl, alkoxy, aryl, alkaryl, arylalkyl, heteroaryl, heteroalkyl, heterocycloalkyl, cyano, nitro, amino, or azido, wherein $R^A$ is alkyl;

n is an integer from 0 to 4;

m is an integer from 0 to 3;

p is an integer from 0 to 6; and q is an integer from 0 to 5.

In some embodiments, $R^1$, independently at each occurrence, is halo, haloalkyl, haloalkoxy, alkyl, alkenyl, alkynyl, alkoxy, aryl, alkaryl, arylalkyl, heteroaryl, heteroalkyl, heterocycloalkyl, cyano, nitro, amino, or azido, wherein $R^A$ is alkyl;

In some embodiments, $R^1$, independently at each occurrence, is selected from alkyl, alkoxy, halo, haloalkyl, and heterocycloalkyl.

In some embodiments, $R^1$ is $C_{1-6}$ alkyl or $C_{1-6}$ alkoxy. In some embodiments, $R^1$ is $C_1$. In some embodiments, $R^1$ is $C_1$ alkoxy. In some embodiments, $R^1$ is halo. In some embodiments, $R^1$ is haloalkyl. In some embodiments, $R^1$ is heterocycloalkyl. In some of these embodiments, $R^1$ is methyl, ethyl, methoxy, or ethoxy. In some of these embodiments, $R^1$ is methyl. In some of these embodiments, $R^1$ is methoxy. In some of these embodiments, $R^1$ is trifluoromethyl. In some embodiments, $R^1$ is fluoro, chloro, or bromo. In some embodiments, $R^1$ is fluoro. In some embodiments, $R^1$ is chloro. In some embodiments, $R^1$ is bromo. In some of these embodiments, $R^1$ is pyrrolidinyl. In some of these embodiments, $R^1$ is morpholinyl.

In some embodiments, $R^1$ is, independently, alkyl or halo. In some embodiments, $R^1$ is, independently, $C_{1-6}$ alkyl, $C_{1-6}$ haloalkyl, or halo. In some embodiments, $R^1$ is, independently, halo. In some embodiments, $R^1$ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, $R^1$ is, independently, alkyl, alkoxy, or halo. In some embodiments, $R^1$ is, independently, $C_{1-6}$ alkyl, $C_{1-6}$ alkoxy, $C_{1-6}$ haloalkyl, $C_{1-6}$ haloalkoxy, or halo. In some embodiments, $R^1$ is, independently, halo. In some embodiments, $R^1$ is, independently, fluoro, chloro, bromo, iodo, or trifluoromethyl. In some embodiments, $R^1$ is $C_1$ alkoxy. In some embodiments, $R^1$ is halo. In some of these embodiments, $R^1$ is methyl. In some of these embodiments, $R^1$ is methoxy. In some of these embodiments, $R^1$ is trifluoromethyl. In some embodiments, $R^1$ is fluoro, chloro, or bromo. In some embodiments, $R^1$ is fluoro. In some embodiments, $R^1$ is chloro. In some embodiments, $R^1$ is bromo. In some embodiments, n, m, p, or q is 0, 1 or 2. In some embodiments, n, m, p, or q is 0 or 1. In some embodiments, n, m, p, or q is 0.

In some embodiments, A is:

In some embodiments, A is:

In some embodiments, A is:

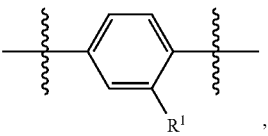

wherein n is 0, 1, 2, 3, or 4.

In some embodiments, A is:

wherein n is 0, 1, or 2. In some examples, n is 0 or 1; and $R^1$ is alkyl, alkoxy, halo, haloalkyl, or haloalkoxy. In some examples, $R^1$ is alkyl, alkoxy, halo, haloalkyl, or heterocycloalkyl. In some embodiments, $R^1$, independently at each occurrence, is halo, haloalkyl, haloalkoxy, alkyl, alkenyl, alkynyl, alkoxy aryl, alkaryl, arylalkyl, heteroaryl, heteroalkyl, heterocycloalkyl, cyano, nitro, amino, $$—OR^A, \quad —SO_2R^A, \quad —\overset{O}{\underset{\parallel}{C}}—R^A,$$

or azido, wherein $R^A$ is alkyl.

In some embodiments, A is:

wherein n is 0, 1, or 2. In some examples, n is 0 or 1; and $R^1$ is $C_{1-6}$ alkyl, $C_{1-6}$ alkoxy, halo, $C_{1-6}$ haloalkyl, $C_{1-6}$ haloalkoxy. In some examples, $R^1$ is heterocycloalkyl. In some embodiments, $R^1$ is methyl, methoxy, trifluoromethyl, fluoro, chloro, or bromo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is bromo. In some embodiments, $R^1$ is chloro. In some examples, $R^1$ is pyrrolidinyl. In some examples, $R^1$ is morpholinyl.

In some embodiments, A is:

wherein n is 0, 1, or 2. In some examples, n is 0 or 1; $R^1$ is $C_{1-6}$ alkyl, $C_{1-6}$ alkoxy, halo, $C_{1-6}$ haloalkyl, $C_{1-6}$ haloalkoxy, or heterocycloalkyl; and L is wherein b is an integer from 2 to 8 and is a bond to the binding agent.

In some embodiments A is:

wherein n is 0, 1, 2, 3, or 4.

In some embodiments, A is:

wherein $R^1$ is $C_{1-6}$ alkyl, $C_{1-6}$ alkoxy, halo, $C_{1-6}$ haloalkyl, $C_{1-6}$ haloalkoxy, or heterocycloalkyl. In certain of these embodiments, $R^1$ is methoxy or methyl. In some specific embodiments, $R^1$ is methoxy. In some embodiments, $R^1$ is methyl. In some embodiments, $R^1$ is methyl, methoxy, trifluoromethyl, fluoro, chloro, or bromo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is bromo. In some embodiments, $R^1$ is chloro. In some examples, $R^1$ is pyrrolidinyl. In some examples, $R^1$ is morpholinyl. In some examples, $R^1$ is alkyl, alkoxy, halo, haloalkyl, or heterocycloalkyl. In some embodiments, $R^1$, independently at each occurrence, is halo, haloalkyl, haloalkoxy, alkyl, alkenyl, alkynyl, alkoxy, aryl, alkaryl, arylalkyl, heteroaryl, heteroalkyl, heterocycloalkyl, cyano, nitro, amino, $$—OR^A, \quad —SO_2R^A, \quad —\overset{O}{\underset{\parallel}{C}}—R^A,$$

or azido, wherein $R^A$ is alkyl.

In some embodiments, A is:

wherein:

$R^1$ is halo, methyl, methoxy, or trifluoromethyl; and n is 0, 1 or 2.

In some embodiments, A is:

In some embodiments, A is:

wherein:

X is a hydrogen atom, halo, methyl, methoxy, or trifluoromethyl.

In some embodiments, A is:

wherein:

X is a hydrogen atom, halo, methyl, methoxy, or trifluoromethyl;

is the bond to the nitrogen atom of the amino-ester which is directly bonded to the drug molecule; and is the bond to the nitrogen atom which is bonded to the linker.

In some embodiments, A is:

wherein:

$R^1$ is, independently at each occurrence, a hydrogen atom, alkyl, alkoxy, aryl, heteroalkyl, heterocycloalkyl, halo, haloalkyl, or haloalkoxy;

and areas defined above. In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methyl. In some embodiments, $R^1$ is methoxy. In some embodiments, $R^1$ is fluoro. In some embodiments, $R^1$ is chloro. In some embodiments, $R^1$ is bromo. In some embodiments, $R^1$ is hydrogen.

In some embodiments, A is:

wherein:

$R^1$ is, independently at each occurrence, a hydrogen atom, alkyl, alkoxy, aryl, heteroalkyl, heterocycloalkyl, halo, haloalkyl, haloalkoxy;

as a defined above. In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methyl. In some embodiments, $R^1$ is methoxy. In some embodiments, $R^1$ is fluoro. In some embodiments, $R^1$ is chloro. In some embodiments, $R^1$ is bromo. In some embodiments, $R^1$ is hydrogen.

In some embodiments, A is:

25

26 wherein:

R$^1$ is, independently at each occurrence, a hydrogen atom, alkyl, alkoxy, aryl, heteroalkyl, heterocycloalkyl, halo, haloalkyl, or haloalkoxy;

In some embodiments, A is:

are as defined above. In some embodiments, R$^1$ is, independently at each occurrence, a hydrogen atom, alkyl, alkoxy, aryl, heteroalkyl, heterocycloalkyl, halo, haloalkyl, or haloalkoxy. In some embodiments, R$^1$ is alkyl or alkoxy. In some specific embodiments, R$^1$ is propylamino, difluoromethoxy, phenyl, 2-fluorophenyl. In some embodiments, R$^1$ is trifluoromethyl. In some embodiments, R$^1$ is methoxy. In some embodiments, R$^1$ is methyl. In some embodiments, R$^1$ is fluoro. In some embodiments, R$^1$ is chloro. In some embodiments, R$^1$ is bromo. In some embodiments, R$^1$ is hydrogen. In some examples, R$^1$ is pyrrolidinyl. In some examples, R$^1$ is morpholinyl.

In some embodiments, A is:

are as defined above.

In some embodiments, A is:

In some embodiments, A is:

are as defined above.

In some embodiments, A is:

are as defined above.

In some embodiments, A is:

are as defined above.

In some embodiments, A is:

are as defined above.

In some embodiments, A is:

are as defined above.

27 and are as defined above.

In some embodiments, A is:

$F_3C$—

;

and are as defined above.

In some embodiments, A is:

$F$—

;

and are as defined above.

In some embodiments, A is:

$Cl$ $F$—

;

and are as defined above.

28

In some embodiments, A is:

$Cl$—

;

15 and are as defined above.

In some embodiments, A is:

$F_3C$

;

35 and are as defined above.

In some embodiments, A is:

$F$

;

60 and

65 are as defined above.

In some embodiments, A is:

are as defined above.

In some embodiments, A is:

are as defined above.

In some embodiments, A is:

are as defined above.

In some embodiments, A is:

are as defined above.

In some embodiments, A is:

are as defined above.

In some embodiments, A is:

are as defined above.

In some embodiments, A is:

are as defined above.

In some embodiments, A is:

In some embodiments, A is:

are as defined above.

In some embodiments, A is:

are as defined above.

In some embodiments, A is:

are as defined above.

In some embodiments, A is:

are as defined above.

In some embodiments, A is:

are as defined above.

In some embodiments, A is:

are as defined above.

33

In some embodiments, A is:

In some embodiments, A is:

are as defined above.

In some embodiments, A is:

are as defined above.

In some embodiments, A is:

are as defined above.

34

In some embodiments, A is:

wherein X is F, Cl, Br, CN, methoxy, methyl, trifluorom-ethyl, dimethylamino or cyclopropyl;

are as defined above. In some embodiments, A is:

wherein X is F, Cl, Br, CN, methoxy, methyl, trifluorom-ethyl, dimethylamino, 1-methyl-ethyl-thio or cyclopropyl;

are as defined above.

In some embodiments, A is:

wherein each $R^1$ is independently, at each occurrence, a hydrogen atom, alkyl, alkoxy, halo, haloalkyl, or haloalkoxy;

are as defined above. In some embodiments, $R^1$ is hydrogen, fluoro, methyl, trifluoromethyl, or methoxy. In some embodiments, $R^1$ is fluoro, chloro, bromo, or iodo.

35

36

In some embodiments, A is:

, wherein and are as defined above.

In some embodiments, A is:

, wherein each R¹ is independently, at each occurrence, a hydrogen atom, alkyl, alkoxy, halo, haloalkyl, or haloalkoxy; wherein and are as defined above.

In some embodiments, A is:

;

wherein and are as defined above.

In some embodiments, A is:

, or

.

In some embodiments, A is:

.

In some embodiments, A is:

.

In some embodiments, A is:

, wherein:
wherein and are as defined above.

37

In some embodiments, A is:

wherein:
wherein are as defined above.
In some embodiments, A is:

wherein:
wherein are as defined above.
In some embodiments, A is:

wherein:
wherein are as defined above.

38

In some embodiments, A is:

In some embodiments, A is:

In some embodiments, A is:

wherein n is 0, 1 2, or 3.
In some embodiments, A is:

wherein n is 0, 1 2, or 3.
In some embodiments, A is:

wherein:
$R^1$ is $C_{1-6}$ alkyl, $C_{1-6}$ alkoxy, halo, $C_{1-6}$ haloalkyl, $C_{1-6}$ haloalkoxy, $C_{1-6}$ heteroalkyl, or heterocycloalkyl; and n is 0, 1 2, 3 or 4. In some embodiments, $R^1$ is $C_{1-6}$ alkyl, $C_{1-6}$ alkoxy, halo, $C_{1-6}$ haloalkyl, $C_{1-6}$ haloalkoxy, $C_{1-6}$ heteroalkyl, or heterocycloalkyl.

In some embodiments, A is:

In some embodiments, A is:

In some embodiments, A is:

-continued wherein:

X is, independently at each occurrence, a hydrogen atom, alkyl, alkoxy, halo, haloalkoxy, haloalkyl, heteroalkyl, or heterocycloalkyl. In some embodiments, X is independently at each occurrence, a hydrogen atom, alkyl, alkoxy, halo, haloalkoxy, haloalkyl, heteroalkyl, or heterocycloalkyl. In some embodiments, X is fluoro, chloro, bromo, iodo, dimethylamino, methylamino, methyl, methoxy, ethoxy, or trifluoromethyl. In some embodiments, X is methyl. In some embodiments, X is methoxy. In some embodiments, X is trifluoromethyl. In some embodiments, X is fluoro. In some embodiments, X is chloro. In some embodiments, X is bromo. In some embodiments, X is morpholinyl. In some embodiments, X is pyrrolidinyl.

In some embodiments, A is:

41
-continued

42
-continued wherein:

X is, independently at each occurrence, a hydrogen atom, alkyl, alkoxy, halo, haloalkoxy, haloalkyl, heteroalkyl, or heterocycloalkyl. In some embodiments, X is independently at each occurrence, a hydrogen atom, alkyl, alkoxy, halo, haloalkoxy, haloalkyl, heteroalkyl, or heterocycloalkyl. In some embodiments, X, independently at each occurrence, fluoro, chloro, bromo, iodo, dimethylamino, methyl, methylamino, methoxy, ethoxy, trifluoromethyl methoxy, pyrrolidinyl, or morpholinyl;

wherein are as defined above. In some embodiments, X is methyl. In some embodiments, X is methoxy. In some embodiments, X is trifluoromethyl. In some embodiments, X is fluoro. In some embodiments, X is chloro. In some embodiments, X is bromo. In some embodiments, X is morpholinyl. In some embodiments, X is pyrrolidinyl.

In some embodiments, A is:

wherein:

X is, independently at each occurrence, a hydrogen atom, alkyl, alkoxy, halo, haloalkoxy, haloalkyl, heteroalkyl, or heterocycloalkyl. In some embodiments, X is independently at each occurrence, a hydrogen atom, alkyl, alkoxy, halo, haloalkoxy, haloalkyl, heteroalkyl, or heterocycloalkyl. In some embodiments, X is fluoro, chloro, bromo, iodo, dimethylamino, methylamino, methyl, methoxy, ethoxy, or trifluoromethyl. In some embodiments, X is methyl. In some embodiments, X is methoxy. In some embodiments, X is trifluoromethyl. In some embodiments, X is fluoro. In some embodiments, X is chloro. In some embodiments, X is bromo. In some embodiments, X is morpholinyl. In some embodiments, X is pyrrolidinyl.

In some embodiments, A is:

43

-continued wherein:

X is, independently at each occurrence, a hydrogen atom, alkyl, alkoxy, halo, haloalkoxy, haloalkyl, heteroalkyl, or heterocycloalkyl. In some embodiments, X, independently at each occurrence, fluoro, chloro, bromo, iodo, dimethylamino, methyl, methylamino, methoxy, ethoxy, trifluoromethyl methoxy, pyrrolidinyl, or morpholinyl;

wherein are as defined above. In some embodiments, X is methyl. In some embodiments, X is methoxy. In some embodiments, X is trifluoromethyl. In some embodiments, X is fluoro. In some embodiments, X is chloro. In some embodiments, X is bromo. In some embodiments, X is morpholinyl. In some embodiments, X is pyrrolidinyl.

2. Linkers

The linker portion of the conjugates described herein is a divalent moiety that covalently links the binding agent to the maytansinoid compounds and derivatives described herein. Suitable linkers include those that release at least the maytansinoid portion in the presence of an enzyme or at a particular pH range or value.

In some embodiments, the linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the reactive linker comprises a non-cleavable moiety. In some embodiments, the non-cleavable reactive linker is

44 or a residue thereof. In some embodiments, the non-cleavable reactive linker is or a residue thereof.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, or derivative thereof.

In some embodiments, the linker comprises valine and citrulline.

In some embodiments, the linker is:

wherein:

SP is a spacer;

is one or more bonds to the binding agent;

AA$^1$ is an amino acid; and

AA$^2$ is an amino acid.

In some embodiments, the linker is:

wherein:

SP is a spacer; and is one or more bonds to the binding agent

In some examples, the spacer is a divalent moiety that connects the AA$^1$-AA$^2$ moiety to the binding agent (BA). Suitable spacers include, but are not limited to, those comprising alkylene or polyethylene glycol. The ends of the spacers, i.e., the portion of the spacer directly bonded to the binding agent or AA$^1$, can be moieties derived from reactive moieties that are used for purposes of coupling the naked antibody or AA$^1$ to the spacer during the chemical synthesis of the conjugate. In some examples, the ends of the spacers, i.e., the portion of the spacer directly bonded to the binding agent or AA$^1$, can be residues of reactive moieties that are used for purposes of coupling the naked antibody or AA$^1$ to the spacer during the chemical synthesis of the conjugate.

In some embodiments, the spacer comprises an alkylene. In some embodiments, the spacer comprises a C$_{5-7}$ alkylene. In some embodiments, the spacer is:

wherein:

is a bond to the binding agent; and b is an integer from 2 to 8. In some examples, b is selected from 2, 3, 4, 5, 6, 7, or 8. In some examples, b is 2. In some examples, b is 3. In some examples, b is 4. In some examples, b is 5. In some examples, b is 6. In some examples, b is 7. In some examples, b is 8.

In some embodiments, the spacer is:

-continued wherein:

is a bond to the binding agent.

In some embodiments, the spacer is:

wherein:

is a bond to the binding agent

In some embodiments, the spacer is:

47

48 wherein:

$R^N$ is a hydrogen atom or alkyl;

$R^M$ is alkyl;

the two bonds represented by are bonds to cysteines of a binding agent; and b is an integer from 2 to 8.

In some embodiments, the spacer is:

wherein:

is a bond to the binding agent; and b is an integer from 2 to 8.

In some embodiments, the spacer is:

wherein:

is a bond to the binding agent; and g is an integer from 2 to 20. In some embodiments, g is 2-8. In some embodiments, g is 2, 4, 6, or 8.

In some embodiments, the spacer is:

In some embodiments, the spacer is:

In some embodiments, the spacer is:

In some embodiments, the spacer is:

In some embodiments, the spacer is:

In some embodiments, the spacer is:

In some embodiments, the spacer is:

49                                                          50

In some embodiments, the spacer is:                        In some embodiments, the linker is:

$$\text{(spacer structure with } BA\text{-}S \text{ labels, } O, CH_3\text{)}$$

In some embodiments, the spacer is:                        wherein:

SP is a spacer;

$$\text{(spacer structure with } BA\text{-}S \text{ labels, } O, H_3C, CH_3\text{)}$$

is one or more bonds to the binding agent;

$R^{AA1}$ is an amino acid side chain; and $R^{AA2}$ is an amino acid side chain.

In some embodiments, the spacer is:

As used herein, "amino acid side chain" refers the mon-
ovalent non-hydrogen substituent bonded to the α-carbon of
an α-amino acid, including natural and non-natural amino
acids. Exemplary amino acid side chains include, but are not
limited to, the α-carbon substituent of alanine, valine, leu-
cine, isoleucine, methionine, tryptophan, phenylalanine,
proline, serine, threonine, cysteine, tyrosine, asparagine,
glutamine, aspartic acid, glutamic acid, lysine, arginine,
histidine, and citrulline.

In some embodiments, the linker is:

$$\text{(structure with } R^N, R^M, X, (CH_2)_b, O \text{)}$$

or $$\text{(structure with } R^N, R^M, X, (CH_2)_b, O, CH_3 \text{)}$$

wherein

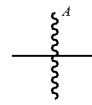

is a bond to the binding agent;

X is N or O; $R^N$ and $R^M$ are each, independently, hydrogen
or alkyl; and b is an integer from 1 to 8.

In some embodiments, $AA^1$-$AA^2$ is: valine-citrulline, cit-
rulline-valine, lysine-phenylalanine, phenylalanine-lysine,
valine-asparagine, asparagine-valine, asparagine-threonine,
threonine-asparagine, serine-asparagine, asparagine-serine,
phenylalanine-asparagine, asparagine-phenylalanine, leu-
cine-asparagine, asparagine-leucine, isoleucine-asparagine,
asparagine-isoleucine, glycine-asparagine, asparagine-gly-
cine, glutamic acid-asparagine, asparagine-glutamic acid,
citrulline-asparagine, asparagine-citrulline, alanine-aspara-
gine, asparagine-alanine, valine-alanine, alanine-valine,
valine-glycine, or glycine-valine.

In some embodiments, $AA^1$-$AA^2$ is: valine-citrulline or
citrulline-valine. In some embodiments, $AA^1$-$AA^2$ is:
valine-citrulline.

wherein:

SP is a spacer; and is one or more bonds to the binding agent.

In some embodiments, the linker is:

wherein:

is a bond to the binding agent; and b is an integer from 2 to 8.

In some embodiments, the linker is:

wherein:

is a bond to the binding agent; and b is an integer from 2 to 8.

In some embodiments, BA is an antibody and the linker is:

wherein:

the two bonds represented by are bonds to cysteines of the antibody; and b is an integer from 2 to 8.

In some embodiments, BA is an antibody and the linker is:

wherein:

the two bonds represented by are bonds to cysteines of the antibody; and b is an integer from 2 to 8.

In some embodiments, BA is an antibody and the linker is:

wherein:

$R^N$ is a hydrogen atom or alkyl;

$R^M$ is alkyl;

the two bonds represented by are bonds to cysteines of the antibody; and b is an integer from 2 to 8.

In some embodiments, the linker is:

wherein:

is a bond to the binding agent; and b is an integer from 2 to 8.

In some embodiments, the linker is:

wherein:

is a bond to the binding agent; and g is an integer from 2 to 20. In some embodiments, g is 2 to 8. In some embodiments, g is 2, 4, 6, or 8.

In some embodiments, the linker is:

In some embodiments, the linker is:

In some embodiments, the linker is:

In some embodiments, the linker is:

In some embodiments, the linker is:

In some embodiments, the linker is:

In some embodiments, the linker is:

In some embodiments, the linker is:

3. Binding Agents

Suitable binding agents include, but are not limited to, antibodies, lymphokines, hormones, growth factors, viral receptors, interleukins, or any other cell binding or peptide binding molecules or substances.

In some embodiments, the binding agent is an antibody. In some embodiments, the antibody is a monoclonal antibody, polyclonal antibody, antibody fragment (Fab, Fab', and F(ab)2, minibody, diabody, tribody, and the like), or bispecific antibody. Antibodies herein can be humanized using methods described in U.S. Pat. No. 6,596,541 and US Publication No. 2012/0096572, each incorporated by reference in their entirety.

Where the binding agent is an antibody, it binds to an antigen binding partner that is a polypeptide and may be a transmembrane molecule (e.g., receptor) or a growth factor that might be glycosylated or phosphorylated. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β, TGF-β4, or TGF-β5; insulin-like growth factor-1 and -II (IGF-1 and IGF-II); des(I-3)-IGF-l (brain IGF-1), insulin-like growth factor binding proteins, EpCAM, GD3, FLT3, PSMA, PSCA, MUC1, MUC16, STEAP, STEAP2, CEA, TENB2, EphA receptors, EphB receptors, folate receptor, FOLRI, mesothelin, cripto, alphavbeta6, integrins, VEGF, VEGFR, EGFR, transferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins, GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins, MART-1, mesothelin, ML-IAP, Muc1, Muc16, CA-125, MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides. In some examples, the GAGE proteins are selected from GAGE-1 and GAGE-2. In some examples, the MAGE proteins are selected from MAGE-1, -2, -3, -4, -6, and -12

Exemplary antigens also include, but are not limited to, BCMA, SLAMF7, B7H4, GPNMB, UPK3A, and LGR5. Exemplary antigens also include, but are not limited to, MUC16, PSMA, STEAP2, and HER2.

In some embodiments, the antigens include prolactin receptor (PRLR) or prostate-specific membrane antigen (PSMA). In some embodiments, the antigens include MUC16. In some embodiments, the antigens include STEAP2. In some embodiments, the antigens include PSMA. In some embodiments, the antigens include HER2. In some embodiments, the antigen is prolactin receptor (PRLR) or prostate-specific membrane antigen (PSMA). In some embodiments, the antigen is MUC16. In some embodiments, the antigens include PSMA. In some embodiments, the antigen is HER2. In some embodiments, the antigen is STEAP2.

Binding agents also include, but are not limited to, ankyrin repeat proteins, interferons, lymphokines such as IL-2 or IL-3, hormones like insulin and glucocorticoids, growth factors such as EGF, transferrin and fibronectin type III.

In some embodiments, the binding agents interact with or bind to tumor antigens, including antigens specific for a type of tumor or antigens that are shared, overexpressed or modified on a particular type of tumor. Examples include, but are not limited to: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2.

In some embodiments, the binding agent is an antibody. In some embodiments, the binding agent is a monoclonal antibody. In some embodiments, the binding agent is a polyclonal antibody. In some embodiments, the antibody is an anti-PSMA, anti-MUC16, anti-HER2, or anti-EGFRvIII, or anti-STEAP-2 antibody.

The linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872;

WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can be conjugated via glutamine via transglutaminase-based chemo-enzymatic conjugation (see, e.g., Dennler et al., *Bioconjugate Chem.* 2014, 25, 569-578). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, WO 2014/197854, and Shaunak et al., *Nat. Chem. Biol.,* 2006, 2:312-313).

In some embodiments, the binding agent is an antibody, and the antibody is bonded to the linker through a lysine residue. In some embodiments, the antibody is bonded to the linker through a cysteine residue.

4. Illustrative Embodiments

In some embodiments,

A is:

wherein:

R$^1$, independently at each occurrence, is halo, haloalkyl, haloalkoxy, alkyl, alkenyl, alkynyl, alkoxy, aryl, alkaryl, arylalkyl, heteroalkyl, heteroaryl, heterocycloalkyl, cyano, nitro, or azido, wherein $R^A$ is alkyl;

n is an integer from 0 to 4;

m is an integer from 0 to 3;

p is an integer from 0 to 6; and q is an integer from 0 to 5; and

L is:

wherein:

SP is a spacer;

is one or more bonds to the binding agent;

$AA^1$ is an amino acid; and $AA^2$ is an amino acid.

In some embodiments,

A is:

wherein:

$R^1$, independently at each occurrence, is $C_{1-6}$ alkyl, $C_{1-6}$ alkoxy, $C_{1-6}$ haloalkyl, $C_{1-6}$ haloalkoxy, or halo;

n is an integer from 0 to 4;

m is an integer from 0 to 3;

p is an integer from 0 to 6; and q is an integer from 0 to 5; and

L is:

wherein:

SP is a spacer;

is one or more bonds to the binding agent;

$AA^1$ is an amino acid; and $AA^2$ is an amino acid.

In some embodiments,

A is:

wherein:

$R^1$, independently at each occurrence, is halo, haloalkyl, haloalkoxy, alkyl, alkenyl, alkynyl, alkoxy, aryl, alkaryl, arylalkyl, heteroalkyl, heteroaryl, heterocycloalkyl, cyano, nitro, or azido, wherein $R^A$ is alkyl;

m is an integer from 0 to 3;

p is an integer from 0 to 6; and q is an integer from 0 to 5; and

L is:

61 wherein:

SP is:

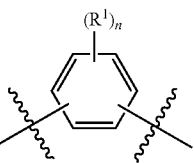

,

, or wherein:

is a bond to the binding agent; and b is an integer from 2 to 8; and

AA$^1$ is an amino acid; and

AA$^2$ is an amino acid.

In some embodiments, wherein:

A is:

R$^1$, independently at each occurrence, is selected from alkyl, alkoxy, halo, haloalkyl, and heterocycloalkyl;

n is an integer from 0 to 4; and

L is:

—SP—AA$^1$—AA$^2$—

62 wherein:

SP is a spacer;

is one or more bonds to the binding agent;

AA$^1$ is an amino acid; and

AA$^2$ is an amino acid.

In some embodiments, wherein:

A is:

R$^1$, independently at each occurrence, is selected from alkyl, alkoxy, halo, haloalkyl, and heterocycloalkyl;

n is an integer from 0 to 4; and

L is:

—SP—

40 wherein:

SP is a spacer; and

50 is one or more bonds to the binding agent.

In some embodiments,

A is:

60 wherein

R$^1$ is, independently at each occurrence, is C$_{1-6}$ alkyl, C$_{1-6}$ alkoxy, C$_{1-6}$ haloalkyl, C$_{1-6}$ haloalkoxy, halo, or heterocycloalkyl; and

63

64 n is 0, 1, or 2; and
L is:

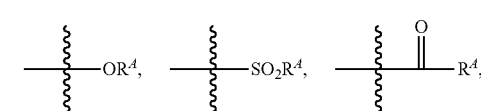

wherein:
SP is a spacer;

is the one or more bonds to the binding agent;
$R^{AA1}$ is an amino acid side chain; and
$R^{AA2}$ is an amino acid side chain.
In some embodiments, A is:

wherein:
R$^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, or azido,
wherein R$^A$ is alkyl;
wherein n is an integer from 0 to 4;
L is:

wherein:
SP is a spacer;

is the one or more bonds to the binding agent;
$R^{AA1}$ is an amino acid side chain; and
$R^{AA2}$ is an amino acid side chain.
In some embodiments,
A is:

wherein
R$^1$ is, independently at each occurrence, is halo; and
n is 0, 1, or 2; and
L is:

wherein:

is a bond to the binding agent; and
b is an integer from 2 to 8.
In some embodiments A is:

wherein:
R$^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, or azido,
wherein $R^A$ is alkyl;

L is:

wherein:

is a bond to the binding agent;
wherein n is an integer from 0 to 4; and
b is an integer from 2 to 8.
In some embodiments,
A is:

wherein
$R^1$ is, independently at each occurrence, is halo; and
n is 0, 1, or 2; and
L is:

wherein is a bond to the binding agent.

In some embodiments, A is:

wherein:

$R^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, or azido,
wherein $R^A$ is alkyl;

wherein n is an integer from 0 to 4;

L is:

or wherein is a bond to the binding agent.

In some embodiments,
A is:

and
L is or

In some embodiments, A is:

wherein:
R$^1$ is, independently at each occurrence, a hydrogen atom, alkyl, alkoxy, aryl, heteroalkyl, halo, haloalkoxy, or haloalkyl;

is the bond to the nitrogen atom of the amino-ester which is directly bonded to the drug molecule; and is the bond to the nitrogen atom which is bonded to the linker. In some embodiments, R$^1$ is 1-methylethyl-thiol, phenyl, 2-fluorophenyl, pyridinyl, 4-pyridinyl, pyrrolidinyl, or 1-pyrrolidinyl. In some embodiments, R$^1$ is trifluoromethyl. In some embodiments, R$^1$ is methyl. In some embodiments, R$^1$ is methoxy. In some embodiments, R$^1$ is fluoro. In some embodiments, R$^1$ is chloro. In some embodiments, R$^1$ is bromo. In some embodiments, R$^1$ is hydrogen.

In some embodiments, A is:

wherein:
R$^1$ is, independently at each occurrence, a hydrogen atom, alkyl, alkoxy, aryl, heteroalkyl, halo, haloalkyl, haloalkoxy;

is the bond to the nitrogen atom of the amino-ester which is directly bonded to the drug molecule; and is the bond to the nitrogen atom which is bonded to the linker. In some embodiments, R$^1$ is 1-methylethyl-thiol, phenyl, 2-fluorophenyl, pyridinyl, 4-pyridinyl, pyrrolidinyl, or 1-pyrrolidinyl. In some embodiments, R$^1$ is trifluoromethyl. In some embodiments, R$^1$ is methyl. In some embodiments, R$^1$ is methoxy. In some embodiments, R$^1$ is fluoro. In some embodiments, R$^1$ is chloro. In some embodiments, R$^1$ is bromo. In some embodiments, R$^1$ is hydrogen.

In some embodiments,
A is:

69

70

-continued and
L is or and
L is

In some embodiments,
BA is an antibody,
A is:

or

In some embodiments, A is:

wherein
R¹ is, independently at each occurrence, is halo; and
n is 0, 1, or 2; and
L is:

or

-continued wherein is a bond to the binding agent.

In some embodiments, including any of the foregoing, A is:

wherein:

$R^1$, independently at each occurrence, is selected from alkyl, alkoxy, halo, haloalkyl, and heterocycloalkyl; and n is an integer from 0 to 4.

In some embodiments, including any of the foregoing, A is:

are as defined above.

In some embodiments, including any of the foregoing, A is:

are as defined above.

In some embodiments, including any of the foregoing, A is:

are as defined above.

In some embodiments, including any of the foregoing, A is:

are as defined above.

In some embodiments, including any of the foregoing, A is:

;

and are as defined above.

In some embodiments, including any of the foregoing, A is:

;

and are as defined above.

In some embodiments, A is:

;

and are as defined above.

In some embodiments, A is:

;

and are as defined above.

In some embodiments, including an of the foregoing, A is:

;

and are as defined above.

In some embodiments, including any of the foregoing, A is:

;

and are as defined above.

In some embodiments, including any of the foregoing, A is:

;

and are as defined above.

In some embodiments, including an of the foregoing, A is:

;

and are as defined above.

In some embodiments, including any of the foregoing, A is:

.

In some embodiments, including any of the foregoing, A is:

, wherein n is 0, 1 2, or 3.

In some embodiments,

A is:

;

wherein $R^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, or azido; and q is an integer from 0 to 5; and L is:

wherein:

SP is a spacer;

is the one or more bonds to the binding agent;

$R^{AA1}$ is an amino acid side chain; and $R^{AA2}$ is an amino acid side chain.

In some embodiments, A is:

,

77

-continued $(R^1)q$

, or $(R^1)q$

;

wherein:

R$^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, —OR$^A$,    —SO$_2$R$^A$,    $\overset{O}{\underset{}{}}$—R$^A$, or azido;

wherein q is an integer from 0 to 5;

L is:

wherein:

SP is a spacer;

is the one or more bonds to the binding agent;

R$^{AA1}$ is an amino acid side chain; and

R$^{AA2}$ is an amino acid side chain.

In some embodiments,

A is:

$(R^1)q$

,

78

-continued $(R^1)q$

, or $(R^1)q$

;

wherein:

R$^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, —OR$^A$,    —SO$_2$R$^A$,    $\overset{O}{\underset{}{}}$—R$^A$, or azido;

wherein q is an integer from 0 to 5; and

L is:

wherein:

is a bond to the binding agent; and b is an integer from 2 to 8.

In some embodiments,
A is:

wherein is a bond to the binding agent.

In some embodiments, A is:

wherein:

R$^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, or azido; and
q is an integer from 0 to 5; and
L is:

wherein:

R$^1$, independently at each occurrence, is halo, haloalkoxy, haloalkyl, alkyl, alkenyl, alkynyl, alkoxy, aryl, alkaryl, arylalkyl, heteroaryl, heteroalkyl, heterocycloalkyl, cyano, nitro, or azido;
wherein q is an integer from 0 to 5;
L is:

or or or

81

-continued wherein is a bond to the binding agent.

In some embodiments,

A is:

, or

;

and

L is or

82

-continued

In some embodiments, the compound of Formula I is:

wherein A is arylene or heteroarylene, $L^1$ and $L^2$ are linkers, BA is a binding agent, k is an integer from 0 to 30, and t is an integer from 0 to 8. In some of these embodiments, $L^1$ is a linker which binds to the BA through a lysine residue. In some of these embodiments, the subscript, k, represents the number of linkers, $L^1$, bonded to the BA through lysine residues on the BA. In some of these embodiments, $L^2$ is a linker which binds to the BA through a cysteine residue. In some of these embodiments, the subscript, t, represents the number of linkers, $L^2$, bonded to the BA through cysteine residues on the BA. In some embodiments, when the linker, $L^2$, is a monodentate linker, t is an integer from 0 to 8. In some embodiments, when the linker, $L^2$, is a bidentate linker, t is an integer from 0 to 4. In some of these examples, the sum of k+t is equal to 1-8.

In some embodiments, the compound of Formula I is:

wherein A is arylene or heteroarylene, L$^1$ and L$^2$ are linkers, and BA is a binding agent. In some of these embodiments, L$^1$ is a linker which binds to the BA through a lysine residue. In some of these embodiments, L$^2$ is a linker which binds to the BA through a cysteine residue.

In some embodiments,

A is:

wherein:

R$^1$, independently at each occurrence, is halo, haloalkyl, haloalkoxy, alkyl, alkenyl, alkynyl, alkoxy, aryl, alkaryl, arylalkyl, heteroalkyl, heteroaryl, heterocycloalkyl, cyano, nitro, or azido, wherein R$^A$ is alkyl;

m is an integer from 0 to 3;

p is an integer from 0 to 6; and q is an integer from 0 to 5;

L is or

In some embodiments, the compound of Formula I is:

-continued wherein A is arylene or heteroarylene, $L^1$ and $L^2$ are linkers, BA is a binding agent, k is an integer from 0 to 30, and t is an integer from 0 to 8. In some of these embodiments, $L^1$ is a linker which binds to the BA through a lysine residue. In some of these embodiments, the subscript, k, represents the number of linkers, $L^1$, bonded to the BA through lysine residues on the BA. In some of these embodiments, $L^2$ is a linker which binds to the BA through a cysteine residue. In some of these embodiments, the subscript, t, represents the number of linkers, $L^2$, bonded to the BA through cysteine residues on the BA. In some embodiments, when the linker, $L^2$, is a monodentate linker, t is an integer from 0 to 8. In some embodiments, when the linker, $L^2$, is a bidentate linker, t is an integer from 0 to 4. In some of these examples, the sum of k+t is equal to 1-8.

In some embodiments, the compound of Formula I is:

wherein A is arylene or heteroarylene, $L^1$ and $L^2$ are linkers, and BA is a binding agent. In some of these embodiments, $L^1$ is a linker which binds to the BA through a lysine residue. In some of these embodiments, $L^2$ is a linker which binds to the BA through a cysteine residue.

In some embodiments, the compound of Formula I is:

wherein A is arylene or heteroarylene, $L^1$ and $L^2$ are linkers, and BA is a binding agent. In some of these embodiments, $L^1$ is a linker which binds to the BA through a lysine residue. In some of these embodiments, $L^2$ is a linker which binds to the BA through a cysteine residue.

In some embodiments,

A is:

wherein:

$R^1$, independently at each occurrence, is halo, haloalkyl, haloalkoxy, alkyl, alkenyl, alkynyl, alkoxy, aryl, alkaryl, arylalkyl, heteroalkyl, heteroaryl, heterocycloalkyl, cyano, nitro, 87                                                              88 or azido, wherein $R^A$ is alkyl;

n is an integer from 0 to 4;

m is an integer from 0 to 3;

p is an integer from 0 to 6; and q is an integer from 0 to 5;

L is wherein A is arylene or heteroarylene, $L^1$, $L^2$, and $L^3$ are linkers, BA is a binding agent, k is an integer from 0 to 30, t is an integer from 0 to 8, and g is an integer from 0 to 4. In some of these embodiments, $L^1$ is a linker which binds to the BA through a lysine residue. In some of these embodiments, the subscript, k, represents the number of linkers, $L^1$, bonded to the BA through lysine residues on the BA. In some of these embodiments, $L^2$ is a linker which binds to the BA through a cysteine residue. In some of these embodiments, the subscript, t, represents the number of linkers, $L^2$, bonded to the BA through cysteine residues on the BA. In some embodiments, when the linker, $L^2$, is a monodentate linker, t is an integer from 0 to 8. In some embodiments, when the linker, $L^2$, is a bidentate linker, t is an integer from 0 to 4. In some of these examples, the sum of k+t is equal to 1-8. In some of these embodiments, $L^3$ is a linker which binds to the BA through a glutamine residue. In some of these embodiments, the subscript, g, represents the number of linkers, $L^3$, bonded to the BA through glutamine residues on the BA.

In some embodiments, the compound of Formula I is:

wherein A is arylene or heteroarylene, $L^1$, $L^2$, and $L^3$ are linkers, and BA is a binding agent. In some of these embodiments, $L^1$ is a linker which binds to the BA through a lysine residue. In some of these embodiments, $L^2$ is a linker which binds to the BA through a cysteine residue. In some of these embodiments, $L^3$ is a linker which binds to the BA through a glutamine residue.

In some embodiments, A is:

90

-continued wherein:
R¹ is, independently at each occurrence, halo, haloalkyl, haloalkoxy, alkyl, alkenyl, alkynyl, alkoxy, haloalkoxy, aryl, alkaryl, arylalkyl, heteroaryl, heteroalkyl, heterocycloalkyl, cyano, nitro, or azido,
wherein $R^A$ is alkyl;
n is an integer from 0 to 4;
m is an integer from 0 to 3;
p is an integer from 0 to 6; and
q is an integer from 0 to 5.
In some embodiments, the linker is:

wherein:
SP is a spacer;

is one or more bonds to the binding agent;
$AA^1$ is an amino acid; and
$AA^2$ is an amino acid.
The spacer is a divalent moiety that connects the $AA^1$-$AA^2$ moiety to the binding agent (BA). Suitable spacers include, but are not limited to, those comprising alkylene or polyethylene glycol. The ends of the spacers, i.e., the portion of the spacer directly bonded to the binding agent or $AA^1$, can be moieties derived from reactive moieties that are used for purposes of coupling the antibody or $AA^1$ to the spacer during the chemical synthesis of the conjugate.
In some embodiments, the spacer comprises an alkylene. In some embodiments, the spacer comprises a $C_{5-7}$ alkylene. In some embodiments, the spacer is:

-continued

, or wherein:

is a bond to the binding agent; and b is an integer from 2 to 8.

In some embodiments, the spacer is:

,

, or

.

wherein:

is a bond to the binding agent.

In some embodiments, the spacer is:

,

, or wherein:

$R^N$ is a hydrogen atom or alkyl;

$R^M$ is alkyl;

the two bonds represented by are bonds to cysteines of a binding agent; and b is an integer from 2 to 8.

In some embodiments, the spacer is:

wherein:

is a bond to the binding agent; and b is an integer from 2 to 8.

In some embodiments, the spacer is:

,

-continued

, or

.

wherein:

is a bond to the binding agent.

In some embodiments, the spacer is:

wherein:

is a bond to the binding agent; and g is an integer from 2 to 20. In some embodiments, g is 2-8. In some embodiments, g is 2, 4, 6, or 8.

In some embodiments, the spacer is:

In some embodiments, the spacer is:

In some embodiments, the spacer is:

.

In some embodiments, the spacer is:

.

In some embodiments, the spacer is:

.

In some embodiments, the spacer is:

.

In some embodiments, the spacer is:

.

In some embodiments, the spacer is:

In some embodiments, the spacer is:

wherein is a bond to the binding agent;

X is N or O; $R^N$ and $R^M$ are each, independently, hydrogen or alkyl; and b is an integer from 1 to 8.

In some embodiments, $AA^1$-$AA^2$ is: valine-citrulline, citrulline-valine, lysine-phenylalanine, phenylalanine-lysine, valine-asparagine, asparagine-valine, asparagine-threonine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine, valine-alanine, alanine-valine, valine-glycine, or glycine-valine.

In some embodiments, $AA^1$-$AA^2$ is: valine-citrulline or citrulline-valine. In some embodiments, $AA^1$-$AA^2$ is: valine-citrulline.

In some embodiments, the compound of Formula I is:

or wherein X is N or O, $R^N$ and $R^M$ are each, independently, hydrogen or aryl, b is an integer from 1 to 8, A is aryl or heteroaryl, and t is an integer from 1-8.

In some embodiments, the compound of Formula I is:

99

100

-continued

101
102

103

104

-continued 107                                                                                                          108

-continued 111                                                                                                112

113                                                                                          114

-continued 115                                    116

117

118

-continued 119                                                                120

121                                                                                 122

123

124

125                                                      126

-continued 127                                                                                   128

-continued

129

130

131 132

133                                134

-continued

-continued

137                                                    138

-continued

-continued 141
142

-continued

-continued

145                                                                                           146

147

148

149

150

151

152

-continued

153                                                                154

155                                                          156

-continued

157                                                                                             158

159 160

-continued

,

;

,

,

-continued

, and wherein:

Ab is an antibody;

___S___ is a bond to a cysteine of the antibody;

___N___ is a bond to a lysine of the antibody;

k is an integer from 1 to 30; and t is an integer from 1 to 8. In some examples, k is an integer from 1 to 8. In some examples, t is an integer from 1 to 4. In some examples, when ___S___ is a bond to a cysteine of the antibody, up to 8 conjugates set forth herein may be bonded to the antibody. In some examples, when ___N___ is a bond to a lysine of the antibody, up to 30 conjugates set forth herein may be bonded to the antibody.

In some embodiment, k is an integer from 1 to 30. In some embodiment, k is an integer from 1 to 8. In some embodiment, k is an integer from 1 to 6. In some embodiments, k is an integer from 1 to 4. In some embodiments, k is an integer from 1 to 3. In some embodiments, the drug-antibody ratio (DAR) of the conjugate is from 1 to 30.

C. Compounds

Provided herein are compounds of Formula (II):

(II)

or a pharmaceutically acceptable salt thereof, wherein A is arylene or heteroarylene.

In certain embodiments, these compounds represent the payload portion of the conjugates described herein and are released, e.g., by enzyme proteolysis, following internalization of the conjugate into a cell. The methods provided herein include methods of treating a proliferative disease, e.g., cancer, comprising administering to a patient a therapeutically effective amount of a conjugate, e.g., antibody-drug conjugate that releases a compound of Formula (II) following internalization of said conjugate into a cell in said patient.

In some embodiments, these compounds represent the metabolic product of the conjugates described herein, e.g., enzyme proteolysis product. In some embodiments, these compounds represent the catabolic product of the conjugates described herein. In some embodiments, these compounds represent the cellular product of the conjugates described herein.

In some embodiments, A is a divalent radical of benzene, of pyridine, of naphthalene, or of quinolone, which are optionally substituted.

In some embodiments, A is arylene.

In some embodiments, A is:

wherein:

R$^1$, independently at each occurrence, is halo, haloalkyl, haloalkoxy, alkyl, alkenyl, alkynyl, alkoxy, aryl, alkaryl, arylalkyl, heteroaryl, heteroalkyl, heterocycloalkyl, cyano, nitro, amino, or azido, wherein R$^A$ is alkyl;

n is an integer from 0 to 4;

m is and integer from 0 to 3;

p is an integer from 0 to 6; and q is an integer from 0 to 5.

In some embodiments, the compound of Formula (II) is a compound having the Formula:

wherein R$^1$ and n are as defined herein.

In some embodiments, the compound of Formula (II) is a compound of the Formula (IIA):

(IIA)

wherein R$^1$ and n are as defined herein. In some embodiments, R$^1$ is alkyl, alkoxy, haloalkyl, or halo. In some embodiments, R$^1$ is methyl, trifluoromethyl, methoxy, fluoro, chloro, or bromo. In some embodiments, R$^1$ is methyl. In some embodiments, R$^1$ is methoxy. In some embodiments, R$^1$ is trifluoromethyl. In some embodiments, R$^1$ is fluoro. In some embodiments, R$^1$ is chloro. In some embodiments, R$^1$ is bromo.

In some embodiments, the compound of Formula (II) is a compound of the Formula (IIB):

(IIB)

wherein $R^1$ and q are as defined herein.

In some embodiments, the compound of Formula (II) is a compound of the Formula (IIB2):

(IIB2)

wherein $R^1$ and q are as defined herein.

In some embodiments, the compound of Formula (II) is a compound of the Formula (IIB3):

(IIB3)

wherein $R^1$ and q are as defined herein.

In some embodiments, the compound of Formula (II) is a compound of the Formula (IIC):

(IIC)

wherein $R^1$ and q are as defined herein.

In some embodiments, the compound of Formula (II) is a compound of the Formula (IID):

(IID)

wherein $R^1$ and q are as defined herein.

In some embodiments, the compound of Formula (II) is a compound of the Formula (IIE):

(IIE)

wherein $R^1$ and q are as defined herein.

In some embodiments, the compound of Formula (II) is a compound of the Formula (IIF):

(IIF)

wherein $R^1$ and q are as defined herein.

In some embodiments, the compound of Formula (II) is a compound of the Formula (IIG):

(IIG)

wherein $R^1$ and q are as defined herein.

In some embodiments, $R^1$ is, independently, alkyl or halo. In some embodiments, $R^1$ is, independently, $C_{1-6}$ alkyl, $C_{1-6}$ haloalkyl, or halo. In some embodiments, $R^1$ is, independently, $C_{1-4}$ haloalkyl or halo. In some embodiments, $R^1$ is, independently, halo. In some embodiments, $R^1$ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, $R^1$ is, independently, alkyl, alkoxy, heteroalkyl, halo, haloalkyl, or haloalkoxy. In some embodiments, $R^1$ is, independently, $C_{1-6}$ alkyl, $C_{1-6}$ alkoxy, $C_{1-6}$ haloalkyl, $C_{1-6}$ haloalkoxy, or halo. In some embodiments, $R^1$ is, independently, $C_{1-6}$ alkyl or $C_{1-6}$ alkoxy. In some embodiments, $R^1$ is, independently, alkoxy. In some embodiments, $R^1$ is, independently, methoxy, ethoxy, propoxy. In some embodiments, n, m, p, or q is 0, 1 or 2. In some embodiments, n, m, p, or q is 0 or 1. In some embodiments, n, m, p, or q is 0.

In some embodiments, the compound of Formula (II) is a compound of Formula (IIA):

(IIA)

wherein:

$R^1$ is, independently at each occurrence, halo, methyl, methoxy, or trifluoromethyl; and n is 0, 1, or 2. In some embodiments, $R^1$ is alkyl, alkoxy, haloalkyl, or halo. In some embodiments, $R^1$ is methyl, trifluoromethyl, methoxy, fluoro, chloro, or bromo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is chloro. In some embodiments, $R^1$ is bromo. In some examples, $R^1$ is heterocycloalkyl. In some examples, $R^1$ is pyrrolidinyl. In some examples, $R^1$ is morpholinyl.

A compound of Formula IIA1-3:

(IIA1-3)

or a pharmaceutically acceptable salt thereof, wherein:

A is:

$R^1$, independently at each occurrence, is selected from alkyl, alkoxy, halo, haloalkyl, and heterocycloalkyl; ann is an integer from 0 to 4.

In some embodiments, the compound is selected from a compound of the Formula (IIA1), a compound of the Formula (IIA2), and a compound of the Formula (IIA3):

(IIA1)

(IIA2)

(IIA3)

In some embodiments, the compound of Formula II is:

(II)

wherein A is:

$(R^1)_n$ and wherein n is 0, 1 or 2.

In some embodiments, $R^1$ is independently at each occurrence, selected from $C_{1-6}$ alkyl, $C_{1-6}$ alkoxy, halo, $C_{1-6}$ haloalkyl, and heterocycloalkyl.

In some embodiments, $R^1$ is, independently at each occurrence, selected from methyl, methoxy, fluoro, chloro, bromo, trifluoromethyl, pyrrolidinyl, and morpholinyl.

In some embodiments, $R^1$ is methyl.

In some embodiments, $R^1$, independently at each occurrence, is selected from fluoro, chloro, and bromo.

In some embodiments, $R^1$ is chloro.

In some embodiments, $R^1$ is trifluoromethyl.

In some embodiments, $R^1$ is methoxy.

In some embodiments, $R^1$ is, independently at each occurrence, selected from methyl, morpholinyl, and pyrrolidinyl.

In some embodiments, the compound of Formula (II) is a compound of Formula (IIB):

(IIB)

wherein:

$R^1$ is, independently at each occurrence, halo or trifluoromethyl; and q is 0, 1, or 2.

In some embodiments the compound of Formula (II) is:

172

173

-continued

174

-continued

175

176

177

-continued

178

-continued

and

In some embodiments, the compound of Formula (II) is:

179

180

-continued

In certain embodiments, these compounds represent the payload portion of the conjugates described herein and are released, e.g., by enzyme proteolysis, following internalization of the conjugate into a cell. The methods provided herein include methods of treating a proliferative disease, e.g., cancer, comprising administering to a patient a therapeutically effective amount of a conjugate, e.g., antibody-drug conjugate that releases a compound of Formula (II) following internalization of said conjugate into a cell in said patient.

In some embodiments, these compounds represent the metabolic product of the conjugates described herein, e.g., enzyme proteolysis product.

In some embodiments, A is a divalent radical of benzene, of pyridine, of naphthalene, or of quinolone, which are optionally substituted.

In some embodiments, A is arylene.

In some embodiments, A is:

wherein:

$R^1$ is, independently at each occurrence, alkyl, alkenyl, alkynyl, aryl, alkaryl, arylalkyl, halo, haloalkoxy, heteroaryl, heterocycloalkyl, cyano, nitro, or azido, wherein $R^A$ is alkyl;

n is an integer from 0 to 4;

m is and integer from 0 to 3;

p is an integer from 0 to 6; and q is an integer from 0 to 5.

In some embodiments, the compound of Formula (II) is a compound of the Formula (IIA):

(IIA)

wherein $R^1$ is, independently at each occurrence, methyl, methoxy, halo or trifluoromethyl; and n is 0, 1, or 2. In some embodiments, $R^1$ is methyl, trifluoromethyl, methoxy, fluoro, chloro, or bromo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is chloro. In some embodiments, $R^1$ is bromo.

In some embodiments, the compound of Formula (II) is a compound of the Formula (IIB):

(IIB)

wherein $R^1$ is, independently at each occurrence, methoxy, methyl, halo or trifluoromethyl; and q is 0, 1, or 2.

In some embodiments, the compound of Formula (II) is a compound of the Formula (IIB2):

(IIB2)

wherein $R^1$ is, independently at each occurrence, methoxy, halo or trifluoromethyl; and q is 0, 1, or 2.

In some embodiments, the compound of Formula (II) is a compound of the Formula (IIB3):

(IIB3)

wherein $R^1$ is, independently at each occurrence, methoxy, halo or trifluoromethyl; and q is 0, 1, or 2. In some embodiments, $R^1$ is, independently, alkyl or halo. In some embodiments, $R^1$ is, independently, $C_{1-6}$ alkyl, $C_{1-6}$ haloalkyl, or halo. In some embodiments, $R^1$ is, independently, $C_{1-6}$ haloalkyl or halo. In some embodiments, $R^1$ is, independently, halo. In some embodiments, $R^1$ is, independently, fluoro, chloro, bromo, iodo, or trifluoromethyl. In some embodiments, n, m, p, or q is 0, 1 or 2. In some embodiments, n, m, p, or q is 0 or 1. In some embodiments, n, m, p, or q is 0.

In some embodiments, $R^1$ is, independently, alkyl, alkoxy, heteroalkyl, halo, haloalkyl, or haloalkoxy. In some embodiments, $R^1$ is, independently, $C_{1-6}$ alkyl, $C_{1-6}$ alkoxy, $C_{1-6}$ haloalkyl, $C_{1-6}$ haloalkoxy, or halo. In some embodiments, $R^1$ is, independently, $C_{1-6}$ alkyl or $C_{1-6}$ alkoxy. In some embodiments, $R^1$ is, independently, alkoxy. In some embodiments, $R^1$ is, independently, methoxy, ethoxy, propoxy. In some embodiments, n, m, p, or q is 0, 1 or 2. In some embodiments, n, m, p, or q is 0 or 1. In some embodiments, n, m, p, or q is 0.

In some embodiments, provided herein are compounds which include any of the compounds described herein covalently bonded to a linker and/or binding agent as described herein. In some examples, provided herein are any of the maytansinoid compounds described herein covalently bonded to a linker and/or binding agent as described herein.

D. Preparation of Compounds

Compounds of Formula I can be synthesized by coupling compounds of Formula P1 with a binding agent, e.g., antibody under standard conjugation conditions (see, e.g., Doronina et al., *Nature Biotechnology* 2003, 21, 7, 778, which is incorporated herein by reference). When the binding agent is an antibody, the antibody can be coupled to a compound of Formula P1 via one or more cysteine or lysine residues of the antibody. Compounds of Formula P1 can be coupled to cysteine residues, for example, by subjecting the antibody to a reducing agent, e.g., dithiotheritol, to cleave the disulfide bonds of the antibody, purifying the reduced antibody, e.g., by gel filtration, and subsequently reacting the antibody with a compound of formula P1 containing a reactive moiety, e.g., a maleimido group. Suitable solvents include, but are not limited to water, DMA, DMF, and DMSO. Compounds of formula P1 containing a reactive moiety, e.g., activated ester or acid halide group, can be coupled to lysine residues. Suitable solvents include, but are not limited to water, DMA, DMF, and DMSO. The compounds of Formula I can be purified using known protein techniques, including, for example, size exclusion chromatography, dialysis, and ultrafiltration/diafiltration.

P1

I wherein RL is a reactive linker, A is arylene or heteroarylene, L is a linker, and BA is a binding agent.

In some examples, set forth herein are methods of making a compound of Formula (I) wherein the method includes contacting a compound of Formula P1 with a binding agent. In some of these methods, the contacting is under standard antibody conjugation conditions. In some of these examples, the binding agent is an antibody. In some of these examples, the binding agent is a fragment of an antibody. In some examples herein, the methods include contacting a compound of Formula P1 with one or more cysteine or lysine residues of an antibody. In some examples herein, the methods include contacting a compound of Formula P1 with one or more cysteine or lysine residues of an antibody in a solvent. In some embodiments, the solvent is a single compound. In some embodiments, the solvent is a mixture of two or more compounds. In some examples, the methods include contacting a compound of Formula P1 with one or more cysteine or lysine residues of an antibody in a solvent selected from water, DMA, DMF, or DMSO.

In some examples, set forth herein are methods of making a compound of Formula P1, wherein the methods include reacting a compound of Formula (II) with a reactive linker (RL), wherein RL is a reactive linker as set forth and described herein.

(II)

RL ⟶

P1

In some examples, set forth herein are methods of making a compound of Formula P1, wherein the methods include reacting a compound of Formula (II) with a reactive linker set forth and described herein. In some examples, the methods include reacting a compound of Formula P1 with a RL in the presence of a solvent. In some examples, the solvent is DCM. In some other examples, the solvent is methanol. In some other examples, the solvent is anhydrous methanol. In certain other examples, the solvent is a combination of DCM and methanol. In some other examples, the solvent is a combination of DCM and anhydrous methanol.

In some examples, the RL is selected from a compound of Formula PP7

PP7 wherein $SP^R$ is a reactive spacer; $R^{AA1}$ is an amino acid side chain; $R^{AA2}$ is an amino acid side chain. In some examples, $R^{AA1}$ and $R^{AA2}$ are independently natural or non-natural amino acid side chains. In some examples of the methods of making a compound of Formula P1, the methods include reacting a compound of Formula (II) with a compound of Formula PP7 under amide synthesis conditions. In some of these examples, the compound of Formula PP7 is converted into an activated ester before reacting with a compound of Formula (II).

In some examples of the methods of making a compound of Formula P1, the methods include contacting a compound of Formula (II) with a RL. In some these examples, the methods include contacting a compound of Formula (II) with a RL under amide synthesis conditions. In some examples, the RL includes a carboxylic acid group at one terminal end of the RL compound. As shown in Formula (II), a compound of Formula (II) includes at least one amino group at one terminal end of the compound. In some examples, the methods include converting a carboxylic acid group of the RL compound into an activated ester. In some examples, the methods further include reacting this activated ester with an amino group on a compound of Formula (II). In some examples herein, the methods of converting the carboxylic acid into an activated ester include contacting the carboxylic acid with a reagent. In some examples herein, the methods of converting the carboxylic acid of the RL into an activated ester include contacting the RL with a reagent selected from dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), 2-Ethoxy-1-ethoxycarbonyl-1,2-dihydroquinoline (EEDQ), 1-Ethyl-3-(3-dimethylaminopropyl)carbodiimide (EDC), 2-Chloro-1,3-dimethylimidazolidinium hexafluorophosphate (CIP), 2-chloro-4,6-dimethoxy-1,3,5-triazine (CDMT), or carbonyldiimidazole (CDI). In some examples, the methods include, converting a carboxylic acid group of the RL compound into an acyl chloride. In some examples, the methods include converting a carboxylic acid group of the RL compound into an acyl chloride, for example by contacting the carboxylic acid of the RL with EEDQ. In some examples herein, the carboxylic acid of the RL is converted into a mixed anhydride, for example by contacting the carboxylic acid of the RL with EEDQ. In some examples herein, the methods of converting the carboxylic acid of the RL into a mixed anhydride include contacting a carboxylic acid of the RL with EEDQ. In some examples herein, the methods of converting a carboxylic acid of the RL into a mixed anhydride include contacting a carboxylic acid of the RL with EEDQ in a solvent selected from DCM.

In some examples, set forth herein are methods of making a compound of Formula P1, wherein the methods include reacting a compound of Formula (II) with a RL wherein the RL is 6-maleimidyl-caproamidyl-L-valine-L-citrulline. In some examples, the 6-maleimidyl-caproamidyl-L-citrulline is activated to form an activated ester before reacting with a compound of Formula (II). In some examples, the methods herein include providing 6-maleimidyl-caproamidyl-L-valine-L-citrulline by reacting BOC-protected L-valine-L-citrulline with 2-(2-amino-3-methyl-butyrylamino)-5-ureido-pentanoic acid and 6-(2,5-Dioxo-2,5-dihydro-pyrrol-1-yl)-hexanoic acid 2,5-dioxo-pyrrolidin-1-yl ester. In some methods herein, the methods include providing 6-maleimidyl-caproamidyl-L-valine-L-citrulline by reacting BOC-protected L-valine-L-citrulline with 2-(2-amino-3-methyl-butyrylamino)-5-ureido-pentanoic acid and 6-(2,5-dioxo-2,5-dihydro-pyrrol-1-yl)-hexanoic acid 2,5-dioxo-pyrrolidin-1-yl ester in DMF. In some methods herein, the methods include providing 6-maleimidyl-caproamidyl-L-valine-L-citrulline by reacting BOC-protected L-valine-L-citrulline with 2-(2-amino-3-methyl-butyrylamino)-5- ureido-pentanoic acid and 6-(2,5-dioxo-2,5-dihydro-pyrrol-1-yl)-hexanoic acid 2,5-dioxo-pyrrolidin-1-yl ester in DIEA.

In some examples of the methods of making a compound of Formula P1, the methods include reacting a compound of Formula (II) with adipic anhydride. In these methods, the adipic anhydride is an activated ester. In some of these examples, the methods include reacting a compound of Formula (II) with adipic anhydride and triethylamine. In some of examples, the methods include reacting a compound of Formula (II) with adipic anhydride and triethylamine in tetrahydrofuran. In some of these examples, the methods include reacting a compound of Formula (II) with adipic anhydride and triethylamine in dimethylformamide. In some of these examples, the methods include reacting a compound of Formula (II) with adipic anhydride and triethylamine in tetrahydrofuran and dimethylformamide (DMF). In some examples, these methods further include reacting N-hydroxysuccinimide with the products of the aforementioned methods. In some other of these examples, these methods further include reacting N-hydroxysuccinimide and EDC hydrochloride with the products of the aforementioned methods.

In some examples, set forth herein are methods of making a compound of Formula (II). In some examples, these methods include reacting a compound of Formula PP5 with a suitable reducing agent.

In some of these methods of making a compound of Formula (II), the suitable reducing agent includes a metal, a metal foil, a metal powder, dust of a metal, a metal amalgam, or metal filings. In certain embodiments, the metal is selected from zinc, iron, aluminum, palladium, or Raney nickel. In some of these methods, the suitable reducing agent is Zn foil, Zn powder, Zn dust, Zn amalgam, or Zn filings. In some of these methods, the suitable reducing agent is Zn foil. In some of these methods, the suitable reducing agent is Zn powder. In some of these methods, the suitable reducing agent is Zn dust. In some of these methods, the suitable reducing agent is Zn amalgam. In some of these methods, the suitable reducing agent is Zn filings. In some methods, the methods further include reducing the compound of formula PP5 in the presence of a solvent. In some examples, the solvent is acetic acid. In some examples, the solvent is tetrahydrofuran. In some examples, the solvent is a combination of acetic acid and tetrahydrofuran. In some examples, the solvent is acetonitrile. In some examples, the solvent is acetonitrile and water.

In some examples, set forth herein are methods of making a compound of Formula PP5. In some examples, these methods include reacting a compound of Formula P2 with a compound of Formula PP6.

P2

+

PP6

PP5

In some of these examples, A is arylene or heteroarylene, optionally substituted as set forth herein.

In some examples of the methods of making a compound of Formula PP5, the methods include reacting a compound of Formula P2 with a compound of Formula PP6 under Lewis acid conditions. In some examples, the compound of PP6 is a para-nitro-phenyl-isocyanate. In some examples, the compound of PP6 is a meta-nitro-phenyl-isocyanate. In some examples, the Lewis acid conditions include using a Lewis acid during the reaction of a compound of Formula P2 with a compound of Formula PP6. In some examples, a compound of Formula P2 is reacted with a compound of Formula PP6 in the presence of a Lewis Acid. Suitable Lewis acids include, but are not limed to $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl and n is from 0 to 3), $Zn(OTf)_2$, $Yb(OTf)_3$, $Sc(OTf)_3$, $MgBr_2$, $NiCl_2$, $Sn(OTf)_2$, $Ni(OTf)_2$, or $Mg(OTf)_2$. In some examples, the Lewis acid is $ZnCl_2$. In some examples, the Lewis acid conditions include using a Lewis acid and an organic solvent during the reaction of a compound of Formula P2 with a compound of Formula PP6. In some examples, a compound of Formula P2 is reacted with a compound of Formula PP6 in the presence of a Lewis Acid and an organic solvent. In some examples, the organic solvent is dichloromethane (DCM). In some examples, a compound of Formula P2 is reacted with a compound of Formula PP6 in the presence of $ZnCl_2$ and DCM. In some examples, a compound of Formula P2 is reacted with a compound of Formula PP6 in the presence of $ZnCl_2$, DCM, and diethyl ether. In some examples, a compound of Formula P2 is reacted with a compound of Formula PP6 in the presence of DCM and also a diethyl ether solution of $ZnCl_2$. In some examples, a compound of Formula P2 is reacted with a compound of Formula PP6 in the presence of DCM wherein $ZnCl_2$ is added during this reaction as a diethyl ether solution of $ZnCl_2$. In some examples, the methods herein include reacting a compound of Formula P2 with a compound of Formula PP6 under Lewis acid conditions for at least 2, 4, 6, 8, 10, 12, 14, 16, 18, 20, 22, or 24 hours. In some examples, the methods herein include reacting a compound of Formula P2 with a compound of Formula PP6 under Lewis acid conditions for 2, 4, 6, 8, 10, 12, 14, 16, 18, 20, 22, or 24 hours. In some examples, the methods herein include reacting a compound of Formula P2 with a compound of Formula PP6 under Lewis acid conditions for 16 hours. In some examples, the methods herein include reacting a compound of Formula P2 with a compound of Formula PP6 under Lewis acid conditions for 18 hours. In some examples, the methods herein include reacting a compound of Formula P2 with a compound of Formula PP6 under Lewis acid conditions for 20 hours. In some examples, the methods herein include reacting a compound of Formula P2 with a compound of Formula PP6 under Lewis acid conditions for 24 hours.

In some examples, after reacting a compound of Formula P2 with a compound of Formula PP6, the product is diluted with water and extracted once, twice, or three times with an organic solvent. In some examples the organic solvent used for this extraction is selected from ethyl acetate (EtOAc).

In some examples, after reacting a compound of Formula P2 with a compound of Formula PP6, the product is concentrated to dryness. In some examples, after reacting a compound of Formula P2 with a compound of Formula PP6, the product is concentrated to dryness and purified by chromatography In some embodiments, the compound of formula P1 includes A, wherein A is:

wherein n is 0 or 1; and $R^1$ is alkyl, alkoxy, halo, haloalkoxy, or haloalkyl.

In some embodiments, the compound of formula P1 includes A, wherein A is:

wherein n is 0 or 1; and $R^1$ is $C_{1-6}$ alkyl, $C_{1-6}$ alkoxy, halo, $C_{1-6}$ haloalkoxy, or $C_{1-6}$ haloalkyl.

In some embodiments, the compound of formula P1 includes A, wherein A is:

wherein n is 0 or 1; $R^1$ is $C_{1-6}$ alkyl, $C_{1-6}$ alkoxy, halo, $C_{1-6}$ haloalkoxy, or $C_{1-6}$ haloalkyl; and RL is wherein b is an integer from 2 to 8 and is a bond to the binding agent. In some embodiments, $R^1$ is alkyl, alkoxy, haloalkyl, or halo. In some embodiments, $R^1$ is methyl, trifluoromethyl, methoxy, fluoro, chloro, or bromo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is chloro. In some embodiments, $R^1$ is bromo.

The reactive linker is a moiety comprising a portion in its structure that is capable of reacting with the binding agent (e.g., reacting with an antibody at its cysteine or lysine residues) to form the compound of Formula I. Following conjugation to the binding agent, the reactive linker becomes the linker (L) moiety of the compound of Formula I. Illustrative reactive linkers include, but are not limited to, those that comprise haloacetyl, isothiocyanate, terminal primary amine or maleimide portions that are capable of reacting with the binding agent. Reactive portions also include moieties having the following structure:

wherein X is —O— or —NH— and LG is a leaving group, e.g., Br.

In some embodiments, the reactive linker is:

wherein:

SP$^R$ is a reactive spacer;

AA$^1$ is an amino acid; and

AA$^2$ is an amino acid.

The reactive spacer is a moiety that contains the above-described reactive linker portion that is capable of reacting with the binding agent and connects this portion to AA$^1$. Suitable spacers include, but are not limited to, those comprising alkylene or polyethylene glycol connecting the AA$^1$ to the portion capable of reacting with binding agent (e.g., haloacetyl, isothiocyanate, or maleimide).

In some embodiments, the reactive spacer is:

wherein b is an integer from 2 to 8.

In some embodiments, the reactive spacer is:

In some embodiments, the spacer is

In some embodiments, the spacer is or wherein g is an integer from 1 to 24.

In some embodiments, the reactive spacer is:

or wherein b is an integer from 2 to 8 and g is an integer from 2 to 20.

In some embodiments, the reactive spacer is:

or

In some embodiments, $AA^1$-$AA^2$ is: valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine, valine-alanine, alanine-valine, valine-glycine, or glycine-valine.

In some embodiments, $AA^1$-$AA^2$ is: valine-citrulline or citrulline-valine. In some embodiments, $AA^1$-$AA^2$ is: valine-citrulline.

In some embodiments, the reactive linker is:

wherein:

$SP^R$ is a reactive spacer;

$R^{AA1}$ is an amino acid side chain; and $R^{AA2}$ is an amino acid side chain.

In some embodiments, the reactive linker is:

wherein:

SP is a reactive spacer.

In some embodiments, the reactive linker is:

wherein b is an integer from 2 to 8.

In some embodiments, the reactive linker is:

wherein b is an integer from 2 to 8.

In some embodiments, the reactive linker is:

wherein b is an integer from 2 to 8.

In some embodiments, the reactive linker is:

wherein b is an integer from 2 to 8.

In some embodiments, the reactive linker is:

wherein b is an integer from 2 to 8, $R^N$ is a hydrogen atom or alkyl, and $R^M$ is alkyl.

In some embodiments, the reactive linker is:

wherein b is an integer form 2 to 8.

In some embodiments, the reactive linker is:

wherein b is an integer from 2 to 8.

In some embodiments, the reactive linker is:

wherein b is an integer from 2 to 8; $R^N$ is a hydrogen atom or alkyl; and $R^M$ is alkyl.

In some embodiments, the reactive linker is:

wherein b is an integer from 2 to 8.

In some embodiments the reactive linker is:

In some embodiments, the reactive linker is:

wherein g is an integer from 2 to 8.

In some embodiments, the reactive linker is:

In some embodiments, the reactive linker is:

In some embodiments, the reactive linker is:

In some embodiments, the reactive linker is:

In some embodiments, the reactive linker is:

In some embodiments, the reactive linker is:

In some embodiments, the reactive linker is:

199                                                    200

In some embodiments, the reactive linker is:

In some embodiments, the compound of Formula P1 is a
compound of Formula P1A:

P1A

In some embodiments, the reactive linker is:

SP$^R$—AA$^1$—AA$^2$—N—A—N—carbamate wherein:
      A is:

In some embodiments, the reactive linker is:

$(R^1)_n$ $(R^1)_m$

In some embodiments, the reactive linker is:

-continued $(R^1)_p$

, or

$(R^1)_q$

,

wherein:

R$^1$ is halo, haloalkoxy, haloalkyl, alkyl, alkenyl, alkynyl, alkoxy, aryl, alkaryl, arylalkyl, heteroalkyl, heteroaryl, heterocycloalkyl, cyano, nitro, or azido, wherein R$^A$ is alkyl;

n is an integer from 0 to 4;

m is an integer from 0 to 3;

p is an integer from 0 to 6; and q is an integer from 0 to 5;

SP$^R$ is a reactive spacer;

AA$^1$ is an amino acid; and

AA$^2$ is an amino acid.

In some embodiments, the compound of Formula P1A is a compound which includes A wherein A is:

wherein n is 0 or 1; and R$^1$ is alkoxy, alkyl, halo, haloalkoxy, or haloalkyl.

In some embodiments, the compound of Formula P1A is a compound which includes A wherein A is:

wherein n is 0 or 1; and R$^1$ is C$_{1-6}$ alkoxy, C$_{1-6}$ alkyl, halo, C$_{1-6}$ haloalkoxy, or C$_{1-6}$ haloalkyl. In some embodiments, R$^1$ is alkyl, alkoxy, haloalkyl, or halo. In some embodiments, R$^1$ is methyl, trifluoromethyl, methoxy, fluoro, chloro, or bromo. In some embodiments, R$^1$ is methyl. In some embodiments, R$^1$ is methoxy. In some embodiments, R$^1$ is trifluoromethyl. In some embodiments, R$^1$ is fluoro. In some embodiments, R$^1$ is chloro. In some embodiments, R$^1$ is bromo.

In some embodiments, the compound of Formula P1A is a compound which includes A wherein A is:

wherein q is an integer from 0 to 5; and R$^1$ is C$_{1-6}$ alkoxy, C$_{1-6}$ alkyl, halo, C$_{1-6}$ haloalkoxy, or C$_{1-6}$ haloalkyl.

In some embodiments, the compound of Formula P1A is a compound which includes A wherein A is:

wherein q is an integer from 0 to 5; and R$^1$ is C$_{1-6}$ alkoxy, C$_{1-6}$ alkyl, halo, C$_{1-6}$ haloalkoxy, or C$_{1-6}$ haloalkyl.

In some embodiments, the compound of Formula P1 is a compound of Formula P1A1-3:

(P1A1-3)

wherein:

A is:

R$^1$, independently at each occurrence, is selected from alkyl, alkoxy, halo, haloalkyl, and heterocycloalkyl;

n is an integer from 0 to 4; and RL is a reactive linker.

In some embodiments, the compound of Formula P1A1-3 is a compound of Formula P2A1-3:

(P2A1-3)

wherein:

A is selected from:

, and

;

and

SP$^R$ is a reactive spacer.

In some embodiments, the compound of Formula P1A1-3 is selected from a compound of Formula P1H1, a compound of Formula P1I1, a compound of Formula P1V1, a compound of Formula P1W1, a compound of Formula P1K1, a compound of Formula P1TG1, a compound of Formula P1ZZ1, and a compound of Formula P1ZZ2, wherein b is an integer from 2 to 8:

(P1H1)

-continued (P1I1)

(P1V1)

(P1W1)

(P1K1)

-continued (P1TG1)

(P1ZZ1)

and (P1ZZ2)

In some embodiments, the compound of Formula P1 is a compound of Formula P1B:

P1B wherein

A is:

or wherein:

$R^1$ is halo, haloalkoxy, haloalkyl, alkyl, alkenyl, alkynyl, alkoxy, aryl, alkaryl, arylalkyl, heteroalkyl, heteroaryl, heterocycloalkyl, cyano, nitro, or azido, wherein $R^A$ is alkyl;

n is an integer from 0 to 4;

m is an integer from 0 to 3;

p is an integer from 0 to 6; and q is an integer from 0 to 5; and $SP^R$ is a reactive spacer.

In some embodiments, the compound of Formula P1 is a compound of Formula P1C:

P1C wherein:

$SP^R$ is a reactive spacer;

$AA^1$ is an amino acid;

$AA^2$ is an amino acid;

$R^1$ is, independently at each occurrence, alkyl, alkoxy, halo, haloalkoxy, haloalkyl, or trifluoromethyl, and n is 0, 1, or 2.

In some embodiments, the compound of Formula P1 is a compound of Formula P1D:

P1D wherein:

SP$^R$ is a reactive spacer;

AA$^1$ is an amino acid;

AA$^2$ is an amino acid;

R$^1$ is, independently at each occurrence, alkyl, alkoxy, halo, haloalkoxy, haloalkyl, or trifluoromethyl, and n is 0, 1, or 2. In some embodiments, n is 0. In some embodiments, n is 1. In some embodiments, n is 2.

In some embodiments, the compound of Formula P1 is a compound of Formula P1D, wherein R$^1$ is alkoxy, alkyl, halo, haloalkoxy, or haloalkyl. In some embodiments, and R$^1$ is C$_{1-6}$ alkoxy, C$_{1-6}$ alkyl, halo, C$_{1-6}$ haloalkoxy, or C$_{1-6}$ haloalkyl. In some embodiments, n is 0. In some embodiments, n is 1. In some embodiments, n is 2.

In some embodiments, the compound of Formula P1 is a compound of Formula P1D, wherein and R$^1$ is C$_{1-6}$ alkoxy, C$_{1-6}$ alkyl, halo, C$_{1-6}$ haloalkoxy, or C$_{1-6}$ haloalkyl; and SP$^R$-AA$^1$-AA$^2$ is wherein b is an integer from 2 to 8 and is a bond to the binding agent. In some embodiments, n is 0. In some embodiments, n is 1. In some embodiments, n is 2. In some embodiments b is 2. In some embodiments b is 3. In some embodiments b is 4. In some embodiments b is 5. In some embodiments b is 6. In some embodiments b is 7. In some embodiments b is 8.

In some embodiments, the compound of Formula P1 is a compound of Formula P1E:

P1E wherein:

SP$^R$ is a reactive spacer;

R$^{AA1}$ is an amino acid side chain;

R$^{AA2}$ is an amino acid side chain;

R$^1$ is, independently at each occurrence, alkyl, alkoxy, halo, haloalkoxy, haloalkyl, or trifluoromethyl, and n is 0, 1, or 2.

In some embodiments, the compound of Formula P1 is a compound of Formula P1F:

P1F wherein:

SP$^R$ is a reactive spacer;

R$^1$ is, independently at each occurrence, alkyl, alkoxy, halo, haloalkoxy, haloalkyl, or trifluoromethyl, and n is 0, 1, or 2.

In some embodiments, the compound of Formula P1 is a compound of Formula P1G:

P1G wherein:

SP$^R$ is a reactive spacer; and

R$^1$ is a hydrogen atom, alkyl, alkoxy, halo, haloalkoxy, haloalkyl, or trifluoromethyl.

In some embodiments, the compound of Formula P1 is a compound of Formula P1H:

P1H wherein:

$R^1$ is hydrogen atom, alkyl, alkoxy, halo, haloalkoxy, haloalkyl, or trifluoromethyl; and b is an integer from 2 to 8.

In some embodiments, the compound of Formula P1 is a compound of Formula P1I:

P1I wherein:

$R^1$ is a hydrogen atom, alkyl, alkoxy, halo, haloalkoxy, haloalkyl, or trifluoromethyl; and b is an integer from 2 to 8.

In some embodiments, the compound of Formula P1 is a compound of Formula P1J:

P1J wherein:

$R^1$ is a hydrogen atom, alkyl, alkoxy, halo, haloalkoxy, haloalkyl, or trifluoromethyl; and b is an integer from 2 to 8.

In some embodiments, the compound of Formula P1 is a compound of Formula P1K:

P1K wherein $R^1$ is a hydrogen atom, alkyl, alkoxy, halo, haloalkoxy, haloalkyl, or trifluoromethyl.

In some embodiments, the compound of Formula P1 is a compound of Formula P1L:

P1L wherein R$^1$ is a hydrogen atom, alkyl, alkoxy, halo, haloalkoxy, haloalkyl, or trifluoromethyl.

In some embodiments, the compound of Formula P1 is a compound of Formula P1M:

P1M wherein R$^1$ is a hydrogen atom, alkyl, alkoxy, halo, haloalkoxy, haloalkyl, or trifluoromethyl.

In some embodiments, the compound of Formula P1 is a compound of Formula P1N:

P1N wherein R$^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1O:

P1O wherein $R^1$ is a hydrogen atom, alkyl, alkoxy, halo, haloalkoxy, haloalkyl, or trifluoromethyl.

In some embodiments, the compound of Formula P1 is a compound of Formula P1P:

P1P wherein $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1Q:

P1Q wherein $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1R:

P1R wherein $R^1$ is a hydrogen atom, alkyl, alkoxy, halo, haloalkoxy, haloalkyl, or trifluoromethyl.

In some embodiments, the compound of Formula P1 is a compound of Formula P1S:

P1S wherein $R^1$ is a hydrogen atom, alkyl, alkoxy, halo, haloalkoxy, haloalkyl, or trifluoromethyl.

In some embodiments, the compound of Formula P1 is a compound of Formula P1T:

P1T wherein $R^N$ is a hydrogen atom or alkyl, $R^M$ is alkyl, $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1U:

P1U wherein $R^N$ is a hydrogen atom or alkyl, $R^M$ is alkyl, $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1V:

P1V wherein $R^1$ is a hydrogen atom, alkyl, alkoxy, halo, haloalkoxy, haloalkyl, or trifluoromethyl, and b is an integer from 2 to 8.

In some embodiments, the compound of Formula P1 is a compound of Formula P1W:

P1W wherein $R^1$ is a hydrogen atom, alkyl, alkoxy, halo, haloalkoxy, haloalkyl, or trifluoromethyl, g is an integer from 2 to 20; and b is an integer from 2 to 8.

In some embodiments, the compound of Formula P1 is a compound of Formula P1X:

P1X

US 12,691,182 B2

227 wherein:

R$^1$ is alkyl, alkenyl, alkynyl, alkoxy, heteroalkyl, halo, haloalkyl, or haloalkoxy; and b is an integer from 2 to 8. In some embodiments, R$^1$ is methyl, ethyl, methoxy, or ethoxy. In some of these embodiments, R$^1$ is methoxy. In some embodiments, R$^1$ is 1-methylethyl-thiol, phenyl, 2-fluorophenyl, pyridinyl, 4-pyridinyl, pyrrolidinyl, or 1-pyrrolidinyl. In some embodiments, R$^1$ is trifluoromethyl. In some embodiments, R$^1$ is fluoro. In some embodiments, R$^1$ is hydrogen.

In some embodiments, the compound of Formula P1 is a compound of Formula P1Y:

P1Y wherein R$^1$ is alkyl, alkenyl, alkynyl, alkoxy, heteroalkyl, halo, haloalkyl, haloalkoxy. In some embodiments, R$^1$ is methyl, ethyl, methoxy, or ethoxy. In some of these embodiments, R$^1$ is methoxy. In some embodiments, R$^1$ is 1-methylethyl-thiol, phenyl, 2-fluorophenyl, pyridinyl, 4-pyridinyl, pyrrolidinyl, or 1-pyrrolidinyl. In some embodiments, R$^1$ is trifluoromethyl. In some embodiments, R$^1$ is fluoro. In some embodiments, R$^1$ is hydrogen.

In some embodiments, the compound of Formula P1 is a compound of Formula P1Z:

P1Z wherein R$^c$ is selected from alkyl or haloalkyl and wherein the alkyl or haloalkyl is linear, branched, or cyclic. In some embodiments, the compound of Formula P1 is a compound having one of the following structures:

229

230

231

232

-continued

233

234

-continued

235                                    236

237

238

-continued

-continued 243                                                                244

-continued 247 248

-continued

249

250

-continued

251

252

253

254

255                                          256

-continued 257                                            258

-continued

261                                                          262

263                                                                                     264

265 266

267

268

269

270

271
272

273

274

275

276

277                                                                                                      278

-continued

279                                                                          280

281

282

-continued 285                                              286

-continued

-continued

-continued

293        294

-continued

-continued

297

298

299                                                                                                 300

-continued

301

302

303

304

307                                                            308

309 310

311

312

313                                    314

315

316

-continued

317

318

-continued

321

322

-continued

In some embodiments, the compound of Formula P1 is a compound having one of the following structures:

325                                                  326

-continued

327                                                                                                                                 328

-continued

329

330

-continued

,

-continued

,

, or

.

333

Compounds of Formula (II) can be synthesized by contacting compounds of Formula PP5 with a suitable reducing agent:

PP5 wherein A is arylene or heteroarylene.

In some embodiments, the suitable reducing agent includes a metal, a metal foil, a metal powder, a dust of a metal, a metal amalgam, or metal filings. In certain embodiments, the metal is selected from zinc, iron, aluminum, palladium, or Raney nickel.

For example, in some embodiments, the following reducing agent conditions are employed. With respect to the amount of compound PP5, for example, in some of the methods herein about twenty (20) equivalents of zinc dust and forty (40) equivalents of acetic acid were combined. In some examples, the reducing reaction was conducted at room temperature for about from 1 to 24 hours. In some of these examples, the aforementioned acetic acid is substituted with another suitable mild acid or proton donor. Examples of suitable mild acids or proton donors include, but are not limited to formic acid, pTsOH, and NH$_4$Cl. In some of these examples, the reducing metal is substituted with a suitable reducing agent selected from iron, aluminum, palladium, or Raney nickel. In some of these examples, suitable solvents includes those solvents having 10-50% water (by volume) in a miscible organic solvent. Example miscible organic solvents include, but are not limited to THF, Dioxane, and diethyl ether. In some examples, the reducing reactions set forth herein are conducted at reaction temperatures which range from 0 to 50° C. In some examples, the reducing reactions set forth herein are conducted at reaction times which range from 1 to 40 hours.

Suitable acids include, but are not limited to, acetic acid.

In some embodiments, A is:

334

-continued wherein:

R$^1$ is, independently at each occurrence, alkyl, alkenyl, alkynyl, aryl, alkaryl, arylalkyl, halo, haloalkoxy, haloalkyl, heteroalkyl, heteroaryl, heterocycloalkyl, cyano, nitro, or azido, wherein R$^A$ is alkyl;

n is an integer from 0 to 4;

m is and integer from 0 to 3;

p is an integer from 0 to 6; and q is an integer from 0 to 5.

In some embodiments, the compound of Formula PP5 is a compound of the Formula PP5A:

PP5A wherein R$^1$ and n are as defined herein.

335

In some embodiments, the compound of PP5 is the a compound of Formula PP5A1:

(PP5A1)

wherein:

R¹, independently at each occurrence, selected from alkyl, alkoxy, halo, haloalkyl, and heterocycloalkyl; and n is an integer from 0 to 4.

In some embodiments, R¹ is, independently, alkyl, alkoxy, heteroalkyl, halo, haloalkyl, or haloalkoxy. In some embodiments, R¹ is, independently, $C_{1-6}$ alkyl, $C_{1-6}$ alkoxy, $C_{1-6}$ haloalkyl, $C_{1-6}$ haloalkoxy, or halo. In some embodiments, R¹ is, independently, $C_{1-6}$ alkyl or $C_{1-6}$ alkoxy. In some embodiments, R¹ is halo. In some embodiments, R¹ is, independently, alkoxy. In some embodiments, R¹ is, independently, methoxy, ethoxy, or propoxy. In some embodiments, R¹ is methyl. In some embodiments, R¹ is methoxy. In some embodiments, R¹ is trifluoromethyl. In some embodiments, R¹ is fluoro. In some embodiments, R¹ is chloro. In some embodiments, R¹ is bromo. In some embodiments, n, m, p, or q is 0, 1 or 2. In some embodiments, n, m, p, or q is 0 or 1. In some embodiments, n, m, p, or q is 0.

In some embodiments, the compound of Formula PP5 is a compound of the Formula PP5A:

PP5A wherein:

R¹ is, independently at each occurrence, halo or trifluoromethyl; and n is 0, 1, or 2.

In some embodiments, the compound of Formula PP5 is a compound of the Formula PP5A2:

PP5A2 wherein:

R¹ is, independently at each occurrence, halo or trifluoromethyl; and q is an integer from 0 to 5

In some embodiments, the compound of Formula PP5 is a compound of the Formula PP5A3:

PP5A3 wherein:

R¹ is, independently at each occurrence, halo or trifluoromethyl; and q is an integer from 0 to 5. In some embodiments, R¹ is 1-methylethyl-thiol, phenyl, 2-fluorophenyl, pyridinyl, 4-pyridinyl, pyrrolidinyl, or 1-pyrrolidinyl. In some embodiments, R¹ is trifluoromethyl. In some embodiments, R¹ is methoxy. In some embodiments, R¹ is fluoro. In some embodiments, R¹ is hydrogen.

Compounds of Formula PP5 can be synthesized by contacting compounds of Formula P2 with compounds of Formula PP6 under Lewis acid conditions:

337 338

P2

PP6

Suitable compounds of Formula PP6 include, but are not limited to, 4-isocyanato-2-methyl-1-nitro-benzene, 1-isocyanato-2-methyl-4-nitro-benzene, 2-bromo-4-isocyanato-1-nitro-benzene, 2-chloro-1-isocyanato-4-nitro-benzene, 3-chloro-1-isocyanato-4-nitro-benzene, 2-fluoro-1-isocyanato-4-nitro-benzene, 2-bromo-1-isocyanato-4-nitro-benzene, 4-isocyanato-2-methoxy-1-nitro-benzene, 1-isocyanato-2-methoxy-4-nitro-benzene, 4-isocyanato-1-nitro-2-trifluoromethyl-benzene, or 1-isocyanato-4-nitro-2-trifluoromethyl-benzene.

Suitable compounds of Formula PP6 include compounds having any one of the following formula:

wherein $R^1$ is, independently at each occurrence, $C_{1-6}$ alkyl, $C_{1-6}$ alkoxy, halo, $C_{1-6}$ haloalkyl, or $C_{1-6}$ haloalkoxy, wherein n is 0, 1, 2, 3, or 4. In certain of these embodiments, $R^1$ is methoxy or methyl. In some specific embodiments, $R^1$ is methoxy, methyl, fluoro, chloro, bromo or trifluoromethyl. In certain embodiments, n is 1 or 2. In some of these embodiments, n is 1. In some embodiments, $R^1$ is fluoro, chloro, bromo, or iodo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is chloro. In some embodiments, $R^1$ is bromo.

In some embodiments, $R^1$ is 1-methylethyl-thiol, phenyl, 2-fluorophenyl, pyridinyl, 4-pyridinyl, pyrrolidinyl, or 1-pyrrolidinyl. In some embodiments, $R^1$ is trifluoromethyl. In some embodiments, $R^1$ is methoxy. In some embodiments, $R^1$ is fluoro. In some embodiments, $R^1$ is hydrogen.

In some embodiments, provided herein are compounds of Formula PP5:

PP5 wherein A is arylene or heteroarylene.

In some embodiments, the compound of Formula PP5 is a compound selected from

339

-continued

340

-continued

341

-continued

342

-continued

343

-continued

344

-continued

345

-continued

346

-continued

In some embodiments, the compound of Formula PP5 is a compound selected from

347

-continued

348

-continued

349

-continued

350

-continued

-continued

-continued

In some examples, set forth herein are methods of making a compound of Formula PP5. In some examples, these methods include contacting a compound of Formula P2 with a compound of Formula PP6 under Lewis acid conditions:

P2

PP6

In some of the methods herein, the contacting of a compound of Formula P2 with a compound of Formula PP6 is with a Lewis acid and an aprotic solvent in this contacting step. In some examples, the Lewis acid is selected from $AlBr_3$, $AlCl_3$, $BCl_3$, boron trichloride methyl sulfide, $BF_3$, boron trifluoride etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl), $Zn(OTf)_2$, $Yb(OTf)_3$, $Sc(OTf)_3$, $MgBr_2$, $NiCl_2$, $Sn(OTf)_2$, $Ni(OTf)_2$, or $Mg(OTf)_2$. In some examples, the Lewis acid is zinc chloride. In some examples, the aprotic solvent is selected from perfluorohexane ($CF_3(CF_2)_4CF_3$), a,a,a-trifluorotoluene, pentane, hexane, cyclohexane, methylcyclohexane, dioxane, carbon tetrachloride, freon-11 ($CFCl_3$), benzene, toluene, triethyl amine, carbon disulfide, diisopropyl ether, diethyl ether, t-butyl methyl ether, chloroform, ethyl acetate, 1,2-dimethoxyethane (glyme), 2-methoxyethyl ether (diglyme), tetrahydrofuran, dichloromethane (methylene chloride), pyridine, 2-butanone (MEK), acetone, hexamethylphosphoramide, N-methylpyrrolidinone, nitromethane, dimethylformamide, acetonitrile, sulfolane, dimethyl sulfoxide, or propylene carbonate. In some examples, the aprotic solvent is dichloromethane. In some of the methods herein, the contacting of a compound of Formula P2 with a compound of Formula PP6 includes contacting zinc chloride and dichloromethane with a compound of Formula P2 and a compound of Formula PP6.

In some of these methods, the compound of Formula PP5 has the Formula PP5A:

PP5A wherein $R^1$ and n are as defined herein.

In some of these methods, $R^1$ is, independently, alkyl, alkoxy, heteroalkyl, halo, haloalkyl, or haloalkoxy. In some embodiments, $R^1$ is, independently, $C_{1-6}$ alkyl, $C_{1-6}$ alkoxy, $C_{1-6}$ haloalkyl, $C_{1-6}$ haloalkoxy, or halo. In some embodiments, $R^1$ is, independently, $C_{1-6}$ alkyl or $C_{1-6}$ alkoxy. In some embodiments, $R^1$ is halo. In some embodiments, $R^1$ is, independently, alkoxy. In some embodiments, $R^1$ is, independently, methoxy, ethoxy, or propoxy. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is chloro. In some embodiments, $R^1$ is bromo. In some embodiments, n, m, p, or q is 0, 1 or 2. In some embodiments, n, m, p, or q is 0 or 1. In some embodiments, n, m, p, or q is 0.

In some of these methods, the compound of Formula PP5 has the Formula PP5A:

PP5A wherein:
$R^1$ is, independently, alkyl, alkoxy, heteroalkyl, halo, haloalkyl, or haloalkoxy; and n is 0, 1, or 2.

In some embodiments, the methods disclosed herein include a compound of PP6 selected from 4-isocyanato-2-methyl-1-nitro-benzene, 1-isocyanato-2-methyl-4-nitro-benzene, 2-bromo-4-isocyanato-1-nitro-benzene, 2-chloro-1-isocyanato-4-nitro-benzene, 3-chloro-1-isocyanato-4-nitro-benzene, 2-fluoro-1-isocyanato-4-nitro-benzene, 2-bromo-1-isocyanato-4-nitro-benzene, 4-isocyanato-2-methoxy-1-nitro-benzene, 1-isocyanato-2-methoxy-4-nitro-benzene, 4-isocyanato-1-nitro-2-trifluoromethyl-benzene, or 1-isocyanato-4-nitro-2-trifluoromethyl-benzene.

In some embodiments, the methods disclosed herein include a compound of PP6 having any one of the following formula:

-continued wherein $R^1$ is, independently at each occurrence, $C_{1-6}$ alkyl, $C_{1-6}$ alkoxy, halo, $C_{1-6}$ haloalkyl, or $C_{1-6}$ haloalkoxy, wherein n is 0, 1, 2, 3, or 4. In certain of these embodiments, $R^1$ is methoxy or methyl. In some specific embodiments, $R^1$ is methoxy, methyl, fluoro, chloro, bromo or trifluoromethyl. In certain embodiments, n is 1 or 2. In some of these embodiments, n is 1. In some embodiments, $R^1$ is fluoro, chloro, bromo, or iodo. In some embodiments, $R^1$ is methyl. In some embodiments, $R^1$ is methoxy. In some embodiments, $R^1$ is trifluoromethyl. In some embodiments, $R^1$ is fluoro. In some embodiments, $R^1$ is chloro. In some embodiments, $R^1$ is bromo.

In some embodiments, the methods disclosed herein further including reducing a compound of Formula PP5 by contacting a compound of Formula PP5 with a suitable reducing agent:

wherein A is arylene or heteroarylene.

In some of these methods, the suitable reducing agent includes a metal, a metal foil, a metal powder, a dust of a metal, a metal amalgam, or metal filings. In certain embodiments, the metal is selected from zinc, iron, aluminum, palladium, or Raney nickel. In some of these methods, the suitable reducing agent is zinc. In some of these methods, the suitable reducing agent is zinc in acetic acid. In some of these methods, the suitable reducing agent is zinc dust in acetic acid.

In some embodiments, the methods disclosed herein further including reducing a compound of Formula PP5 by contacting a compound of Formula PP5 with a suitable reducing agent under particular reducing agent conditions. In some examples, the methods include reducing a compound of Formula PP5 with a reducing agent selected from zinc dust, iron, aluminum, palladium, or Raney nickel. In some examples, the methods include reducing a compound of Formula PP5 with zinc dust. In some examples, the methods include reducing a compound of Formula PP5 with zinc dust and a solvent selected from acetic acid, formic acid, pTsOH, or $NH_4Cl$. In some examples, the methods include reducing a compound of Formula PP5 with zinc dust and acetic acid. In some examples, the methods include reducing a compound of Formula PP5 with about twenty (20) equivalents of zinc dust and forty (40) equivalents of acetic acid. In some examples, the reducing is conducted at a temperature between 0 and 70° C. In some examples, the reducing is conducted at a temperature of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70° C. In some examples, the reducing is conducted for 1 to 40 hours. In some examples, the reducing is conducted for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 hours. In some examples, the reducing is conducted for 24 hours. In some examples, the reducing is conducted at room temperature for about from 1 to 24 hours.

In some examples, the above method steps are performed or conducted in a solvent having 10-50% water (by volume) in a miscible organic solvent. In some examples, the miscible organic solvents is THF, Dioxane, or diethyl ether. Compounds of Formula III:

357 can be synthesized by contacting compounds of Formula PP1:

PP1

358 with a binding agent under conjugation conditions, wherein:

BA is a binding agent;

SP is a spacer;

$SP^R$ is a reactive spacer;

$R^{AA1}$ is an amino acid side chain;

$R^{AA2}$ is an amino acid side chain;

A is arylene or heteroarylene; and k is an integer from 1 to 30.

Compounds of Formula PP1 can be prepared by contacting a compound of Formula II with the compound of Formula PP7:

(II)

PP7

PP1 wherein:

SP$^R$ is a reactive spacer;

R$^{AA1}$ is an amino acid side chain;

R$^{AA2}$ is an amino acid side chain; and

A is arylene or heteroarylene.

Compounds of Formula PP7 can be prepared by contacting a compound of Formula PP9 with a bifunctional spacer:

PP9

PP7

Illustrative bifunctional spacers include, but are not limited to:

and

Compounds of Formula PP1 can be prepared by contacting an activated form of a compound of Formula PP10 with a compound of Formula (II):

PP10

-continued (II)

PP1 wherein Y is a moiety that renders the carboxylic group to which it is attached electrophilic. Compound of Formula PP10 can be prepared by first coupling its corresponding amino acids using standard amino acid coupling techniques, including, for example, active ester formation using HATU, BOP/HOBt, or EDC/N-hydroxysuccinamide in the presence of DIEA, DBU, EEDG or tributylamine. Compound of Formula PP10 can be prepared by then subsequently attaching the RL using standard coupling techniques, including, for example, active ester formation using HATU, BOP/HOBt, or EDC/N-hydroxysuccinamide in the presence of DIEA, DBU, EEDQ or tributylamine.

Bifunctional spacers are compounds that react with the compound of Formula PP9 to append the SP$^R$ moiety present in the compounds of Formula PP7. Illustrative bifunctional spacers include, but are not limited to:

-continued

E. Methods of Use and Pharmaceutical Compositions

The present disclosure includes methods of treating or preventing diseases, conditions, or disorders e.g., proliferative diseases such as cancer, comprising administering a therapeutically effective amount or one or more of the compounds disclosed herein, e.g., one or more of the compounds of Formula (I) or (II). Diseases, disorders, and/or conditions include, but are not limited to, those associated with the antigens listed herein. In some embodiments, the antigen is PSMA, MUC16, STEAP2, or EGFRvIII.

The compounds disclosed herein can be used for treating primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the compounds provided herein are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, or melanoma. In some embodiments, the cancer is breast cancer.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET antagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-$\alpha$ inhibitor (e.g., an anti-PDGFR-$\alpha$ antibody), a PDGFR-$\beta$ inhibitor (e.g., an anti-PDGFR-$\beta$ antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), etc. Other agents that may be beneficially administered in combination with compounds of the disclosure include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

Suitable therapeutic agents also include, but are not limited to chemotherapeutic agents, including alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)- imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The compounds described herein can also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

In some embodiments of the methods described herein, multiple doses of a compound described herein (or a pharmaceutical composition comprising a combination of an compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all contain the same amount the compound described herein, but generally can differ from one another in terms of frequency of administration. In certain embodiments, the amount of the compound contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula (I) and (II), e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to: buffers for maintenance of proper composition pH (e.g., citrate buffers, succinate buffers, acetate buffers, phosphate buffers, lactate buffers, oxalate buffers and the like), carrier proteins (e.g., human serum albumin), saline, polyols (e.g., trehalose, sucrose, xylitol, sorbitol, and the like), surfactants (e.g., polysorbate 20, polysorbate 80, polyoxalate, and the like), antimicrobials, and antioxidants.

F. Examples

Proton NMR spectra of linkers were acquired on a Varian 300 MHz instrument, while spectra of payloads and payload-linkers were acquired on a Varian 500 MHz instrument. Mass spectra were collected on an Agilent LCMS instruments using electrospray ionization and either an ion trap mass analyzer or a single quadrupole analyzer. For all Examples, only the most abundant isotopes acquired by mass spectrometry are reported. All starting materials were purchased commercially and used without purification, unless otherwise noted, while solvents were purchased commercially and dried where necessary via methods well known in the art. The following is a list of the abbreviations used in the Examples, with their full chemical names in parentheses: Ahx (6-aminohexanoic acid), Boc (N-tert-butoxycarbonyl), Cap (caproyl), $CDCl_3$ (chloroform-d), $CD_3OD$ (methanol-$d_4$), Cit (L-citrulline), DCM (dichloromethane), DIEA (N,N-diisopropylethylamine), DMF (N,N-dimethylformamide), EDC (N-(3-Dimethylaminopropyl)-N'-ethylcarbodiimide hydrochloride), EEDQ (2-Ethoxy-1-ethoxycarbonyl-1,2-dihydroquinoline), EtOAc (ethyl acetate), Fmoc (9-fluorenylmethoxycarbonyl), HATU (1-[Bis(dimethylamino)methylene]-1H-1,2,3-triazolo[4,5-b]pyridinium 3-oxid hexafluorophosphate), HCl (aqueous hydrochloric acid), HOAc (glacial acetic acid), HOAT (1-hydroxy-7-azabenzotriazole), HPLC (high-performance liquid chromatography), LCMS (tandem HPLC and mass spectrometry), Mal (maleimide), MeCN (acetonitrile), MeOH (methanol), MS (low resolution mass spectrometry), $NaHCO_3$(sodium bicarbonate), $Na_2SO_4$ (anhydrous sodium sulfate), $NH_4Cl$ (ammonium chloride), NHS (N-hydroxysuccinimide), NMR (nuclear magnetic resonance spectroscopy), OSu (succinate ester), TEA (triethylamine), TFA (trifluoroacetic acid), THF (tetrahydrofuran), TLC (thin-layer chromatography), Val (L-valine), $ZnCl_2$ (zinc chloride).

Example 1

Figure 9:
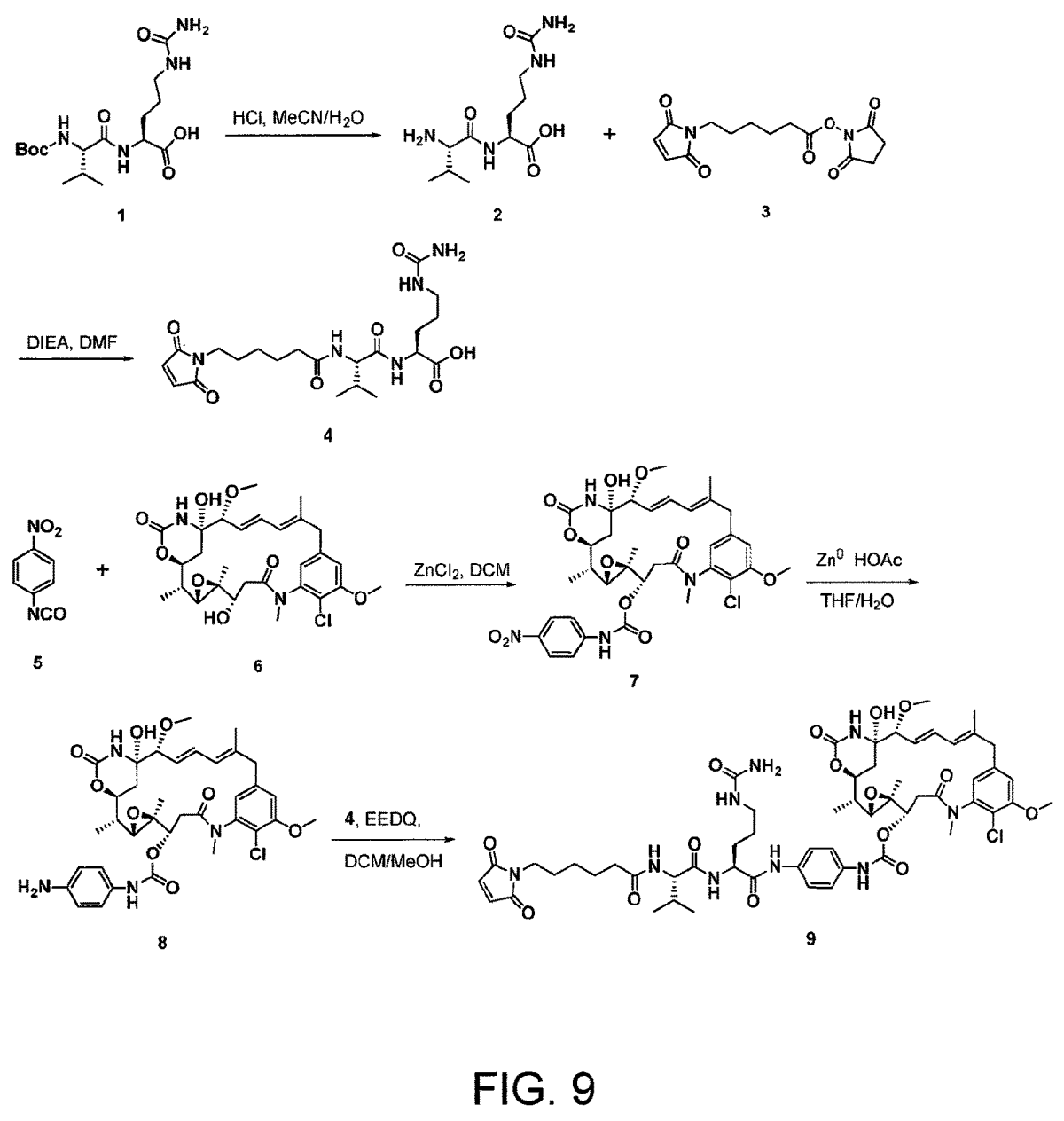

Example 1 refers to compounds illustrated in FIG. 9.

Maytan-3-O-carbamoyl-N-phenyl-p-(amino-Cit-Val-Cap-Mal) (9)

Step A: L-valine-L-citrulline (2)

To a 50 mL round bottom flask equipped with a magnetic stirrer and nitrogen inlet was charged Boc-L-valine-L-citrulline (1, 0.5 g; 1.3 mmol), acetonitrile (10 mL) and water (10 mL). An aqueous solution of 1 M HCl (13 mL; 13 mmol) was added and this solution was stirred at ambient temperature for 18 hours (h). The solution was frozen and lyophilized to a white solid. The solid was extracted with 10% MeOH in DCM, the organic layer was dried over $Na_2SO_4$, filtered and concentrated to afford the title compound (0.4 g, 98% yield) as a clear colorless oil. MS (ESI, pos. & neg.): calc'd for $C_{11}H_{22}N_4O_4$, 274.2; found 275.2 (M+H), 273.2 (M−H).

Step B: 6-Maleimidyl-caproamidyl-L-valine-L-citrulline (4)

To a 25 mL round bottom flask equipped with a magnetic stirrer and nitrogen inlet was charged L-valine-L-citrulline (2, 0.4 g; 1.3 mmol), 6-maleimido-caproic acid succinate ester (3, 0.6 g; 2.0 mmol) in DMF (3 mL) followed by DIEA (0.4 mL; 2.0 mmol). The solution was stirred at ambient temperature for 18 hours, diluted with water (2 mL) and loaded onto a C18 column eluting with 5-95% MeCN in water (containing 0.05% HOAc). The fractions containing product were combined, frozen and lyophilized to afford the title compound (0.3 g, 47% yield) as a white solid. MS (ESI, pos. & neg.): calc'd for $C_{21}H_{33}N_5O_7$, 467.2; found 468.4 (M+H), 466.4 (M−H).

Step C: Maytan-3-O-carbamoyl-N-(4-nitrobenzene) (7)

To a dry round bottom flask was weighed maytansinol (6) (prepared as previously described in the art, 114 mg, 0.202 mmol) and p-nitrophenyl isocyanate (5, 73 mg, 0.445 mmol). The mixture was dissolved in dry DCM (10 mL) and treated dropwise with a 1.0 M solution of zinc chloride in diethyl ether (0.50 mL, 0.50 mmol). The flask was sealed with a rubber septum, purged with argon via needle, and the reaction stirred at ambient temperature for 18 h. LCMS showed complete conversion of the maytansinol. The reaction was diluted with water and extracted three times with EtOAc. The combined organic layers were washed with saturated aqueous (aq.) NaHCO$_3$ and brine, dried over Na$_2$SO$_4$, and filtered. The evaporated product was not very soluble in MeCN/water, so it was concentrated to dryness again in vacuo, dissolved in EtOAc/DCM, and filtered over Na$_2$SO$_4$. The filtrate was then purified by flash chromatography on silica gel (gradient elution: 50-100% EtOAc in hexanes) and the fractions containing product were combined, concentrated, and dried in vacuo giving the title compound as a yellow solid (50 mg, 34%). MS (ESI, pos.): calc'd for C$_{35}$H$_{41}$N$_4$O$_{11}$C, 728.3; found 729.2 (M+H).

Step D:
Maytan-3-O-carbamoyl-N-(4-aminobenzene) (8)

The product of the preceding step (7.49 mg, 0.067 mmol) and zinc dust (85 mg, 1.30 mmol) were weighed into a round bottom flask and treated with THF (4 mL), water (1 mL), and HOAc (0.100 mL, 1.75 mmol). The flask was sealed with a rubber septum, purged with argon, and the reaction stirred at ambient temperature for 18 h. The reaction was filtered over Celite, solids rinsed with acetonitrile (MeCN, 3×5 mL), and the filtrate concentrated in vacuo to an amber oil. This was purified directly on a C18 Aq RediSep Gold column via ISCO (gradient elution: 20-80% MeCN in water, 0.05% acetic acid in both, over 12 min). The fractions containing product were combined, partially concentrated in vacuo, frozen on dry ice, and lyophilized for 3 days (d) giving the title compound as a cream-colored solid (32 mg, 63%). MS (ESI, pos.): calc'd for C$_{35}$H$_{43}$N$_4$O$_9$Cl, 698.3; found 699.2 (M+H).

Step E: Maytan-3-O-carbamoyl-N-phenyl-p-(amino-Cit-Val-Cap-Mal) (9)

The product of the preceding step (8, 16 mg, 0.021 mmol), 6-Maleimidyl-caproamidyl-L-valine-L-citrulline (4, 16 mg, 0.034 mmol), and EEDQ (15 mg, 0.061 mmol) were weighed into a round bottom flask and dissolved in dry DCM (2 mL) and anhydrous methanol (1 mL). The flask was sealed with a rubber septum, purged with argon, and the reaction stirred at ambient temperature for 18 h. The reaction was concentrated in vacuo, dissolved in MeCN/water, and purified directly on a C18 Aq RediSep Gold column via ISCO (gradient elution: 20-80% MeCN in water, 0.05% acetic acid in both, over 12 min). The product did not separate well, so the impure product fractions were lyophilized and repurified twice by preparative HPLC on a Phenomenex Gemini 5u, 30×150 mm C18 column (first 40-80% then 20-80% MeCN in water, 0.1% HOAc both, over 20 min, 30 mL/min). The fractions containing product were combined, partially concentrated in vacuo, frozen on dry ice, and lyophilized overnight giving the title compound as a white solid (5 mg, 21%). MS (ESI, pos.): calc'd for C$_{56}$H$_{74}$N$_9$O$_{15}$Cl, 1147.5; found 1148.5 (M+H), 1130.4 (M−H$_2$O+H), 1170.5 (M+Na). $^1$H NMR (500 MHz, Methanol-d4) δ: 7.48-7.42 (m, 2H), 7.40 (t, J=8.3 Hz, 2H), 7.07 (s, 1H), 7.02 (d, J=1.8 Hz, 1H), 6.69 (d, J=4.7 Hz, 1H), 6.49 (dd, J=15.4, 11.1 Hz, 1H), 6.14 (d, J=8.9 Hz, 1H), 5.33 (dd, J=15.4, 8.7 Hz, 1H), 4.47 (dd, J=11.9, 2.9 Hz, 1H), 4.40 (dd, J=8.9, 5.2 Hz, 1H), 4.25-4.14 (m, 1H), 4.07 (dd, J=12.0, 7.6 Hz, 1H), 3.88 (s, 3H), 3.50 (d, J=12.7 Hz, 1H), 3.43 (d, J=8.9 Hz, 1H), 3.38 (t, J=7.1 Hz, 2H), 3.18-3.13 (m, 2H), 3.11 (s, 4H), 3.09-2.97 (m, 2H), 2.90 (dd, J=9.8, 3.7 Hz, 1H), 2.58-2.47 (m, 1H), 2.18 (t, J=7.5 Hz, 2H), 2.14-2.04 (m, 2H), 2.00-1.92 (m, 1H), 1.87 (d, J=4.9 Hz, 1H), 1.80 (dd, J=10.0, 4.8 Hz, 1H), 1.67 (dd, J=13.7, 2.1 Hz, 2H), 1.63 (s, 4H), 1.59-1.41 (m, 8H), 1.41-1.33 (m, 2H), 1.25-1.17 (m, 4H), 1.17-1.09 (m, 4H), 1.04 (d, J=6.5 Hz, 1H), 0.94 (dd, J=11.7, 6.7 Hz, 1H), 0.87 (dt, J=7.9, 4.0 Hz, 6H), 0.77 (s, 3H).

Example 2

Figure 10:
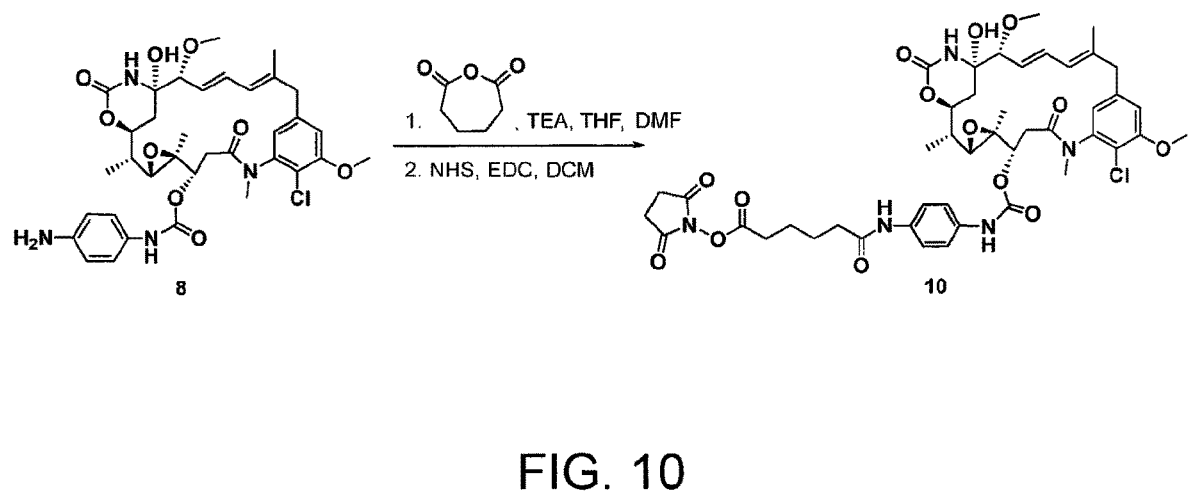

Example 2 refers to compounds illustrated in FIG. 10.

Maytan-3-O-carbamoyl-N-phenyl-p-amino-adipic Acid Succinate Ester (10)

Step A:
Maytan-3-O-carbamoyl-N-phenyl-p-amino-adipic Acid

The product of Example 1, step D (8, 20 mg, 0.0263 mmol) and adipic anhydride (a.k.a—oxepane-2,7-dione, 20 mg, 0.156 mmol) were weighed into a round bottom flask, dissolved in THF (2.0 mL), and treated with triethylamine (0.010 mL, 0.0717 mmol). The solids would not dissolve, so DMF (1.0 mL) was added, the flask sealed with a rubber septum, purged with argon, and the reaction stirred at ambient temperature. After 18 h, LCMS showed complete conversion of 2, so the reaction was concentrated to an oil in vacuo, dissolved in MeCN/water, and purified on a C18 Aq RediSep Gold column via ISCO (gradient elution: 20-80% MeCN in water, 0.05% acetic acid in both). The fractions containing product were combined, partially concentrated in vacuo, frozen on dry ice, and lyophilized for 18 h giving the title compound as a white solid (19 mg, 86%). MS (ESI, pos.): calc'd for C$_{41}$H$_{51}$ClN$_4$O$_{12}$, 826.3; found 827.3 (M+H), 849.3 (M+Na).

Step B:
Maytan-3-O-carbamoyl-N-phenyl-p-amino-adipic Acid Succinate Ester (10)

The product of the preceding step (18 mg, 0.0218 mmol), N-hydroxysuccinimide (19 mg, 0.165 mmol), and EDC hydrochloride (34 mg, 0.177 mmol) were weighed into a round bottom flask, dissolved in DCM (3 mL), the flask sealed with a rubber septum, purged with argon, and the reaction stirred at ambient temperature. After 20 h the reaction was concentrated in vacuo, dissolved in MeCN, treated with a couple drops of 10% aqueous acetic acid, and purified on a C18 Aq RediSep Gold column via ISCO (gradient elution: 30-90% MeCN in water, 0.05% acetic acid in both). The fractions containing product were combined, partially concentrated in vacuo, frozen on dry ice, and lyophilized for 18 h giving the title compound as a white solid (10 mg, 50%). MS (ESI, pos.): calc'd for C$_{45}$H$_{54}$N$_5$O$_{14}$Cl, 923.3; found 924.3 (M+H), 946.3 (M+Na). $^1$H NMR (500 MHz, CDCl$_3$) δ: 7.62 (s, 1H), 7.54 (d, 2H, J=9 Hz), 7.39 (d, 2H, J=9 Hz), 6.84 (d, 1H, J=2 Hz), 6.69 (d, 1H, J=2 Hz), 6.58 (s, 1H), 6.47 (dd, 1H, J=16 Hz, 11 Hz), 6.18 (s, 1H), 6.10 (d, 1H, J=11 Hz), 5.37 (dd, 1H, J=16 Hz, 9 Hz), 4.81 (dd, 1H, J=12 Hz, 2 Hz), 4.32 (t, 1H, J=10 Hz), 4.00 (s, 3H), 3.50 (d, 1H, J=14 Hz), 3.47 (d, 1H, J=9 Hz), 3.31 (s, 3H), 3.27 (d, 1H, J=13 Hz), 3.20 (s, 3H), 2.89 (m, 6H), 2.68 (m, 2H), 2.51 (dd, 1H, J=14 Hz, 12 Hz), 2.43 (m, 2H), 2.26 (dd, 1H, J=14 Hz, 2 Hz), 1.89 (m, 5H), 1.71 (s, 3H), 1.29 (m, 5H), 0.91 (s, 3H).

Example 3

Figure 11:
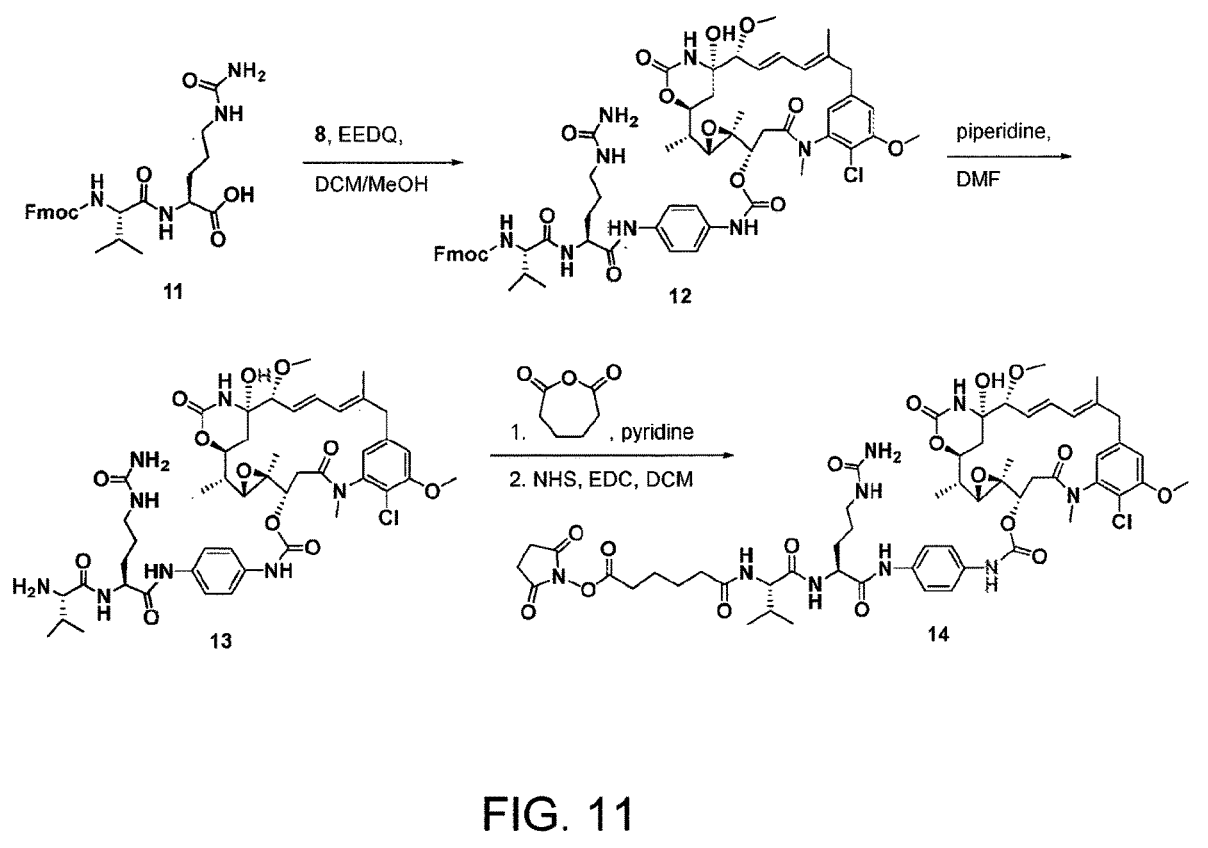

Example 3 refers to compounds illustrated in FIG. 11.

Maytan-3-O-carbamoyl-N-phenyl-p-amino-Cit-Val-adipic Acid Succinate Ester (14)

Step A: Maytan-3-O-carbamoyl-N-phenyl-p-amino-Cit-Val-Fmoc (12)

The product of Example 1, step D (8, 54 mg, 0.071 mmol) and Fmoc-L-valine-L-citrulline (11, 151 mg, 0.304 mmol) were coupled via the method of Example 1, step E giving the title compound as a white solid (51 mg, 61%). MS (ESI, pos.): calc'd for $C_{61}H_{73}ClN_8O_{14}$, 1176.5; found 1178.1 (M+H), 1200.1 (M+Na).

Step B: Maytan-3-O-carbamoyl-N-phenyl-p-amino-Cit-Val (13)

The product of the preceding step (12, 49 mg, 0.042 mmol) was dissolved in a 5% v/v solution of piperidine in DMF (2.0 mL), and the mixture stirred at ambient temperature. After 20 h the reaction was acidified with a few drops of 10% aqueous acetic acid, diluted with MeCN and water (ca. 1 mL each), and purified on a C18 Aq RediSep Gold column via ISCO (gradient elution: 20-80% MeCN in water, 0.05% acetic acid in both). The fractions containing product were combined, partially concentrated in vacuo, frozen on dry ice, and lyophilized for 18 h giving the title compound as a cream-colored solid (34 mg, 81%). MS (ESI, pos.): calc'd for $C_{46}H_{63}ClN_8O_{12}$, 954.5; found 955.9 (M+H), 977.9 (M+Na).

Step C: Maytan-3-O-carbamoyl-N-phenyl-p-amino-Cit-Val-adipic Acid

The product of the preceding step (13, 49 mg, 0.042 mmol) and adipic anhydride (a.k.a—oxepane-2,7-dione, 20 mg, 0.156 mmol) were weighed into a round bottom flask, dissolved in pyridine (2 mL), the flask sealed with a rubber septum, purged with argon, and the reaction stirred at ambient temperature. After 18 h the reaction was concentrated to dryness under high vacuum, acidified with a few drops of 10% aqueous acetic acid, dissolved in MeCN, and purified on a C18 Aq RediSep Gold column via ISCO (gradient elution: 20-80% MeCN in water, 0.05% acetic acid in both). The fractions containing product were combined, partially concentrated in vacuo, frozen on dry ice, and lyophilized for 3 d giving the title compound as a white solid (14 mg, 40%). MS (ESI, pos.): calc'd for $C_{52}H_{71}ClN_8O_{15}$, 1082.5; found 1084.0 (M+H), 1106.1 (M+Na).

Step D: Maytan-3-O-carbamoyl-N-phenyl-p-amino-Cit-Val-adipic Acid Succinate Ester (14)

Using the method of Example 2, step B, the title compound was prepared from the product of the preceding step (13 mg, 0.012 mmol) as a white solid (7 mg, 50%). MS (ESI, pos.): calc'd for $C_{56}H_{74}ClN_9O_{17}$, 1179.5; found 1182.1 (M+H), 1203.2 (M+Na). $^1$H NMR (500 MHz, DMSO-$d_6$) δ: 9.91 (s, 1H), 8.48 (s, 1H), 8.08 (d, J=7.6 Hz, 1H), 7.84 (d, J=8.6 Hz, 1H), 7.54 (d, J=8.8 Hz, 2H), 7.44 (d, J=8.5 Hz, 2H), 7.26 (s, 1H), 7.19 (s, 1H), 6.77 (s, 1H), 6.59-6.46 (m, 1H), 6.36 (s, 1H), 5.98 (s, 1H), 5.53 (s, 1H), 5.40 (s, 2H), 5.30 (dd, J=15.1, 9.1 Hz, 1H), 4.44-4.31 (m, 2H), 4.27-4.18 (m, 1H), 4.14 (t, J=11.2 Hz, 1H), 3.94 (s, 3H), 3.63 (d, J=12.0 Hz, 1H), 3.42 (d, J=9.1 Hz, 1H), 3.18 (s, 4H), 3.10 (s, 3H), 3.06-2.98 (m, 1H), 2.98-2.91 (m, 1H), 2.89 (d, J=9.7 Hz, 1H), 2.81 (s, 4H), 2.73-2.65 (m, 2H), 2.30-2.22 (m, 1H), 2.21-2.14 (m, 1H), 2.06 (d, J=13.2 Hz, 1H), 1.97 (dd, J=12.5, 5.6 Hz, 1H), 1.66 (s, 3H), 1.60 (d, J=5.5 Hz, 5H), 1.53-1.30 (m, 6H), 1.23 (s, 1H), 1.11 (d, J=6.3 Hz, 3H), 0.85 (dd, J=15.2, 6.7 Hz, 6H), 0.75 (s, 3H).

Example 4

Figure 12:
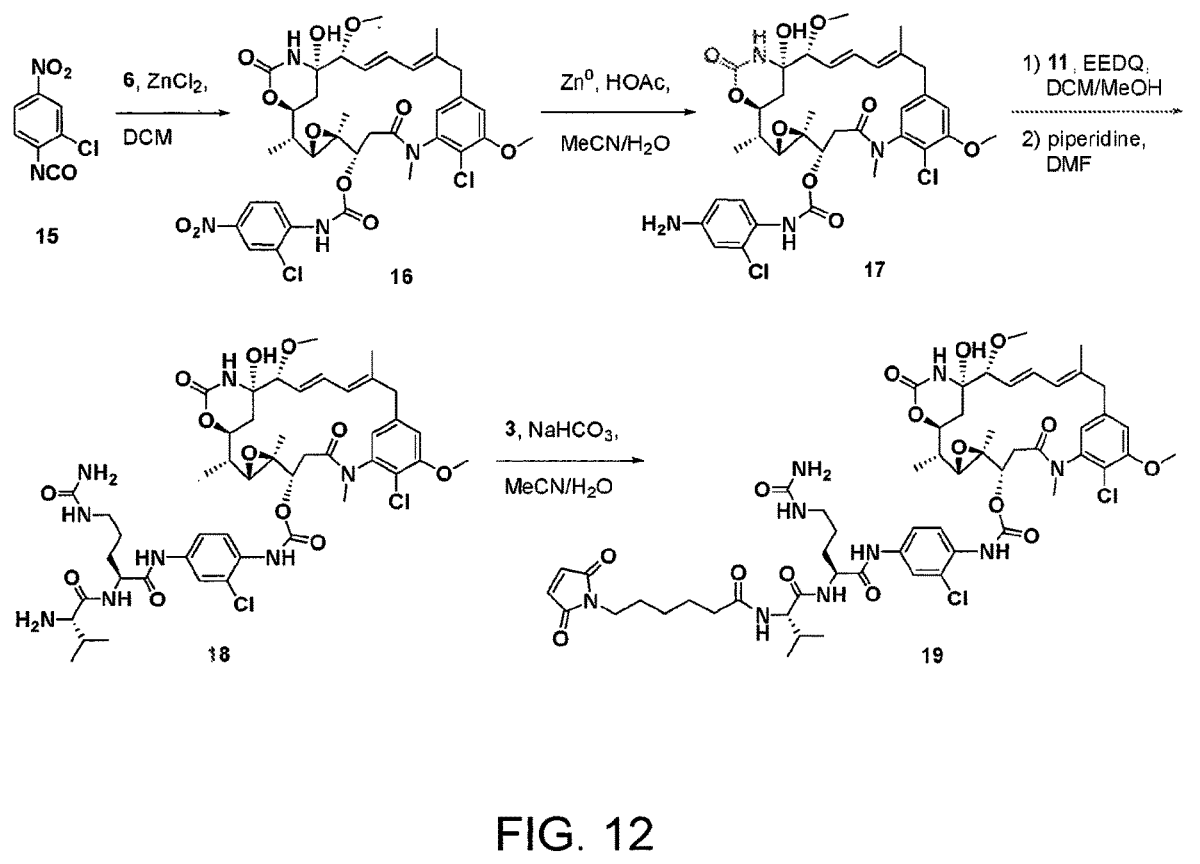

Example 4 refers to compounds illustrated in FIG. 12.

Maytan-3-O-carbamoyl-N-phenyl-2-chloro-4-(amino-Cit-Val-Cap-Mal) (19)

Step A: Maytan-3-O-carbamoyl-N-(2-chloro-4-nitro)benzene (16)

To a dry round bottom flask was weighed 2-chloro-4-nitrophenyl isocyanate (15, 525 mg, 2.64 mmol) and maytansinol (6, 503 mg, 0.890 mmol). The mixture was dissolved in dry DCM (10 mL) and treated dropwise with a 1.0 M solution of zinc chloride in diethyl ether (1.20 mL, 1.20 mmol). The flask was sealed with a rubber septum, purged with argon via needle, and the reaction stirred at ambient temperature. After 18 h the reaction was incomplete by LCMS, so the flask was topped with a water condenser and the reaction heated to 50° C. After 6 h, most of the maytansinol was consumed by LCMS so the reaction was cooled to ambient temperature and stirred overnight. After another 18 h the reaction was concentrated in vacuo, dissolved in MeCN/DCM, and purified by flash chromatography on silica gel (gradient elution: 10-50% MeCN in DCM). The slow-running product fractions were combined, concentrated, and dried in vacuo for 3 d giving the title compound as an orange solid (396 mg, 58%). MS (ESI, pos.): calc'd for $C_{35}H_{40}Cl_2N_4O_{11}$, 762.2; found 763.1 (M+H).

Step B: Maytan-3-O-carbamoyl-N-(2-chloro-4-amino)benzene (17)

The title compound was prepared from the product of the preceding step (16, 388 mg, 0.509 mmol) as a white solid (301 mg, 75%) using the method of Example 1, step D, except that MeCN was used instead of THF and the reaction was stirred for only 2 h. MS (ESI, pos.): calc'd for $C_{35}H_{42}Cl_2N_4O_9$, 732.2; found 733.1 (M+H). $^1$H NMR (500 MHz, Chloroform-d) δ: 7.83 (d, J=8.8 Hz, 1H), 6.85 (s, 2H), 6.79 (s, 1H), 6.74 (d, J=2.6 Hz, 1H), 6.60 (dd, J=8.8, 2.6 Hz, 1H), 6.42 (dd, J=15.4, 11.0 Hz, 1H), 6.30 (d, J=10.8 Hz, 1H), 6.20-6.13 (m, 1H), 5.23 (dd, J=15.3, 9.0 Hz, 1H), 4.80 (dd, J=11.8, 2.5 Hz, 1H), 4.37 (ddd, J=12.4, 10.5, 2.0 Hz, 1H), 4.00 (s, 3H), 3.56 (d, J=13.0 Hz, 1H), 3.43 (d, J=9.0 Hz, 1H), 3.26 (s, 4H), 3.20 (s, 3H), 3.04 (d, J=9.8 Hz, 1H), 2.85-2.73 (m, 1H), 2.49 (dd, J=13.7, 11.8 Hz, 1H), 2.23 (dd, J=13.7, 2.5 Hz, 1H), 1.78 (d, J=13.5 Hz, 1H), 1.69 (s, 3H), 1.54-1.43 (m, 2H), 1.31 (d, J=6.4 Hz, 3H), 1.23 (t, J=12.6 Hz, 1H), 0.88 (s, 3H).

Step C: Maytan-3-O-carbamoyl-N-2-chloro-4-(aminophenyl-Cit-Val-Fmoc)

Using the method of Example 3, step A, the title compound was prepared from the product of the preceding step (17, 150 mg, 0.189 mmol) as a white solid (174 mg, 76%). MS (ESI, pos.): calc'd for $C_{61}H_{72}Cl_2N_8O_{14}$, 1210.5; found 1213.2 (M+H), 1235.3 (M+Na).

Step D: Maytan-3-O-carbamoyl-N-2-chloro-4-(aminophenyl-Cit-Val) (18)

Using the method of Example 3, step B, the title compound was prepared from the product of the preceding step (172 mg, 0.142 mmol) as a white solid (51 mg, 34%). MS (ESI, pos.): calc'd for $C_{46}H_{62}Cl_2N_8O_{12}$, 988.4; found 989.3 (M+H), 1011.3 (M+Na).

Step E: Maytan-3-O-carbamoyl-N-phenyl-2-chloro-4-(amino-Cit-Val-Cap-Mal) (19)

The product of the preceding step (18, 14 mg, 0.013 mmol) and 6-maleimidyl-caproic acid succinate ester (3, 20 mg, 0.065 mmol) were dissolved in MeCN (2.0 mL) and water (0.5 mL), treated with one drop of saturated aqueous $NaHCO_3$, the flask sealed with a rubber septum, purged with argon, and the reaction stirred at ambient temperature. After 20 h the reaction was acidified with a few drops of 10% aqueous acetic acid, dissolved in MeCN (ca. 2 mL), and purified on a C18 Aq RediSep Gold column via ISCO (gradient elution: 30-90% MeCN in water, 0.05% acetic acid in both). The fractions containing product were combined, partially concentrated in vacuo, frozen on dry ice, and lyophilized for 4 d giving the title compound as a white solid (10 mg, 63%). MS (ESI, pos.): calc'd for $C_{56}H_{73}Cl_2N_9O_{15}$, 1181.5; found 1183.1 (M+H), 1204.1 (M+Na). $^1$H NMR (500 MHz, DMSO-$d_6$) δ: 10.16 (s, 1H), 8.14 (d, J=7.3 Hz, 1H), 7.93 (dd, J=15.2, 2.3 Hz, 1H), 7.81 (d, J=9.1 Hz, 2H), 7.71-7.59 (m, 1H), 7.46 (dd, J=8.8, 2.4 Hz, 1H), 7.21 (d, J=1.7 Hz, 1H), 7.07 (s, 1H), 6.99 (d, J=11.8 Hz, 2H), 6.90 (d, J=8.2 Hz, 1H), 6.57 (dd, J=15.1, 11.2 Hz, 1H), 6.45 (d, J=10.6 Hz, 1H), 5.98 (d, J=6.2 Hz, 1H), 5.91-5.84 (m, 1H), 5.47-5.34 (m, 3H), 4.45 (dd, J=12.0, 2.6 Hz, 1H), 4.40-4.29 (m, 1H), 4.19 (dd, J=8.6, 6.8 Hz, 1H), 4.13 (t, J=11.1 Hz, 1H), 3.94 (s, 3H), 3.57 (d, J=12.4 Hz, 1H), 3.48 (d, J=9.1 Hz, 1H), 3.21 (d, J=3.7 Hz, 4H), 3.07 (s, 3H), 3.05-2.98 (m, 1H), 2.98-2.88 (m, 1H), 2.78 (d, J=9.8 Hz, 1H), 2.43 (t, J=13.1 Hz, 1H), 2.24-2.05 (m, 2H), 2.01 (d, J=13.8 Hz, 1H), 1.98-1.91 (m, 1H), 1.69 (d, J=7.9 Hz, 1H), 1.65 (s, 3H), 1.61 (dd, J=9.2, 4.9 Hz, 1H), 1.54-1.40 (m, 8H), 1.40-1.30 (m, 1H), 1.19 (td, J=15.8, 14.8, 8.2 Hz, 3H), 1.11 (d, J=6.4 Hz, 3H), 0.88 (d, J=6.7 Hz, 1H), 0.84 (dd, J=17.0, 6.8 Hz, 6H), 0.81 (s, 2H).

Example 5

Figure 13:
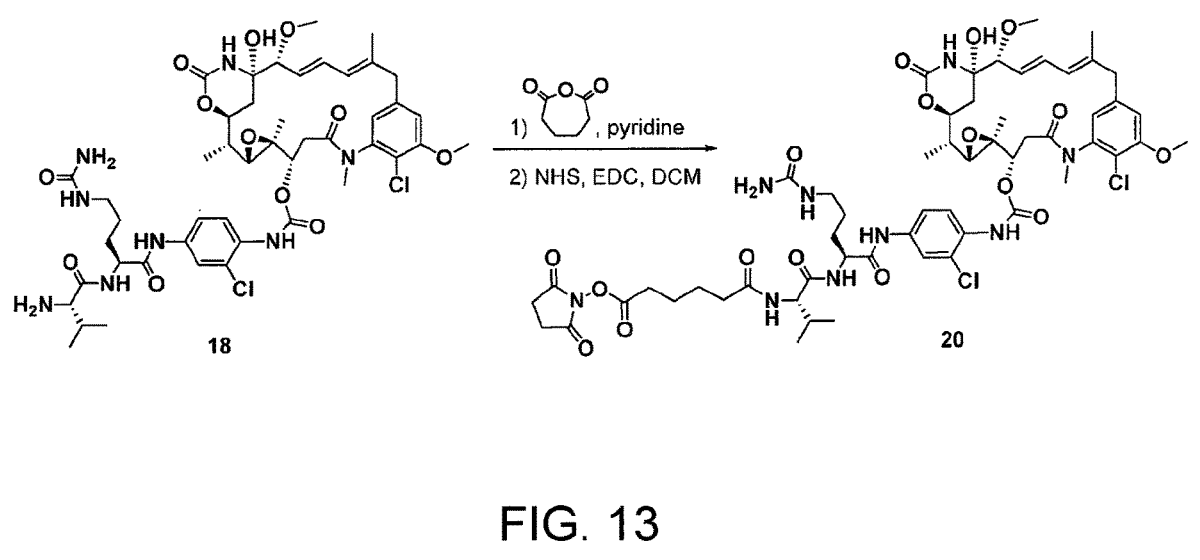

Example 5 refers to compounds illustrated in FIG. 13.

Maytan-3-O-carbamoyl-N-phenyl-2-chloro-4-(amino-Cit-Val-adipic Acid Succinate Ester) (20)

Step A: Maytan-3-O-carbamoyl-N-phenyl-2-chloro-4-(amino-Cit-Val-adipic Acid)

Using the method of Example 3, step C, the title compound was prepared from the product of Example 4, step D (18, 19 mg, 0.018 mmol) as a white solid (11 mg, 55%). MS (ESI, pos.): calc'd for $C_{52}H_{70}Cl_2N_8O_{15}$, 1116.4; found 1119.2 (M+H), 1139.2 (M+Na).

Step B: Maytan-3-O-carbamoyl-N-phenyl-2-chloro-4-(amino-Cit-Val-adipic Acid Succinate Ester) (20)

Using the method of Example 2, step B, the title compound was prepared from the product of the preceding step (11 mg, 0.010 mmol) as a white solid (4 mg, 33%). MS (ESI, pos.): calc'd for $C_{56}H_{73}Cl_2N_9O_{17}$, 1213.5; found 1216.2 (M+H), 1236.3 (M+Na). $^1$H NMR (500 MHz, DMSO-$d_6$) δ: 10.16 (s, 1H), 8.16 (d, J=7.3 Hz, 1H), 7.91 (d, J=2.4 Hz, 1H), 7.84 (d, J=8.7 Hz, 1H), 7.78 (s, 1H), 7.65 (d, J=8.7 Hz, 1H), 7.45 (dd, J=8.7, 2.4 Hz, 1H), 7.21 (d, J=1.8 Hz, 1H), 7.06 (s, 1H), 6.88 (s, 1H), 6.64-6.50 (m, 1H), 6.44 (d, J=11.0 Hz, 1H), 5.97 (d, J=6.2 Hz, 1H), 5.87 (d, J=1.3 Hz, 1H), 5.41 (q, J=7.6, 6.4 Hz, 3H), 4.50-4.39 (m, 1H), 4.34 (d, J=7.0 Hz, 1H), 4.28-4.17 (m, 1H), 4.13 (t, J=11.6 Hz, 1H), 3.94 (s, 3H), 3.56 (d, J=13.9 Hz, 1H), 3.52-3.42 (m, 1H), 3.21 (s, 3H), 3.07 (s, 3H), 3.03 (dt, J=13.1, 6.7 Hz, 2H), 2.98-2.90 (m, 2H), 2.82-2.74 (m, 5H), 2.69-2.64 (m, 2H), 2.24 (d, J=9.9 Hz, 1H), 2.21-2.13 (m, 1H), 2.00 (d, J=13.3 Hz, 1H), 1.98-1.93 (m, 1H), 1.64 (s, 3H), 1.60 (d, J=6.5 Hz, 5H), 1.51 (d, J=13.1 Hz, 1H), 1.47-1.40 (m, 3H), 1.39 (d, J=6.5 Hz, 1H), 1.11 (d, J=6.4 Hz, 3H), 0.85 (dd, J=16.2, 6.8 Hz, 6H), 0.80 (s, 3H).

Example 6

Figure 14:
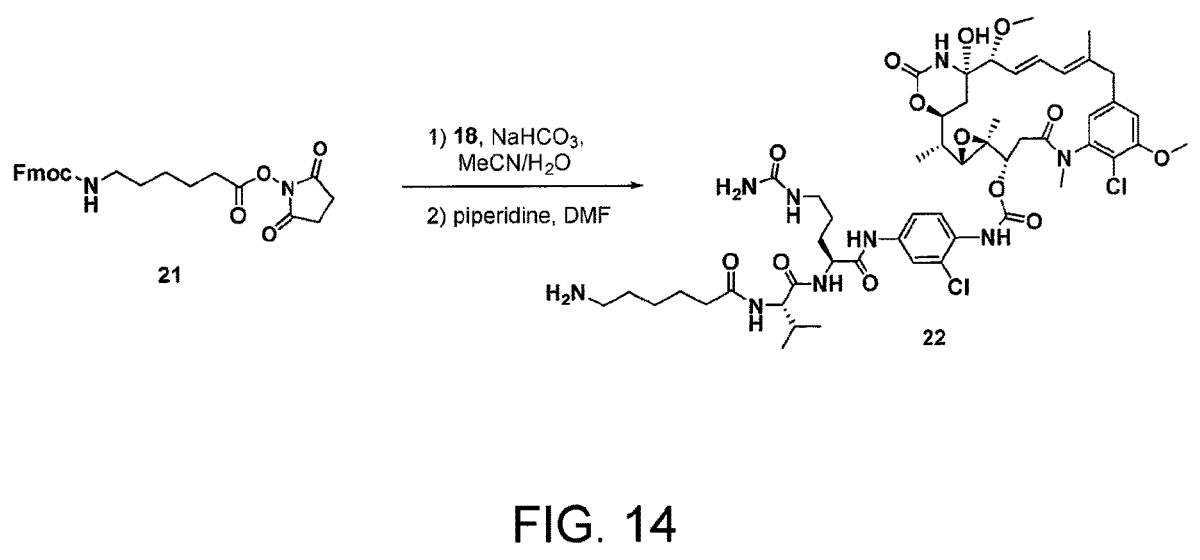

Example 6 refers to compounds illustrated in FIG. 14.

Maytan-3-O-carbamoyl-N-phenyl-2-chloro-4-(amino-Cit-Val-6-Ahx) (22)

Step A: Maytan-3-O-carbamoyl-N-phenyl-2-chloro-4-(amino-Cit-Val-6-Ahx-Fmoc)

The product of Example 4, step D (18, 40 mg, 0.040 mmol) and Fmoc-6-aminohexanoic acid succinate ester (21, 92 mg, 0.204 mmol) were coupled via the method of Example 4, step E, giving the title compound as a white solid (31 mg, 57%). MS (ESI, pos.): calc'd for $C_{67}H_{83}Cl_2N_9O_{15}$, 1323.5; found 1326.5 (M+H), 1346.6 (M+Na).

Step B: Maytan-3-O-carbamoyl-N-2-chloro-4-(aminophenyl-Cit-Val-6-Ahx) (22)

Using the method of Example 3, step B, the title compound was prepared from the product of the preceding step (30 mg, 0.023 mmol) as a white solid (9 mg, 35%) after repurification by preparative HPLC on a Phenomenex Gemini 5u, 30×150 mm C18 column (10-90% MeCN in water, 0.05% HOAc both, over 22 min, 40 mL/min). MS (ESI, pos.): calc'd for $C_{52}H_{73}Cl_2N_9O_{13}$, 1101.5; found 1102.8 (M+H). $^1$H NMR (500 MHz, DMSO-$d_6$) δ: 7.93-7.85 (m, 1H), 7.65 (d, J=8.7 Hz, 1H), 7.49 (d, J=10.2 Hz, 1H), 7.21 (d, J=1.8 Hz, 1H), 7.06 (s, 1H), 6.57 (dd, J=15.1, 11.1 Hz, 1H), 6.44 (d, J=11.2 Hz, 1H), 6.05 (s, 1H), 5.50-5.32 (m, 2H), 4.49-4.39 (m, 1H), 4.34 (s, 1H), 4.23-4.06 (m, 1H), 3.94 (s, 2H), 3.21 (s, 3H), 3.07 (s, 3H), 3.03-2.92 (m, 3H), 2.78 (d, J=9.8 Hz, 1H), 2.41 (d, J=12.7 Hz, 1H), 2.30-2.23 (m, 1H), 2.18 (q, J=6.7 Hz, 2H), 2.05-1.93 (m, 3H), 1.81 (s, 2H), 1.75-1.67 (m, 1H), 1.65 (s, 3H), 1.54-1.41 (m, 7H), 1.41-1.32 (m, 4H), 1.30-1.17 (m, 5H), 1.11 (d, J=6.3 Hz, 3H), 0.85 (dd, J=11.5, 6.7 Hz, 6H), 0.80 (s, 2H).

Example 7

Figure 15:
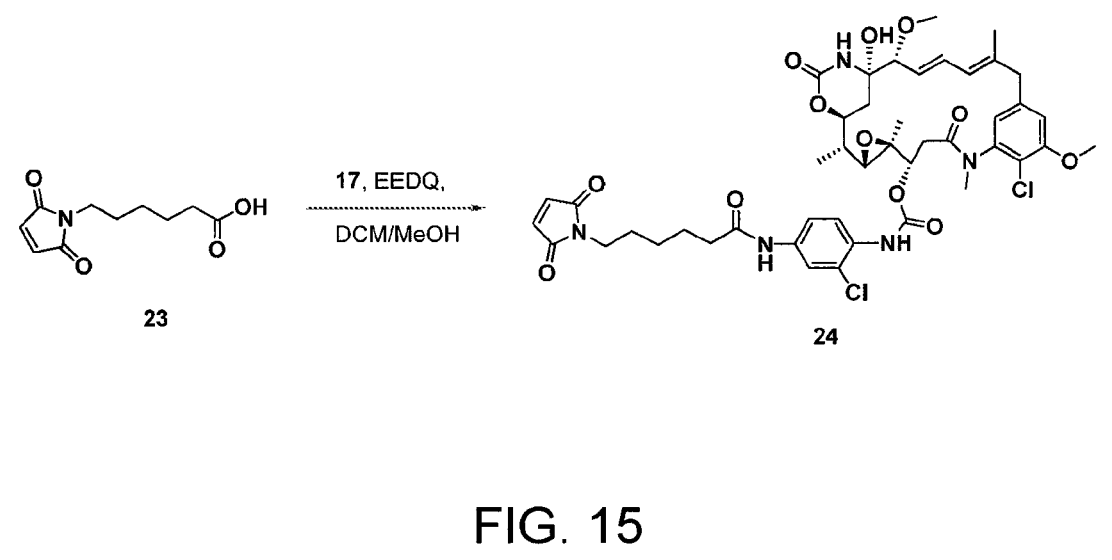

Example 7 refers to compounds illustrated in FIG. 15.

Maytan-3-O-carbamoyl-N-phenyl-2-chloro-4-(amino-Cap-Mal) (24)

The product of Example 4, step B (17.20 mg, 0.025 mmol) and 6-maleimidyl-caproic acid (23, 28 mg, 0.133 mmol) were coupled via the method of Example 1, step E giving the title compound as a white solid (21 mg, 91%) after a second ISCO purification. MS (ESI, pos.): calc'd for $C_{45}H_{53}Cl_2N_5O_{12}$, 925.3; found 926.2 (M+H), 948.2 (M+Na). $^1$H NMR (500 MHz, DMSO-$d_6$) δ: 9.96 (s, 1H), 7.90 (d, J=2.4 Hz, 1H), 7.65 (d, J=8.8 Hz, 1H), 7.60 (s, 1H), 7.43 (dd, J=8.8, 2.4 Hz, 1H), 7.21 (d, J=1.8 Hz, 1H), 7.04 (d, J=1.8 Hz, 1H), 6.98 (s, 2H), 6.72 (s, 1H), 6.58 (dd, J=15.2, 11.1 Hz, 1H), 6.42 (d, J=11.0 Hz, 1H), 5.75 (s, 1H), 5.43 (dd, J=15.3, 9.1 Hz, 1H), 4.51 (dd, J=11.9, 2.6 Hz, 1H), 4.18 (ddd, J=12.4, 10.4, 2.3 Hz, 1H), 3.96 (s, 3H), 3.57 (d, J=12.4 Hz, 1H), 3.50 (d, J=9.1 Hz, 1H), 3.42 (t, J=7.0 Hz, 2H), 3.09 (s, 4H), 2.79 (d, J=9.8 Hz, 1H), 2.45 (dd, J=13.8, 11.9 Hz, 1H), 2.31 (t, J=7.4 Hz, 2H), 2.09-1.98 (m, 1H), 1.88 (s, 1H), 1.67 (s, 3H), 1.65-1.57 (m, 2H), 1.55 (q, J=7.2 Hz, 3H), 1.46 (d, J=12.7 Hz, 2H), 1.34-1.21 (m, 2H), 1.14 (d, J=6.3 Hz, 3H), 0.83 (s, 3H).

Example 8

Figure 16:
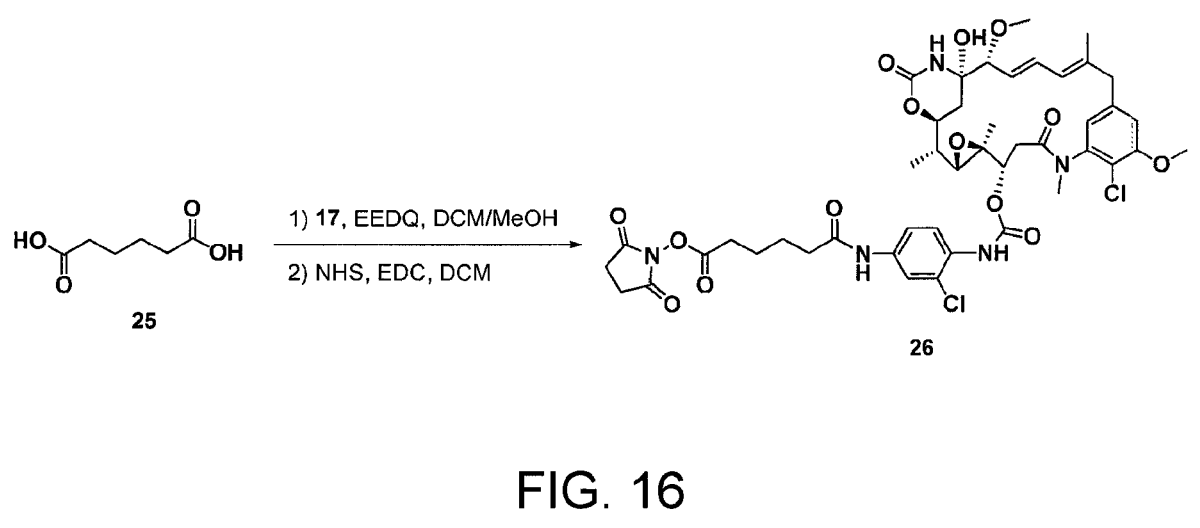

Example 8 refers to compounds illustrated in FIG. 16.

Maytan-3-O-carbamoyl-N-phenyl-2-chloro-4-(amino-adipic Acid Succinate Ester) (26)

Step A: Maytan-3-O-carbamoyl-N-phenyl-2-chloro-4-(amino-adipic Acid)

The product of Example 4, step B (17, 17 mg, 0.021 mmol) and adipic acid (25, 18 mg, 0.123 mmol) were coupled via the method of Example 1, step E giving the title compound as a white solid (11 mg, 59%). MS (ESI, pos.): calc'd for $C_{41}H_{50}Cl_2N_4O_{12}$, 860.3; found 861 (M+H), 883 (M+Na).

Step B: Maytan-3-O-carbamoyl-N-phenyl-2-chloro-4-(amino-adipic Acid Succinate Ester) (26)

Using the method of Example 2, step B, the title compound was prepared from the product of the preceding step (10 mg, 0.012 mmol) as a white solid (11 mg, 100%). MS (ESI, pos.): calc'd for $C_{45}H_{53}Cl_2N_5O_{14}$, 957.3; found 958.0 (M+H), 980.0 (M+Na). $^1$H NMR (500 MHz, Chloroform-d) δ: 8.18 (d, J=2.4 Hz, 1H), 8.06 (d, J=8.9 Hz, 1H), 7.78 (s, 1H), 7.08-6.93 (m, 2H), 6.85 (d, J=1.8 Hz, 1H), 6.81 (d, J=1.8 Hz, 1H), 6.40 (dd, J=15.0, 10.9 Hz, 1H), 6.33 (d, J=11.0 Hz, 1H), 6.14 (d, J=1.4 Hz, 1H), 6.04 (s, 1H), 5.19 (dd, J=15.1, 9.0 Hz, 1H), 4.81 (dd, J=11.8, 2.6 Hz, 1H), 4.39-4.28 (m, 1H), 4.00 (s, 3H), 3.74-3.65 (m, 3H), 3.55 (d, J=13.0 Hz, 1H), 3.41 (d, J=8.8 Hz, 1H), 3.28-3.21 (m, 4H), 3.19 (s, 3H), 3.05 (d, J=9.8 Hz, 1H), 2.93-2.87 (m, 6H), 2.86 (s, 6H), 2.82 (d, J=5.4 Hz, 8H), 2.68 (d, J=6.9 Hz, 2H), 2.51 (dd, J=13.9, 11.9 Hz, 1H), 2.42 (t, J=7.2 Hz, 2H), 2.23 (dd, J=13.8, 2.6 Hz, 1H), 1.88 (d, J=5.4 Hz, 5H), 1.74 (d, J=13.7 Hz, 1H), 1.69 (s, 3H), 1.52 (s, 1H), 1.30 (d, J=6.4 Hz, 3H), 1.25-1.18 (m, 1H), 0.87 (s, 3H).

Example 9

Figure 17:
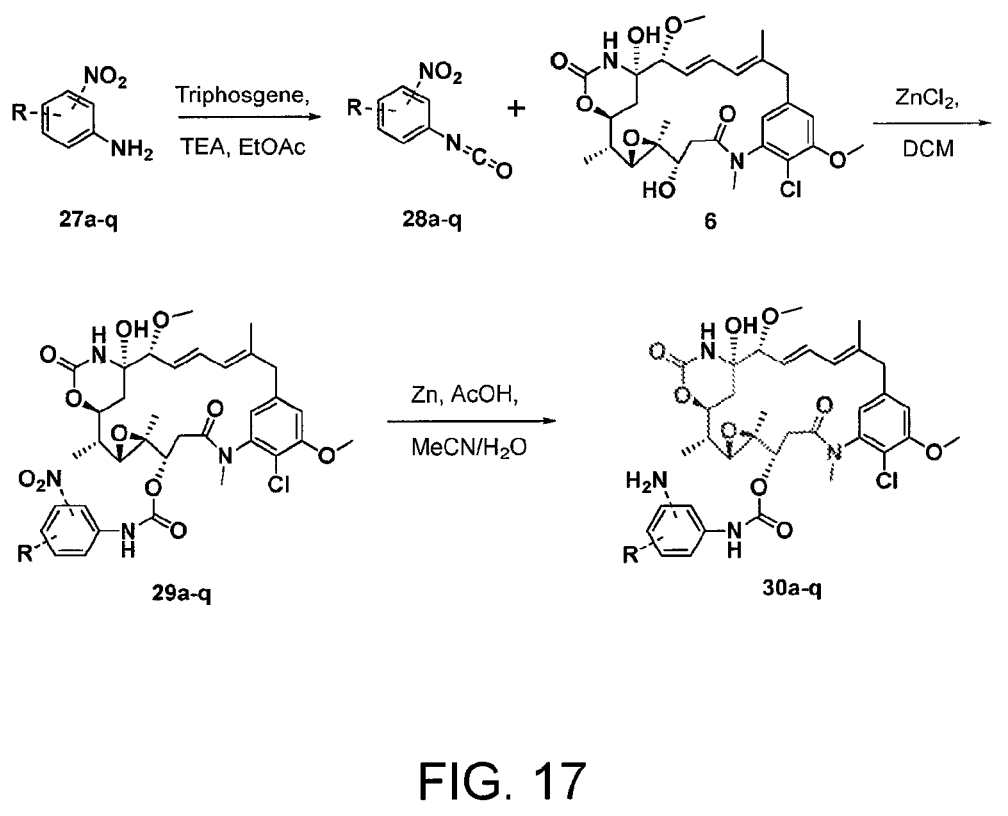

Examples 9-25 refer to compounds illustrated in FIG. 17, which is a general scheme for making payloads 30a-q.

Maytan-3-O-carbamoyl-N-(3-chloro-4-amino)benzene (30a)

Step A: 1-isocyanato-3-chloro-4-nitrobenzene (28a)

Following the procedure of Cai et al. (*Org. Lett.* 2012, 14, 3332-35), triphosgene (301 mg, 1.01 mmol) was dissolved in 2 mL of dry EtOAc, and the reaction cooled to 0° C. under Ar atmosphere. A solution of $Et_3N$ (15 µL, 0.11 mmol) and 3-chloro-4-nitroaniline (27a, 173 mg, 1.00 mmol) in 3 mL dry EtOAc was added dropwise over 20 min. The reaction flask was warmed to ambient temperature and stirred for 1h, then topped with a water condenser and heated to 80° C. for 18h. The solvent was evaporated under vacuum and the residue was washed with $Et_2O$/hexane 1:1 (3×10 mL) on a fritted filter. The filtrate was evaporated and dried in vacuo to give the title compound as a yellow solid (177 mg, 89%). $^1$H NMR (300 MHz, CDCl$_3$) δ: 7.29 (d, J=2.3 Hz, 1H), 7.14 (d, J=2.3 Hz, 1H), 7.11 (d, J=2.3 Hz, 1H).

Step B: Maytan-3-O-carbamoyl-N-(3-chloro-4-nitro)benzene (29a)

Using the method of Example 1, step C, the title compound was prepared from the product of the preceding step (28a, 87 mg, 0.438 mmol) and maytansinol (6, 103 mg, 0.182 mmol) as a light yellow solid (78 mg, 56%). MS (ESI, pos.): calc'd for $C_{35}H_{40}Cl_2N_4O_{11}$, 762.2; found 763.1 (M+H).

Step C: Maytan-3-O-carbamoyl-N-(3-chloro-4-amino)benzene (30a)

Using the method of Example 4, step B, the title compound was prepared from the product of the preceding step (29a, 77 mg, 0.101 mmol) as a white solid (59 mg, 74%). MS (ESI, pos.): calc'd for $C_{35}H_{42}Cl_2N_4O_9$, 732.2; found 733.1 (M+H). $^1$H NMR (500 MHz, Chloroform-d) δ: 7.43 (s, 1H), 7.13 (d, J=8.4 Hz, 1H), 6.83 (d, J=1.8 Hz, 1H), 6.76 (s, 1H), 6.70 (s, 1H), 6.46 (dd, J=15.4, 11.1 Hz, 2H), 6.22 (s, 1H), 6.07 (d, J=10.9 Hz, 1H), 5.38 (dd, J=15.4, 8.7 Hz, 1H), 4.78 (d, J=11.5 Hz, 1H), 4.34 (t, J=11.5 Hz, 1H), 3.99 (s, 3H), 3.98 (s, 1H), 3.53-3.44 (m, 2H), 3.32 (s, 3H), 3.26 (d, J=14.5 Hz, 1H), 3.21 (s, 3H), 2.98 (s, 1H), 2.90 (d, J=9.1 Hz, 1H), 2.50 (t, J=12.8 Hz, 1H), 2.26 (d, J=13.9 Hz, 1H), 1.87 (d, J=13.6 Hz, 1H), 1.70 (s, 3H), 1.50 (dd, J=10.8, 4.4 Hz, 2H), 1.30 (d, J=6.3 Hz, 3H), 1.24 (t, J=12.7 Hz, 1H), 0.90 (s, 3H).

Example 10

Maytan-3-O-carbamoyl-N-(4-chloro-2-amino)benzene (30b)

Step A: 1-isocyanato-4-chloro-2-nitrobenzene (28b)

Using the method of Example 9, step A, the title compound was prepared from 4-chloro-2-nitroaniline (27b, 172 mg, 0.997 mmol) as a yellow solid (198 mg, 100%). $^1$H NMR (300 MHz, Chloroform-d) δ: 8.14 (d, J=2.5 Hz, 1H), 7.57 (dd, J=8.6, 2.5 Hz, 1H), 7.21 (d, J=8.6 Hz, 1H).

Step B: Maytan-3-O-carbamoyl-N-(4-chloro-2-nitro)benzene (29b)

Using the method of Example 4, step A, the title compound was prepared from the product of the preceding step (28b, 98 mg, 0.493 mmol) and maytansinol (6, 54 mg, 0.096 mmol) as an orange solid (46 mg, 63%). MS (ESI, pos.): calc'd for $C_{35}H_{40}Cl_2N_4O_{11}$, 762.2; found 763.5 (M+H).

Step C: Maytan-3-O-carbamoyl-N-(4-chloro-2-amino)benzene (30b)

Using the method of Example 4, step B, the title compound was prepared from the product of the preceding step (29b, 44 mg, 0.058 mmol) as a white solid (34 mg, 74%). MS (ESI, pos.): calc'd for $C_{35}H_{42}Cl_2N_4O_9$, 732.2; found 733.5 (M+H). $^1$H NMR (500 MHz, Chloroform-d) δ: 7.43 (s, 1H), 7.13 (d, J=8.4 Hz, 1H), 6.83 (d, J=1.8 Hz, 1H), 6.76 (s, 1H), 6.70 (s, 1H), 6.46 (dd, J=15.4, 11.1 Hz, 2H), 6.22 (s, 1H), 6.07 (d, J=10.9 Hz, 1H), 5.38 (dd, J=15.4, 8.7 Hz, 1H), 4.78 (d, J=11.5 Hz, 1H), 4.34 (t, J=11.5 Hz, 1H), 3.99 (s, 3H), 3.98 (s, 1H), 3.54-3.44 (m, 2H), 3.32 (s, 3H), 3.26 (d, J=14.5 Hz, 1H), 3.21 (s, 3H), 2.98 (s, 1H), 2.90 (d, J=9.1 Hz, 1H), 2.50 (t, J=12.8 Hz, 1H), 2.26 (d, J=13.9 Hz, 1H), 1.87 (d, J=13.6 Hz, 1H), 1.70 (s, 3H), 1.50 (dd, J=10.8, 4.4 Hz, 2H), 1.30 (d, J=6.3 Hz, 3H), 1.24 (t, J=12.7 Hz, 1H), 0.90 (s, 3H).

Example 11

Maytan-3-O-carbamoyl-N-(2-methyl-4-amino)benzene (30c)

Step A: Maytan-3-O-carbamoyl-N-(2-methyl-4-nitro)benzene (29c)

The title compound was prepared from 2-methyl-4-nitrophenyl isocyanate (28c, 41 mg, 0.230 mmol) and maytansinol (6, 53 mg, 0.094 mmol) as a yellow solid (10 mg, 14%), using the method of Example 4, step A, except that it was purified on a C18 Aq RediSep Gold column via Teledyne ISCO purification system (gradient elution: 20-80% MeCN in water, 0.05% acetic acid in both). MS (ESI, pos.): calc'd for $C_{36}H43ClN_4O_{11}$, 742.3; found 743.2 (M+H).

Step B: Maytan-3-O-carbamoyl-N-(2-methyl-4-amino)benzene (30c)

Using the method of Example 4, step B, the title compound was prepared from the product of the preceding step (29c, 10 mg, 0.014 mmol) as a cream-colored solid (6 mg, 60%). MS (ESI, pos.): calc'd for $C_{35}H_{42}Cl_2N_4O_9$, 712.3; found 713.2 (M+H). $^1$H NMR (500 MHz, Chloroform-d) δ: 7.33-7.30 (m, 1H), 6.84 (d, J=1.8 Hz, 1H), 6.79 (s, 1H), 6.55 (d, J=2.6 Hz, 1H), 6.52 (dd, J=8.4, 2.7 Hz, 1H), 6.47 (dd, J=15.5, 10.9 Hz, 1H), 6.24 (s, 1H), 6.22-6.15 (m, 1H), 6.10 (d, J=10.9 Hz, 1H), 5.46 (dd, J=15.5, 8.9 Hz, 1H), 4.80 (dd, J=11.7, 2.4 Hz, 1H), 4.42-4.29 (m, 1H), 4.00 (s, 3H), 3.53-3.41 (m, 2H), 3.32 (s, 3H), 3.24 (d, J=13.0 Hz, 1H), 3.19 (s, 3H), 3.14 (s, 1H), 2.89 (d, J=9.8 Hz, 1H), 2.49 (dd, J=13.7, 11.7 Hz, 1H), 2.25 (s, 3H), 2.22 (d, J=2.4 Hz, 1H), 1.94 (d, J=13.6 Hz, 1H), 1.70 (s, 3H), 1.51-1.45 (m, 1H), 1.34-1.21 (m, 5H), 0.91 (s, 3H).

Example 12

Maytan-3-O-carbamoyl-N-(2-methyl-3-amino)benzene (30d)

Step A: 1-isocyanato-2-methyl-3-nitrobenzene (28d)

Using the method of Example 9, step A, the title compound was prepared from 2-methyl-3-nitroaniline (27d, 153 mg, 1.01 mmol) as a pale yellow solid (178 mg, 99%). $^1$H NMR (300 MHz, Chloroform-d) δ: 7.68 (dd, J=7.5, 1.8 Hz, 1H), 7.43-7.26 (m, 2H), 2.49 (s, 3H).

Step B: Maytan-3-O-carbamoyl-N-(2-methyl-3-nitro)benzene (29d)

Using the method of Example 4, step A, the title compound was prepared from the product of the preceding step (28d, 70 mg, 0.393 mmol) and maytansinol (6, 73 mg, 0.129 mmol) as a yellow solid (41 mg, 43%). MS (ESI, pos.): calc'd for $C_{36}H_{43}ClN_4O_{11}$, 742.3; found 743.5 (M+H).

Step C: Maytan-3-O-carbamoyl-N-(2-methyl-3-amino)benzene (30d)

The title compound was prepared from the product of the preceding step (29d, 44 mg, 0.058 mmol) as a white solid (12 mg, 29%) using the method of Example 4, step B, except that it had to be repurified by preparative HPLC on a Phenomenex Gemini 5u, 30×150 mm C18 column (20-80% MeCN in water, 0.05% HOAc both, over 15 min, 50 mL/min). MS (ESI, pos.): calc'd for $C_{36}H_{45}ClN_4O_9$, 712.3; found 713.5 (M+H). $^1$H NMR (500 MHz, DMSO-d$_6$) δ: 7.92 (s, 1H), 7.19 (d, J=1.9 Hz, 1H), 7.15 (s, 1H), 7.00 (s, 1H), 6.90 (s, 2H), 6.63-6.53 (m, 1H), 6.49 (d, J=11.1 Hz, 1H), 5.54 (dd, J=15.0, 9.1 Hz, 1H), 4.48 (dd, J=12.1, 2.7 Hz, 1H), 4.13 (t, J=11.3 Hz, 1H), 3.94 (s, 3H), 3.58 (d, J=12.2 Hz, 1H), 3.25 (s, 3H), 3.16 (d, J=12.1 Hz, 2H), 3.09 (s, 3H), 2.73 (d, J=9.7 Hz, 1H), 2.45-2.38 (m, 1H), 2.06-1.94 (m, 5H), 1.66 (s, 3H), 1.56 (d, J=13.3 Hz, 1H), 1.44 (d, J=12.2 Hz, 2H), 1.10 (d, J=6.3 Hz, 3H), 0.79 (s, 3H).

Example 13

Maytan-3-O-carbamoyl-N-(6-methyl-3-amino)benzene (30e)

Step A: 1-isocyanato-6-methyl-3-nitrobenzene (28e)

Using the method of Example 9, step A, the title compound was prepared from 6-methyl-3-nitroaniline (27e, 1.00 mmol) as a yellow solid (100 mg, 56% yield). $^1$H NMR (500 MHz, Chloroform-d) δ: 7.98 (d, 1H, J=2.5 Hz), 7.95 (dd, 1H, J=2.5, 8.5 Hz), 7.36 (d, 1H, J=8.5 Hz).

Step B: Maytan-3-O-carbamoyl-N-(6-methyl-3-nitro)benzene (29e)

The title compound was prepared from the product of the preceding step (28e, 0.422 mmol) and maytansinol (6, 100 mg, 0.176 mmol) as a yellow solid (21 mg, 16% yield) using the method of Example 1, step C, except that it was purified on a C18 Aq RediSep Gold column via ISCO (gradient elution: 20-80% MeCN in water, 0.05% acetic acid in both). MS (ESI, pos.): calc'd for $C_{36}H_{43}ClN_4O_{11}$, 742.3; found 725.2 (M+H−H2O), 765.2 (M+Na).

Step C: Maytan-3-O-carbamoyl-N-(6-methyl-3-amino)benzene (30e)

Using the method of Example 4, step B, the title compound was prepared from the product of the preceding step (29e, 21 mg, 0.028 mmol) as a white solid (6.0 mg, 29% yield). MS (ESI, pos.): calc'd for $C_{36}H_{45}ClN_4O_9$, 712.3, found 713.3 (M+H), 695.3 (M+H−H2O). $^1$H NMR (500 MHz, CDCl$_3$): δ 7.25-7.22 (m, 1H), 6.96 (d, 1H, J=7.5 Hz), 6.84 (s, 1H), 6.77 (s, 1H), 6.45-6.40 (m, 1H), 6.26 (s, 1H), 6.10 (d, 1H, J=11.0 Hz), 5.35 (dd, 1H, J=8.5, 11.7 Hz), 4.77 (dd, 1H, J=2.5, 11.7 Hz), 4.37 (dd, 1H, J=10.5, 10.5 Hz), 3.99 (s, 3H), 3.48 (d, 1H, J=13.5 Hz), 3.45 (d, 1H, J=9.0 Hz), 3.28 (s, 3H), 3.24 (d, 1H, J=13.5 Hz), 3.19 (s, 3H), 2.97 (d, 1H, J=10.0 Hz), 2.50 (dd, 1H, J=11.5, 11.5 Hz), 2.28-2.22 (m, 4H), 1.86 (d, 1H, J=13.5 Hz), 1.70 (s, 3H), 1.53-1.49 (m, 1H), 1.31 (s, 3H), 1.27-1.22 (m, 1H), 0.89 (s, 3H).

Example 14

Maytan-3-O-carbamoyl-N-(6-methyl-2-amino)benzene (30f)

Step A: 1-isocyanato-6-methyl-2-nitrobenzene (28f)

Using the method of Example 9, step A, the title compound was prepared from 6-methyl-2-nitroaniline (27f, 1.00 mmol) as a yellow solid (135 mg, 76% yield). $^1$H NMR (500 MHz, CDCl$_3$): δ 7.92 (d, 1H, J=8.5 Hz), 7.49 (d, 1H, J=8.5 Hz), 7.22 (dd, 1H, J=8.5, 8.5 Hz), 2.43 (s, 3H).

Step B: Maytan-3-O-carbamoyl-N-(6-methyl-2-nitro)benzene (29f)

Using the method of Example 13, step B, the title compound was prepared from the product of the preceding step (28f, 0.422 mmol) and maytansinol (6, 100 mg, 0.176 mmol) as a yellow solid (33 mg, 25% yield). MS (ESI, pos.): calc'd for C$_{36}$H43ClN$_4$O$_{11}$, 742.3; found 743.2 (M+H).

Step C: Maytan-3-O-carbamoyl-N-(6-methyl-2-amino)benzene (30f)

Using the method of Example 4, step B, the title compound was prepared from the product of the preceding step (29f, 33 mg, 0.044 mmol) as a yellow solid (15.0 mg, 53% yield). MS (ESI, pos.): calc'd for C$_{36}$H$_{45}$ClN$_4$O$_9$, 712.3, found 713.30 (M+H). $^1$H NMR (500 MHz, CDCl$_3$): δ 7.01-6.98 (m, 1H), 6.83 (s, 1H), 6.78 (s, 1H), 6.67-6.62 (m, 2H), 6.50-6.45 (m, 1H), 6.35 (bs, 1H), 6.16 (d, 1H, J=11.0 Hz), 5.98 (s, 1H), 5.63 (dd, 1H, J=8.5, 14.7 Hz), 4.96 (d, 1H, J=11.5 Hz), 4.28 (dd, 1H, J=10.5, 10.5 Hz), 3.98 (s, 3H), 3.50-3.45 (m, 2H), 3.32 (s, 3H), 3.21 (d, 1H, J=13.5 Hz), 3.18 (s, 3H), 2.81 (d, 1H, J=10.0 Hz), 2.54 (dd, 1H, J=13.5, 13.5 Hz), 2.25-2.23 (m, 4H), 1.90 (d, 1H, J=12.5 Hz), 1.70 (s, 3H), 1.52-1.48 (m, 1H), 1.35-1.27 (m, 4H), 0.92 (s, 3H).

Example 15

Maytan-3-O-carbamoyl-N-(4-fluoro-2-amino)benzene (30 g)

Step A: 1-isocyanato-4-fluoro-2-nitrobenzene (28 g)

Using the method of Example 9, step A, the title compound was prepared from 4-fluoro-2-nitroaniline (27 g, 1.00 mmol) as an orange solid (223 mg, 81% yield). $^1$H NMR (300 MHz, CDCl$_3$): δ 7.88 (dd, 1H, J=3.0, 7.5 Hz), 7.33 (dd, 1H, J=3.0, 7.5 Hz), 7.25 (dd, 1H, J=4.0, 9.0 Hz).

Step B: Maytan-3-O-carbamoyl-N-(4-fluoro-2-nitro)benzene (29 g)

Using the method of Example 13, step B, the title compound was prepared from the product of the preceding step (28 g, 0.422 mmol) and maytansinol (6, 10 mg, 0.176 mmol) as a yellow solid (16 mg, 12% yield). MS (ESI, pos.): calc'd for C$_{35}$H$_{40}$ClFN$_4$O$_1$, 746.2; found 747.2 (M+H).

Step C: Maytan-3-O-carbamoyl-N-(4-fluoro-2-amino)benzene (30 g)

Using the method of Example 4, step B, the title compound was prepared from the product of the preceding step (29 g, 16 mg, 0.021 mmol) as a yellow solid (4.0 mg, 26% yield). MS (ESI, pos.): calc'd for C$_{35}$H$_{42}$ClFN$_4$O$_9$, 716.3; found 717.2 (M+H). $^1$H NMR (500 MHz, CDCl$_3$): δ 7.25-7.21 (m, 1H), 6.83 (s, 1H), 6.73 (bs, 1H), 6.52 (dd, 1H, J=2.5, 8.5 Hz), 6.50-6.48 (2H, m), 6.39 (s, 1H), 6.27 (s, 1H), 6.11 (1H, bs), 5.52 (dd, 1H, J=8.5, 15.7 Hz), 4.87 (dd, 1H, J=2.5, 11.5 Hz), 4.27 (dd, 1H, J=11.5, 11.5 Hz), 3.99 (s, 3H), 3.49 (d, 1H, J=8.5 Hz), 3.45 (bs, 1H), 3.34 (s, 3H), 3.21 (s, 3H), 3.18 (bs, 1H), 2.84-2.83 (m, 1H), 2.52 (dd, 1H, J=11.5, 13.5 Hz), 2.28 (d, 1H, J=13.5 Hz), 1.86 (d, 1H, J=13.5 Hz), 1.68 (s, 3H), 1.51-1.45 (m, 1H), 1.27 (d, 3H, J=6.5 Hz), 1.27-1.23 (m, 1H), 0.89 (s, 3H).

Example 16

Maytan-3-O-carbamoyl-N-(2-fluoro-5-amino)benzene (30h)

Step A: 1-isocyanato-2-fluoro-5-nitrobenzene (28h)

Using the method of Example 9, step A, the title compound was prepared from 2-fluoro-5-nitroaniline (27h, 155 mg, 0.99 mmol) as an orange solid (168 mg, 93% yield). $^1$H NMR (300 MHz, Chloroform-d) δ: 8.10 (dd, J=8.7, 4.1 Hz, 1H), 8.01 (dd, J=6.7, 2.8 Hz, 1H), 7.31 (t, J=8.8 Hz, 1H).

Step B: Maytan-3-O-carbamoyl-N-(2-fluoro-5-nitro)benzene (29h)

Using the method of Example 13, step B, the title compound was prepared from the product of the preceding step (28h, 61 mg, 0.335 mmol) and maytansinol (6, 67 mg, 0.119 mmol) as an orange solid (21 mg, 24% yield). MS (ESI, pos.): calc'd for C$_{35}$H$_{40}$ClFN$_4$O$_{11}$, 746.2; found 747.5 (M+H).

Step C: Maytan-3-O-carbamoyl-N-(2-fluoro-5-amino)benzene (30h)

Using the method of Example 4, step B, the title compound was prepared from the product of the preceding step (29h, 20 mg, 0.027 mmol) as a white solid (6 mg, 29% yield) after a second reverse-phase ISCO purification (gradient elution: 30-90% MeCN in water, 0.05% acetic acid in both). MS (ESI, pos.): calc'd for C$_{35}$H$_{42}$ClFN$_4$O$_9$, 716.3; found 717.5 (M+H). $^1$H NMR (500 MHz, DMSO-d$_6$) δ: 7.70 (s, 1H), 7.19 (d, J=1.9 Hz, 1H), 7.07 (s, 1H), 7.03 (dd, J=7.0, 2.8 Hz, 1H), 6.90 (dd, J=10.6, 8.7 Hz, 1H), 6.81 (s, 1H), 6.56 (dd, J=15.3, 11.1 Hz, 1H), 6.38 (d, J=11.1 Hz, 1H), 6.32 (dt, J=8.7, 3.3 Hz, 1H), 5.59 (s, 1H), 5.49 (dd, J=15.2, 9.1 Hz, 1H), 4.90 (s, 2H), 4.50 (dd, J=11.7, 2.5 Hz, 1H), 4.14 (t, J=11.2 Hz, 1H), 3.94 (s, 3H), 3.56 (d, J=12.4 Hz, 1H), 3.48 (d, J=9.1 Hz, 1H), 3.23 (s, 3H), 3.07 (s, 3H), 2.79 (d, J=9.7 Hz, 1H), 2.44 (dd, J=14.0, 11.9 Hz, 2H), 2.03 (d, J=13.7 Hz, 1H), 1.66 (s, 3H), 1.52 (d, J=13.5 Hz, 1H), 1.44 (dd, J=18.3, 10.2 Hz, 2H), 1.12 (d, J=6.3 Hz, 3H), 0.80 (s, 3H).

Example 17

Maytan-3-O-carbamoyl-N-(4-methoxy-2-amino)benzene (30i)

Step A: 1-isocyanato-4-methoxy-2-nitrobenzene (28i)

Using the method of Example 9, step A, the title compound was prepared from 4-methoxy-2-nitroaniline (27i, 1.00 mmol) as a yellow solid (100 mg, 51% yield). $^1$H NMR (300 MHz, CDCl$_3$): δ 8.10 (dd, 1H, J=3.0, 8.7 Hz), 7.90 (d, 1H, J=3.0 Hz), 6.96 (d, 1H, J=8.7 Hz), 4.06 (s, 3H).

Step B: Maytan-3-O-carbamoyl-N-(4-methoxy-2-nitro)benzene (29i)

Using the method of Example 13, step B, the title compound was prepared from the product of the preceding step (28i, 0.422 mmol) and maytansinol (6, 100 mg, 0.176 mmol) as a yellow solid (25 mg, 19% yield). MS (ESI, pos.): calc'd for C$_{36}$H$_{43}$ClN$_4$O$_{12}$, 758.3; found 759.2 (M+H).

Step C: Maytan-3-O-carbamoyl-N-(4-methoxy-2-amino)benzene (30i)

Using the method of Example 4, step B, the title compound was prepared from the product of the preceding step (29i, 25 mg, 0.033 mmol) as a yellow solid (2.0 mg, 9% yield). MS (ESI, pos.): calc'd for C$_{36}$H$_{45}$ClN$_4$O$_{10}$, 728.3; found 729.2 (M+H). $^1$H NMR (500 MHz, CDCl$_3$): S 7.14 (d, 1H, J=8.5 Hz), 6.83 (s, 1H), 6.49-6.38 (m, 2H), 6.30 (s, 1H), 6.20 (bs, 1H), 5.55-5.51 (m, 1H), 4.89 (d, 1H, J=11 Hz), 4.30 (dd, 1H, J=11.0, 11.0 Hz), 3.99 (s, 3H), 3.76 (s, 3H), 3.49-3.48 (m, 1H), 3.33 (s, 3H), 3.20-3.17 (m, 1H), 3.21 (s, 3H), 2.84 (m, 1H), 2.54-2.49 (m, 1H), 2.25 (d, 1H, J=13.5 Hz), 1.90 (d, 1H, J=13.5 Hz), 1.69 (s, 3H), 1.69-1.57 (m, 2H), 1.29 (s, 3H), 0.91 (s, 3H).

Example 18

Maytan-3-O-carbamoyl-N-(3-methoxy-4-amino) benzene (30j)

Step A: 1-isocyanato-3-methoxy-4-nitrobenzene (28j)

Using the method of Example 9, step A, the title compound was prepared from 3-methoxy-4-nitroaniline (27j, 169 mg, 1.00 mmol) as a yellow solid (102 mg, 52% yield). $^1$H NMR (300 MHz, Chloroform-d) δ: 8.01-7.81 (m, 1H), 6.85-6.65 (m, 2H), 3.96 (s, 4H).

Step B: Maytan-3-O-carbamoyl-N-(3-methoxy-4-nitro)benzene (29j)

The title compound was prepared from the product of the preceding step (28j, 100 mg, 0.515 mmol) and maytansinol (6, 71 mg, 0.126 mmol) as a yellow solid (64 mg, 67%) using the method of Example 4, step A, except that the reaction was run at ambient temperature for 18 h. MS (ESI, pos.): calc'd for C$_{36}$H$_{43}$ClN$_4$O$_{12}$, 758.3; found 759.5 (M+H).

Step C: Maytan-3-O-carbamoyl-N-(3-methoxy-4-amino)benzene (30j)

Using the method of Example 4, step B, the title compound was prepared from the product of the preceding step (29j, 63 mg, 0.083 mmol) as a white solid (37 mg, 57%). MS (ESI, pos.): calc'd for C$_{36}$H$_{45}$ClN$_4$O$_{10}$, 728.3; found 729.5 (M+H). $^1$H NMR (500 MHz, Chloroform-d) δ: 6.84 (d, J=1.8 Hz, 1H), 6.71 (s, 1H), 6.66 (d, J=8.2 Hz, 1H), 6.56 (dd, J=8.2, 2.3 Hz, 1H), 6.52-6.38 (m, 2H), 6.22 (s, 1H), 6.13 (d, J=10.9 Hz, 1H), 5.41 (dd, J=15.5, 8.6 Hz, 1H), 4.78 (d, J=11.3 Hz, 1H), 4.33 (t, J=11.2 Hz, 1H), 3.99 (s, 3H), 3.87 (s, 3H), 3.55-3.39 (m, 2H), 3.31 (s, 3H), 3.27 (d, J=13.3 Hz, 1H), 3.19 (s, 3H), 2.90 (d, J=9.8 Hz, 1H), 2.49 (dd, J=13.9, 11.6 Hz, 1H), 2.25 (d, J=14.0 Hz, 1H), 2.11 (s, 2H), 1.87 (d, J=13.4 Hz, 1H), 1.70 (s, 3H), 1.30 (d, J=6.2 Hz, 3H), 1.25 (dd, J=15.1, 10.5 Hz, 1H), 0.90 (s, 3H).

Example 19

Maytan-3-O-carbamoyl-N-(2-methoxy-4-amino) benzene (30k)

Step A: Maytan-3-O-carbamoyl-N-(2-methoxy-4-nitro)benzene (29k)

The title compound was prepared from 1-isocyanato-2-methoxy-4-nitrobenzene (28k, 62 mg, 0.319 mmol) and maytansinol (6, 53 mg, 0.094 mmol) as a pale yellow solid (25 mg, 35%) using the method of Example 4, step A, except that the reaction was purified on a C18 Aq RediSep Gold column via ISCO (gradient elution: 20-80% MeCN in water, 0.05% acetic acid in both). MS (ESI, pos.): calc'd for C$_{36}$H$_{43}$ClN$_4$O$_{12}$, 758.3; found 759.5 (M+H).

Step B: Maytan-3-O-carbamoyl-N-(2-methoxy-4-amino)benzene (30k)

Using the method of Example 4, step B, the title compound was prepared from the product of the preceding step (29k, 24 mg, 0.032 mmol) as a white solid (9 mg, 36%). MS (ESI, pos.): calc'd for C$_{36}$H$_{45}$ClN$_4$O$_{10}$, 728.3; found 729.5 (M+H), 751.5 (M+Na). $^1$H NMR (500 MHz, Chloroform-d) δ: 7.83 (d, J=8.3 Hz, 1H), 6.90 (s, 1H), 6.86 (d, J=1.9 Hz, 1H), 6.82 (d, J=1.8 Hz, 1H), 6.42 (dd, J=15.1, 10.9 Hz, 1H), 6.36-6.24 (m, 2H), 6.15 (s, 1H), 5.31 (dd, J=15.1, 9.1 Hz, 1H), 4.79 (dd, J=11.8, 2.4 Hz, 1H), 4.41-4.29 (m, 1H), 4.00 (s, 3H), 3.94 (s, 3H), 3.52 (d, J=12.9 Hz, 1H), 3.41 (d, J=9.1 Hz, 1H), 3.29 (d, J=12.7 Hz, 1H), 3.25 (s, 3H), 3.19 (s, 3H), 3.02 (d, J=9.9 Hz, 1H), 2.73 (s, 1H), 2.47 (dd, J=13.8, 11.8 Hz, 1H), 2.22 (dd, J=13.7, 2.4 Hz, 1H), 2.13 (s, 2H), 1.78 (d, J=13.6 Hz, 1H), 1.70 (s, 3H), 1.50 (dd, J=10.2, 6.4 Hz, 1H), 1.30 (d, J=6.4 Hz, 3H), 1.20 (t, J=12.9 Hz, 1H), 0.86 (s, 3H).

Example 20

Maytan-3-O-carbamoyl-N-(3-trifluoromethyl-4-amino)benzene (30l)

Step A: 1-isocyanato-3-trifluoromethyl-4-nitrobenzene (28l)

Using the method of Example 9, step A, the title compound was prepared from 3-trifluoromethyl-4-nitroaniline (27l, 103 mg, 0.500 mmol) as a yellow oily solid (63 mg, 54% yield). $^1$H NMR (300 MHz, Chloroform-d) δ: 7.95 (d, J=8.7 Hz, 1H), 7.53 (dt, J=2.4, 0.5 Hz, 1H), 7.41 (ddd, J=8.7, 2.3, 0.5 Hz, 1H).

Step B: Maytan-3-O-carbamoyl-N-(3-trifluoromethyl-4-nitro)benzene (29l)

The title compound was prepared from the product of the preceding step (28l, 59 mg, 0.254 mmol) and maytansinol (6, 57 mg, 0.101 mmol) as a yellow solid (27 mg, 34%) using the method of Example 19, step A. MS (ESI, pos.): calc'd for C$_{36}$H$_{40}$ClF$_3$N$_4$O$_{11}$, 796.2; found 797.4 (M+H).

Step C: Maytan-3-O-carbamoyl-N-(3-trifluoromethyl-4-amino)benzene (30l)

Using the method of Example 4, step B, the title compound was prepared from the product of the preceding step (291, 25 mg, 0.031 mmol) as a white solid (16 mg, 62%) after a second reverse-phase ISCO purification. MS (ESI, pos.): calc'd for $C_{36}H_{42}ClF_3N_4O_9$, 766.3; found 767.5 (M+H). $^1H$ NMR (500 MHz, Chloroform-d) δ: 7.47 (dd, J=8.7, 2.6 Hz, 1H), 7.40 (d, J=2.5 Hz, 1H), 6.84 (d, J=1.9 Hz, 1H), 6.73 (d, J=8.7 Hz, 1H), 6.71-6.61 (m, 1H), 6.50 (d, J=2.3 Hz, 1H), 6.49-6.42 (m, 1H), 6.22 (s, 1H), 6.06 (d, J=10.9 Hz, 1H), 5.37 (dd, J=15.5, 8.5 Hz, 1H), 4.79 (dd, J=11.5, 2.2 Hz, 1H), 4.32 (ddd, J=12.2, 10.5, 1.9 Hz, 1H), 4.11 (s, 2H), 3.99 (s, 3H), 3.54-3.44 (m, 2H), 3.32 (s, 3H), 3.26 (d, J=13.5 Hz, 1H), 3.20 (s, 3H), 2.97 (s, 1H), 2.88 (d, J=9.8 Hz, 1H), 2.50 (dd, J=14.0, 11.6 Hz, 1H), 2.27 (dd, J=14.0, 2.3 Hz, 1H), 1.86 (d, J=13.5 Hz, 1H), 1.71 (s, 3H), 1.50 (td, J=10.2, 6.3 Hz, 1H), 1.29 (d, J=6.4 Hz, 3H), 1.25 (t, J=12.6 Hz, 1H), 0.90 (s, 3H).

Example 21

Maytan-3-O-carbamoyl-N-(2-bromo-4-amino)benzene (30m)

Step A: 1-isocyanato-2-bromo-4-nitrobenzene (28m)

Using the method of Example 9, step A, the title compound was prepared from 2-bromo-4-nitroaniline (27m, 108 mg, 0.498 mmol) as a yellow solid (109 mg, 90% yield). $^1H$ NMR (300 MHz, Chloroform-d) δ: 8.49 (d, J=2.5 Hz, 1H), 8.16 (dd, J=8.8, 2.6 Hz, 1H), 7.28 (dd, J=8.8, 0.3 Hz, 1H).

Step B: Maytan-3-O-carbamoyl-N-(2-bromo-4-nitro)benzene (29m)

The title compound was prepared from the product of the preceding step (28m, 55 mg, 0.226 mmol) and maytansinol (6, 46 mg, 0.081 mmol) as a yellow solid (30 mg, 45%) using the method of Example 19, step A. MS (ESI, pos.): calc'd for $C_{35}H_{40}BrClN_4O_{11}$, 806.2; found 809.0 (M+H).

Step C: Maytan-3-O-carbamoyl-N-(2-bromo-4-amino)benzene (30m)

Using the method of Example 4, step B, the title compound was prepared from the product of the preceding step (29m, 28 mg, 0.035 mmol) as a white solid (10 mg, 34%). MS (ESI, pos.): calc'd for $C_{35}H_{42}BrClN_4O_9$, 776.2; found 779.0 (M+H). $^1H$ NMR (300 MHz, Chloroform-d) δ: 7.79 (d, J=8.7 Hz, 1H), 6.94 (d, J=1.8 Hz, 1H), 6.90 (d, J=2.5 Hz, 1H), 6.85 (d, J=1.8 Hz, 1H), 6.77 (s, 1H), 6.64 (dd, J=8.8, 2.6 Hz, 1H), 6.50-6.29 (m, 2H), 6.19 (s, 1H), 5.22 (dd, J=14.6, 9.0 Hz, 1H), 4.79 (dd, J=11.8, 2.6 Hz, 1H), 4.38 (t, J=11.1 Hz, 1H), 4.00 (s, 3H), 3.69 (s, 1H), 3.60 (d, J=12.9 Hz, 1H), 3.43 (d, J=9.0 Hz, 1H), 3.26 (s, 4H), 3.20 (s, 4H), 3.05 (d, J=9.8 Hz, 1H), 2.89 (s, 1H), 2.49 (dd, J=13.7, 11.9 Hz, 1H), 2.22 (dd, J=13.7, 2.6 Hz, 1H), 1.79 (d, J=13.5 Hz, 1H), 1.69 (s, 4H), 1.49 (dd, J=10.3, 6.2 Hz, 1H), 1.31 (d, J=6.3 Hz, 3H), 1.28-1.16 (m, 2H), 0.87 (s, 3H).

Example 22

Maytan-3-O-carbamoyl-N-(4-trifluoromethoxy-2-amino)benzene (30n)

Step A: 1-isocyanato-4-trifluoromethoxy-2-nitrobenzene (28n)

Using the method of Example 9, step A, the title compound was prepared from 4-trifluoromethoxy-2-nitroaniline (27n, 223 mg, 1.00 mmol) as an orange oily solid (228 mg, 92% yield). $^1H$ NMR (300 MHz, Chloroform-d) δ: 8.03 (d, J=2.8 Hz, 1H), 7.52-7.44 (m, 1H), 7.32 (dt, J=9.0, 0.6 Hz, 1H).

Step B: Maytan-3-O-carbamoyl-N-(4-trifluoromethoxy-2-nitro)benzene (29n)

The title compound was prepared from the product of the preceding step (28n, 215 mg, 0.867 mmol) and maytansinol (6, 84 mg, 0.149 mmol) as a yellow solid (87 mg, 72%) using the method of Example 4, step A. MS (ESI, pos.): calc'd for $C_{36}H_{40}ClF_3N_4O_{12}$, 812.2; found 813.5 (M+H), 835.4 (M+Na).

Step C: Maytan-3-O-carbamoyl-N-(4-trifluoromethoxy-2-amino)benzene (30n)

Using the method of Example 4, step B, the title compound was prepared from the product of the preceding step (29n, 85 mg, 0.105 mmol) as a white solid (59 mg, 67%) after a second reverse-phase ISCO purification. MS (ESI, pos.): calc'd for $C_{36}H_{42}ClF_3N_4O_{10}$, 782.3; found 783.5 (M+H), 805.5 (M+Na). $^1H$ NMR (500 MHz, Chloroform-d) δ: 7.31 (d, J=8.8 Hz, 1H), 6.81 (s, 1H), 6.70 (s, 1H), 6.63 (m, 2H), 6.43 (dd, J=15.4, 10.9 Hz, 1H), 6.09 (s, 1H), 5.58 (dd, J=15.4, 8.8 Hz, 1H), 4.88-4.77 (m, 1H), 4.28 (t, J=11.2 Hz, 1H), 3.96 (s, 3H), 3.44 (d, J=8.7 Hz, 2H), 3.39 (p, J=1.7 Hz, 2H), 3.33 (s, 3H), 3.19 (s, 3H), 3.15 (d, J=13.1 Hz, 1H), 2.84 (d, J=9.6 Hz, 1H), 2.57-2.47 (m, 1H), 2.28-2.22 (m, 1H), 1.84 (d, J=13.7 Hz, 1H), 1.65 (s, 3H), 1.54-1.43 (m, 1H), 1.30 (d, J=12.6 Hz, 1H), 1.26 (d, J=6.2 Hz, 3H), 0.87 (s, 3H).

Example 23

Maytan-3-O-carbamoyl-N-(4-fluoro-5-chloro-2-amino)benzene (30o)

Step A: 1-isocyanato-4-fluoro-5-chloro-2-nitrobenzene (28o)

Using the method of Example 9, step A, the title compound was prepared from 4-fluoro-5-chloro-2-nitroaniline (27o, 70 mg, 0.367 mmol) as a yellow oil (72 mg, 91% yield). $^1H$ NMR (300 MHz, Chloroform-d) δ: 8.01 (d, J=8.3 Hz, 1H), 7.35 (d, J=6.5 Hz, 1H).

Step B: Maytan-3-O-carbamoyl-N-(4-fluoro-5-chloro-2-nitro)benzene (29o)

Using the method of Example 4, step B, the title compound was prepared from the product of the preceding step (28o, 70 mg, 0.323 mmol) and maytansinol (6, 48 mg, 0.085 mmol) as a yellow solid (35 mg, 53% yield). MS (ESI, pos.): calc'd for $C_{35}H_{39}Cl_2FN_4O_{11}$, 780.2; found 781.4 (M+H).

Step C: Maytan-3-O-carbamoyl-N-(4-fluoro-5-chloro-2-amino)benzene (30o)

Using the method of Example 4, step B, the title compound was prepared from the product of the preceding step (29o, 34 mg, 0.044 mmol) as a white solid (21 mg, 60% yield). MS (ESI, pos.): calc'd for $C_{35}H_{41}Cl_2FN_4O_9$, 750.2; found 751.5 (M+H); $^1H$ NMR (500 MHz, DMSO-d) δ: 7.97 (s, 1H), 7.19 (s, 1H), 6.91 (s, 1H), 6.73 (d, J=11.4 Hz, 1H), 6.66-6.30 (m, 2H), 5.84 (s, 1H), 5.52 (dd, J=14.9, 9.3 Hz, 1H), 5.17 (s, 2H), 4.52 (d, J=11.8 Hz, 1H), 4.15 (t, J=11.1

Hz, 1H), 3.94 (s, 3H), 3.47 (d, J=9.2 Hz, 1H), 3.24 (s, 3H), 3.17 (d, J=12.2 Hz, 1H), 3.10 (s, 3H), 2.75 (d, J=9.9 Hz, 1H), 2.43 (d, J=13.4 Hz, 1H), 2.08 (d, J=13.7 Hz, 1H), 1.81 (s, 1H), 1.66 (s, 3H), 1.52 (d, J=13.5 Hz, 1H), 1.45 (t, J=12.9 Hz, 2H), 1.11 (d, J=6.3 Hz, 3H), 0.77 (s, 3H).

Example 24

Maytan-3-O-carbamoyl-N-(4-amino-2-methyl-5-morpholin-4-yl)benzene (30p)

Step A: (4-nitro-2-methyl-5-morpholin-4-yl)phenyl isocyanate (28p)

Using the procedure of Example 9, step A, the title compound was prepared from 2-methyl-5-morpholin-4-yl-4-nitrophenylamine (237 mg, 1.00 mmol) as a bright orange solid (230 mg, 87% yield). $^1$H NMR (500 MHz, CDCl$_3$): δ 7.72 (s, 1H), 6.79 (s, 1H), 3.84 (t, 4H, J=5 Hz), 3.01 (t, 4H, J=5 Hz), 2.31 (s, 3H).

Step B: Maytan-3-O-carbamoyl-N-(4-nitro-2-methyl-5-morpholin-4-yl)benzene (29p)

Using the method of Example 19, step A, the title compound was prepared from the product of the preceding step (28p, 56 mg, 0.21 mmol) and maytansinol (6, 50 mg, 0.09 mmol) as an off-white solid (8 mg, 11%). MS (ESI, pos.): calc'd for C$_{40}$H$_{50}$ClN$_5$O$_{12}$, 827.3; found 828.2 (M+H).

Step C: Maytan-3-O-carbamoyl-N-(4-amino-2-methyl-5-morpholin-4-vi)benzene (30p)

Using the method of Example 4, step B, the title compound was prepared from the product of the preceding step (29p, 8 mg, 0.01 mmol) as a white solid (3.2 mg, 42%). MS (ESI, pos.): calc'd for C$_{40}$H$_{52}$ClN$_5$O$_{10}$, 797.3; found 798.2 (M+H), 820.2 (M+Na). $^1$H NMR (500 MHz, DMSO-d$_6$) δ: 7.54 (s, 1H), 7.17 (s, 2H), 6.88 (s, 1H), 6.84 (s, 1H), 6.62-6.52 (m, 2H), 6.51 (s, 1H), 5.69-5.51 (m, 2H), 4.69 (s, 2H), 4.45 (dd, J=12.0, 2.7 Hz, 1H), 4.16 (t, J=10.9 Hz, 1H), 3.93 (s, 3H), 3.73 (t, J=4.8 Hz, 4H), 3.64 (d, J=12.3 Hz, 1H), 3.53-3.44 (m, 1H), 3.25 (s, 3H), 3.14 (d, J=12.2 Hz, 1H), 3.05 (s, 3H), 2.77 (q, J=4.2, 3.2 Hz, 4H), 2.69 (d, J=9.6 Hz, 1H), 2.40 (d, J=12.7 Hz, 1H), 2.01 (s, 3H), 1.97 (d, J=13.4 Hz, 1H), 1.65 (s, 3H), 1.56 (d, J=13.6 Hz, 1H), 1.42 (t, J=12.9 Hz, 2H), 1.09 (d, J=6.4 Hz, 3H), 0.78 (s, 3H).

Example 25

Maytan-3-O-carbamoyl-N-(4-amino-2-methyl-5-pyrrolidin-1-yl)benzene (30q)

Step A: (4-nitro-2-methyl-5-pyrrolidin-1-yl)phenyl isocyanate (28q)

Using the procedure of Example 9, step A, the title compound was prepared from 2-methyl-4-nitro-5-pyrrolidin-1-yl-phenylamine (221 mg, 1.00 mmol) as a bright orange solid (210 mg, 85% yield). $^1$H-NMR (300 MHz, CDCl$_3$): δ 7.65 (s, 1H), 6.59 (s, 1H), 3.25-3.14 (m, 4H), 2.00-1.94 (m, 4H).

Step B: Maytan-3-O-carbamoyl-N-(4-nitro-2-methyl-5-pyrrolidin-1-yl)phenyl (29q)

Using the method of Example 19, step A, the title compound was prepared from the product of the preceding step (28q, 53 mg, 0.21 mmol) and maytansinol (6, 50 mg, 0.09 mmol) as an off-white solid (28 mg, 39%). MS (ESI, pos.): calc'd for C$_{40}$H$_{50}$ClN$_5$O$_{11}$, 811.3; found 812.2 (M+H).

Step C: Maytan-3-O-carbamoyl-N-(4-amino-2-methyl-5-pyrrolidin-1-yl)benzene (30q)

Using the method of Example 4, step B, the title compound was prepared from the product of the preceding step (29q, 28 mg, 0.03 mmol) as a white solid (8.6 mg, 32%). MS (ESI, pos.): calc'd for C$_{40}$H$_{52}$ClN$_5$O$_9$, 781.3; found 782.2 (M+H), 804.2 (M+Na). $^1$H NMR (500 MHz, DMSO-d) δ: 7.53 (s, 1H), 7.19 (s, 2H), 6.93-6.86 (m, 1H), 6.83 (s, 1H), 6.66-6.50 (m, 2H), 6.49 (s, 1H), 5.62 (dd, J=14.6, 9.2 Hz, 1H), 5.56 (s, 1H), 4.54 (s, 2H), 4.47 (dd, J=12.0, 2.7 Hz, 1H), 4.17 (t, J=11.1 Hz, 1H), 3.94 (s, 3H), 3.65 (d, J=12.2 Hz, 1H), 3.55-3.45 (m, 1H), 3.25 (s, 3H), 3.15 (d, J=12.2 Hz, 1H), 3.07 (s, 3H), 2.93 (d, J=6.7 Hz, 4H), 2.70 (d, J=9.7 Hz, 1H), 2.41 (d, J=12.9 Hz, 1H), 2.02 (s, 3H), 1.98 (d, J=13.2 Hz, 1H), 1.89-1.76 (m, 4H), 1.66 (s, 3H), 1.58 (d, J=13.5 Hz, 1H), 1.43 (t, J=12.9 Hz, 2H), 1.10 (d, J=6.4 Hz, 3H), 0.79 (s, 3H).

Example 26

Conjugate Preparation and Characterization

Five antibodies were conjugated to the linker-payload compounds of the disclosure using the procedure below. The four targeting antibodies used in these experiments were: (1) a PSMA antibody having the heavy and light chain variable domains of clone AB-PG1-XG1-006 as set forth in International Patent Application Publication No. WO2007/002222 A2, entitled PSMA ANTIBODY-DRUG CONJUGATES, (2) anti-MUC16 antibody having variable regions derived from clone 3A5 from International Patent Application Publication No. WO2007001851, entitled COMPOSITIONS AND METHODS FOR THE DIAGNOSIS AND TREATMENT OF TUMOR, (3) anti-HER2 antibody having variable regions derived from humAb4D5-8 from Carter et al, PNAS 1992 89 4285, and (4) an anti-STEAP2 antibody. These patent application publications and journal citations are herein incorporated by reference in their entirety for all purposes. All the monoclonal antibodies were expressed in CHO cells and purified by Protein A. A non-binding isotype control (5) derived from an immunological antigen having no relation to oncology was also used.

Method A: The antibody (10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative (for linker-payloads 9, 19, or 24; 1.2 equivalents/SH group) in DMSO (10 mg/ml) was added to the reduced antibody and the mixture adjusted to pH 7.0 with 1 M HEPES (pH 7.4). The conjugation reaction was optionally quenched with N-ethyl maleimide (NEM). The conjugates were purified by size exclusion chromatography and sterile filtered. Protein concentrations and payload to antibody ratios were determined by UV spectral analysis according to Hamblett et al (American Association for Cancer Research. 2004 Oct. 15:10(20):7063-70) or mass difference, native versus conjugated. Size-exclusion HPLC established that all conjugates used were >95% monomeric, and RP-HPLC established that there was <0.5% unconjugated linker payload. Yields and payload to antibody ratios are reported in Table 1.

Method B: The antibodies (10-20 mg/ml) in 50 mM HEPES, 150 mM NaCl, pH 8.0, and 10-15% (v/v) DMA were conjugated with a 5-6 fold excess of 10, 14, 20, 22, or 26 for 2 hours (hrs) at ambient temperature. The conjugate was purified by size exclusion chromatography or extensive ultrafiltration and sterile filtered. Protein concentrations were determined by UV spectral analysis. Size-exclusion HPLC established that all conjugates used were >90% monomeric, and RP-HPLC established that there was <1% unconjugated linker payload. All conjugated antibodies were analyzed by mass difference, native versus conjugated. Payload to antibody ratios are reported in Table 1.

Method C—Bacterial Transglutaminase Conjugation: Aglycosylated, deglycosylated, or glutamine tagged antibodies can be conjugated at 1-10 mg/mL in PBS pH 7.4. Linker payload 22 can be added in a 10 to 25-fold molar excess over antibody and the enzymatic reaction can be initiated by addition of 1-5 units of bacterial transglutaminase (Zedira, T1001) per mg antibody and incubated with shaking at 37° C. for 4-16 hours. The conjugates can be purified by size exclusion chromatography and sterile filtered. Protein and linker payload concentrations can be determined by UV spectral analysis. Size-exclusion HPLC can establish that conjugates can be >95% monomeric. All conjugated antibodies can be analyzed by UV for linker payload loading values according to Hamblett et al, Cancer Res 2004 10 7063. In addition, the conjugates can be analyzed by ESI-MS for linker payload loadings using a Waters Synapt G2-Si QTOF mass spectrometry coupled with Acquity UPLC. The chromatographic separation can be achieved on a C4 column (Waters protein BEH C4, 50 mm×1 mm, 1.7 μm) in a 25 minute gradient (minute: percentage of mobile phase B; 0:20%, 1:20%, 18:40%, 18.1:90, 20:95%, 20.8:95%, 20.9:20% 25:20%). The mobile phase A can be 0.1% formic acid in water and mobile phase B can be 0.1% formic acid in acetonitrile. The flow rate can be set at 100 μl/min. The detector TOF scan can be set from m/z 700-5000 for 25 minutes with major parameters as listed (Capillary voltage 3.2 kV; Sampling Cone 150; Source Offset at 80; Source temperatures 120° C.; Desolvation temperature 500° C.; Trap collision Energy 30; Transfer Collision Energy Off; Gas controls OFF; Resolving Quadrupole: LM resolution at 4.7). The combined spectra can be deconvoluted with MaxEnt function within MassLynx software.

Conjugates of Method A DAR Determination

To determine the loading of the linker-payloads on the antibody (cysteine conjugates), the conjugates were deglycosylated, reduced, and analyzed by LC-MS.

For the assay, 50 μg of the conjugate was diluted with mili-Q water to a final concentration of 1 mg/mL. Ten μL of PNGase F solution [PNGase F solution was prepared by adding 150 μL of PNGase F stock (New England Biolabs, Cat #P0704L) and 850 AL of mili-Q water and mixed well] was added to the diluted conjugate solution and then incubated at 37° C. overnight. 2.4 μL of 0.5 M TCEP was added to the sample such that the resulting material had a final TCEP concentration of 20 mM and this was then incubated at 50° C. for 30 minutes. Injections of 10 μL of each sample were made onto LC-MS (Waters Synat G2-Si) and eluted with 0.1 mL/minute of a gradient mobile phase 20-40% of mobile phase B over 25 minutes (Mobile Phase A: 0.1% v/v FA in H₂O; Mobile Phase B: 0.1% v/v FA in Acetonitrile). The LC separation was achieved on Waters Acquity BEH C18 column (1.0×50 mM, 1.7 μM).

The mass spectrometry spectra were deconvoluted and the identified light and heavy chain peaks represent the light chain (L) with linker-payload values=0 and 1, heavy chain (H) with linker-payload values=0, 1, 2, and 3. From the intensity values of each species, the drug to antibody ratio (DAR) was calculated using equation 1 below for a homo-dimer antibody conjugate.

$$DAR = 2 * \left[ \frac{L1}{L0 + L1} + \frac{H1 + 2*H2 + 3*H3}{H0 + H1 + H2 + H3} \right] \qquad \text{Equation 1}$$

Conjugates of Method B DAR Determination

To determine the loading of the linker-payloads on the antibody (lysine conjugates), the conjugates were deglycosylated, and analyzed by LC-MS.

For the assay, 50 μg of the conjugate was diluted with milli-Q water to a final concentration of 1 mg/mL. Ten μL of PNGase F solution [PNGase F solution was prepared by adding 150 μL of PNGase F stock (New England Biolabs, Cat #P0704L) and 850 μL of milli-Q water and mixed well] was added to the diluted conjugate solution and then incubated at 37° C. overnight. Injections of 5 μL of each sample were made onto LC-MS (Waters Synat G2-Si) and eluted with 0.1 mL/minute of a gradient mobile phase 20-50% of mobile phase B over 25 minutes (Mobile Phase A: 0.1% v/v FA in H₂O; Mobile Phase B: 0.1% v/v FA in Acetonitrile). The LC separation was achieved on a Waters Acquity BEH C4 column (1.0×50 mM, 1.7 μM) at 80° C.

Figure 18:
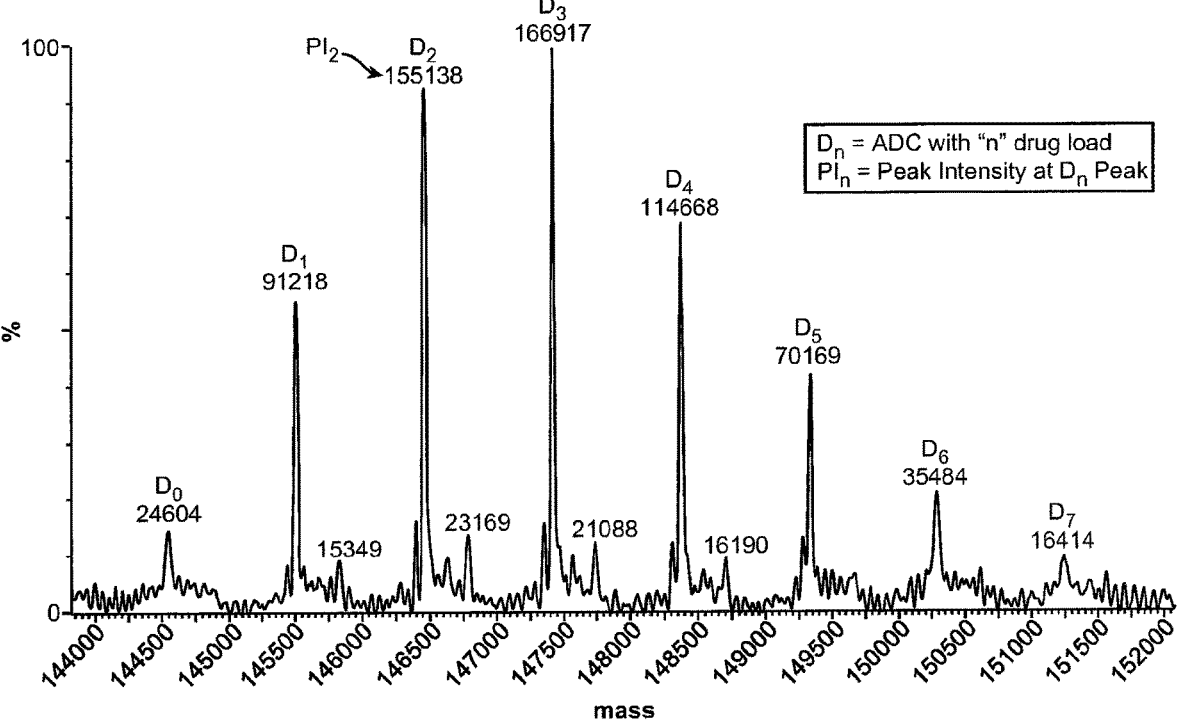
FIG. 18 shows the Deconvoluted Mass Spectrum of MCC-DM1 Conjugated mAb from Example 26.

The mass spectrometry spectra were deconvoluted using Masslynx software and the drug to antibody ratio (DAR) was calculated using the following equations. See FIG. 18.

1. Relative percentage (%) of drug (Dn) by distribution peak intensity (PI):
   a. Dn %=PIn/Σ(PI0+PI1+PI2 . . . +PIi)×100
   b. (n=0, 1, 2, 3, . . . , i)
2. Average DAR calculation:
   a. DAR=Σ(1×D1%+2×D2%+3×D3%+ . . . +i×Di %)

TABLE 1

| Antibody | ε252 nm (cm⁻¹ M⁻¹) | ε280 nm (cm⁻¹ M⁻¹) |
|---|---|---|
| PSMA | 77652 | 224320 |
| MUC16 | 85888 | 247360 |
| HER2 | 81847 | 215388 |
| STEAP2 | — | — |
| Isotype Control | 75113 | 218360 |

| Antibody Conjugate | Payload: Antibody (UV) | Yield % |
|---|---|---|
| PSMA-9 | 1.3 | 80 |
| MUC16-9 | 1.4 | 70 |
| HER2 | 1.5 | 75 |
| Isotype Control-9 | 1.5 | 80 |

| Antibody Conjugate | Payload: Antibody (ESI-MS) | Yield % |
|---|---|---|
| STEAP2-14 | 2.7 | 50 |
| STEAP2-20 | 1.2 | 45 |
| STEAP2-24 | 3.0 | 40 |
| HER2-10 | 2.3 | 60 |
| HER2-20 | 0.7 | 50 |
| HER2-24 | 3.3 | 40 |
| Isotype Control-10 | 2.4 | 75 |
| Isotype Control-14 | 1.3 | 70 |
| Isotype Control-20 | 1.0 | 50 |
| Isotype Control-24 | 3.6 | 40 |

387

Example 27

In Vitro Linker-Payload Cell-Free Enzymatic Assays

Cathepsin B Incubation

In vitro cell-free enzymatic assay procedure was adopted from Dubowchik, et al. Bioconjugate Chem. 2002 13 855, the entire contents of which are herein incorporated by reference in its entirety for all purposes. The linker payload 9 was set at 100 µg/mL final in 25 mM sodium acetate buffer, 1 mM EDTA, pH 5.0 and pre-incubated at 37° C. Cathepsin B (Sigma #C8571) was activated at room temperature for 15 minutes with 1 equivalent of 30 mM DTT, 15 mM EDTA to 2 equivalents of cathepsin B stock. The activated cathepsin B solution was added to the substrate solutions at a 1:20 molar ratio (purified $H_2O$, instead of activated cathepsin B was added for the control sample.) Samples were incubated at 37° C. overnight and the resulting samples are detected by LC-MS through Q1 Scan.

LC-MS Detection

Samples are centrifuged at 12,000 g for 5 min. Supernatant was recovered and analyzed by liquid chromatography-mass spectrometry (Waters Xevo TQ-S) by combined infusion of 0.3 ml/min of 30:70 mobile phase B:A (Mobile Phase A: 0.1% FA in $H_2O$; Mobile Phase B: 0.1% FA in Acetonitrile) at 20 µl/min from supernatant. MS1 is set at an appropriate range for detection of molecular ion of either linker payload or payload. The supernatant contained the predicted payload, Maytan-3-O-carbamoyl-N-(4-aminobenzene) (8), with a mass of 720.9 (M+Na) (calc'd monoisotopic mass for $C_{35}H_{43}N_4O_9Cl$, 698.3) and the control samples without cathepsin B contained 9 with a mass of 1170.4 (M+Na) (calc'd monoisotopic mass for $C_{60}H_{80}ClN_9O_{16}$, 1147.50). No predicted payload molecular ion was detected in the control samples.

The results of this Example are significant in part because cathepsin B proteolysis of 9 should only occur after internalization of the ADC in the cell where the enzyme exists. Off target effects should be reduced since the antibody delivers the cytotoxic payload directly to targeted cells.

Example 28

In Vitro Cytotoxicity Assays

In this Example, the ability of various antibody-drug conjugates and naked payloads to kill antigen-expressing tumor cells in vitro was assessed.

Ovcar3 (Muc16+) cells were seeded in 96 well plates at 3000 cells per well in complete growth media and grown overnight. For cell viability curves, serially diluted conjugates or naked payloads were added to the cells at final concentrations ranging from 100 nM to 5 pM and incubated for 3 days. To measure viability, cells were incubated with CCK8 (Dojindo) for the final 2 hours and the absorbance at 450 nm ($OD_{450}$) was determined on a Victor (Perkin Elmer). Background $OD_{450}$ levels determined from digitonin (40 nM) treated cells were subtracted from all wells and viability is expressed as a percentage of the untreated controls. $IC_{50}$ values were determined from a four-parameter logistic equation over a 10-point response curve (GraphPad Prism). The $IC_{50}$ for the MUC16-9 ADC was +++ which indicates an $IC_{50}$ (nM) greater than, or equal to, 0.1 and less than 1.0. All curves and $IC_{50}$ values are corrected for payload equivalents. The plot of % Cell Viability vs. Log 10 [M] Drug is shown in FIG. 1. Naked payload $IC_{50}$ values and percent cell kill are listed in Table 2.

SKBR3 (Her2+) cells were seeded in 96 well plates at 8000 cells per well in complete growth media and grown overnight. For cell viability curves, serially diluted conjugates or naked payloads were added to the cells at final concentrations ranging from 100 nM to 5 pM and incubated for 3 days. To measure viability, cells were incubated with CCK8 (Dojindo) for the final 2 hours and the absorbance at 450 nm ($OD_{450}$) was determined on a Victor (Perkin Elmer). Background $OD_{450}$ levels determined from digitonin (40 nM) treated cells were subtracted from all wells and viability is expressed as a percentage of the untreated controls. $IC_{50}$ values were determined from a four-parameter logistic equation over a 10-point response curve (GraphPad Prism). The $IC_{50}$ for the HER2-9, 10, 20, and 24 ADCs was +++, +++, +++, and +++, respectively, wherein +++ indicates $IC_{50}$ (nM) greater than, or equal to, 0.1 and less than 1.0. All curves and $IC_{50}$ values are corrected for payload equivalents. The plot of % Cell Viability vs. Log 10 [M] Drug is shown in FIGS. 2-5. Naked payload $IC_{50}$ values and percent cell kill are listed in Table 2.

C4-2 (STEAP2+) cells were seeded in 96 well plates at 4000 cells per well in complete growth media and grown overnight. For cell viability curves, serially diluted conjugates or naked payloads were added to the cells at final concentrations ranging from 100 nM to 5 pM and incubated for 5 days. To measure viability, cells were incubated with CellTiter-Glo reagents for 5 minutes and luminescence was determined on a Victor plate reader (PerkinElmer). $IC_{50}$ values were determined from a four-parameter logistic equation over a 10-point response curve (GraphPad Prism). The $IC_{50}$ for the STEAP2-14, 20, and 24 ADCs were ++, +++, +nM, respectively. +++ indicates $IC_{50}$ (nM) greater than, or equal to, 0.1 and less than 1.0; ++ indicates $IC_{50}$ (nM) greater than, or equal to, 1.0 and less than 10; and + indicates $IC_{50}$ (nM) greater than, or equal to, 10.

Figure 6:
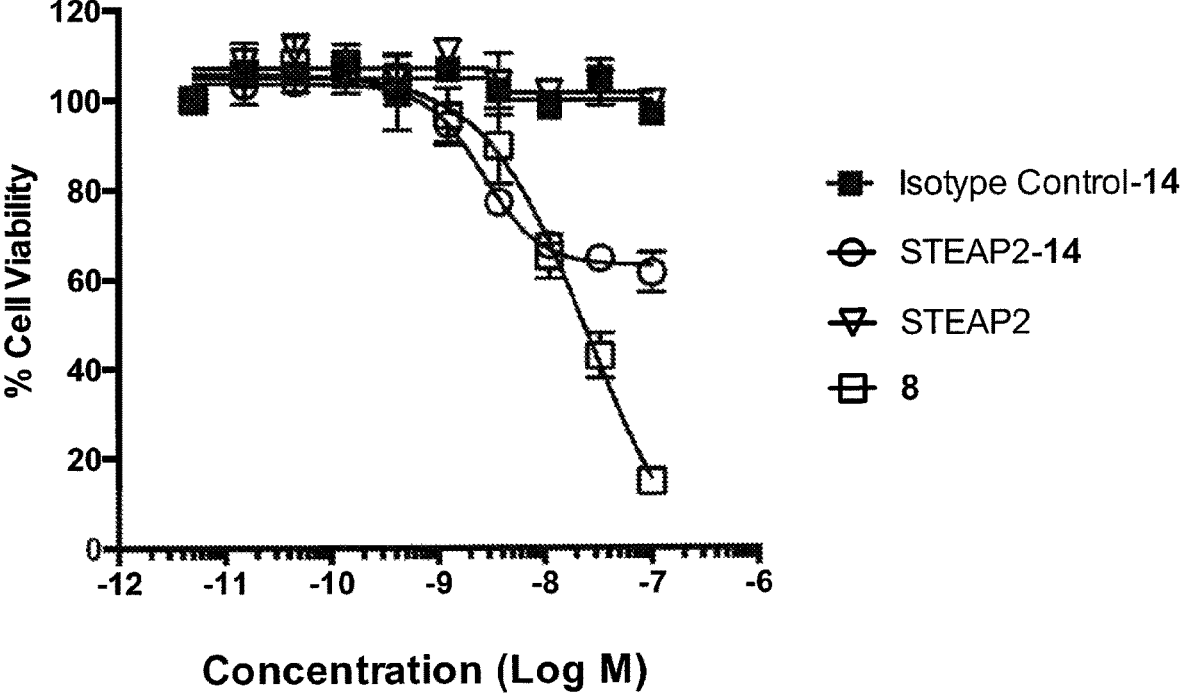
FIG. 6 depicts the plot of % Cell Viability C4-2 vs. $Log_{10}$ [M] of certain compounds tested in Example 28.
Figure 7:
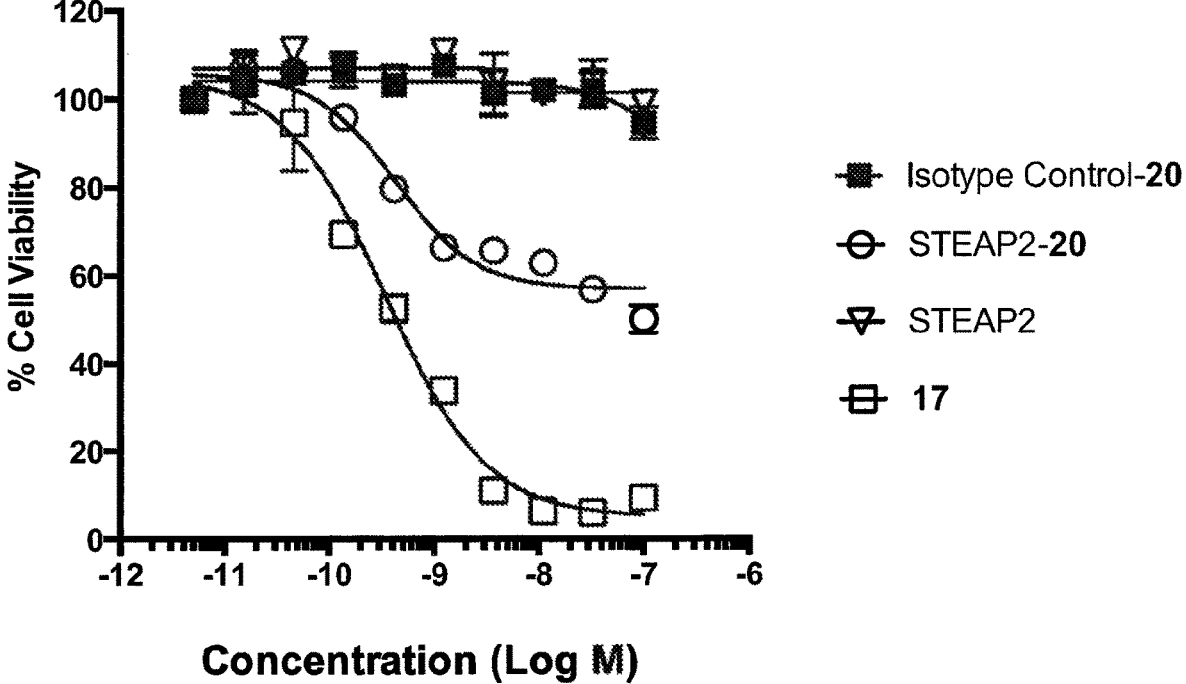
FIG. 7 depicts the plot of % Cell Viability C4-2 vs. $Log_{10}$ [M] of certain compounds tested in Example 28.
Figure 8:
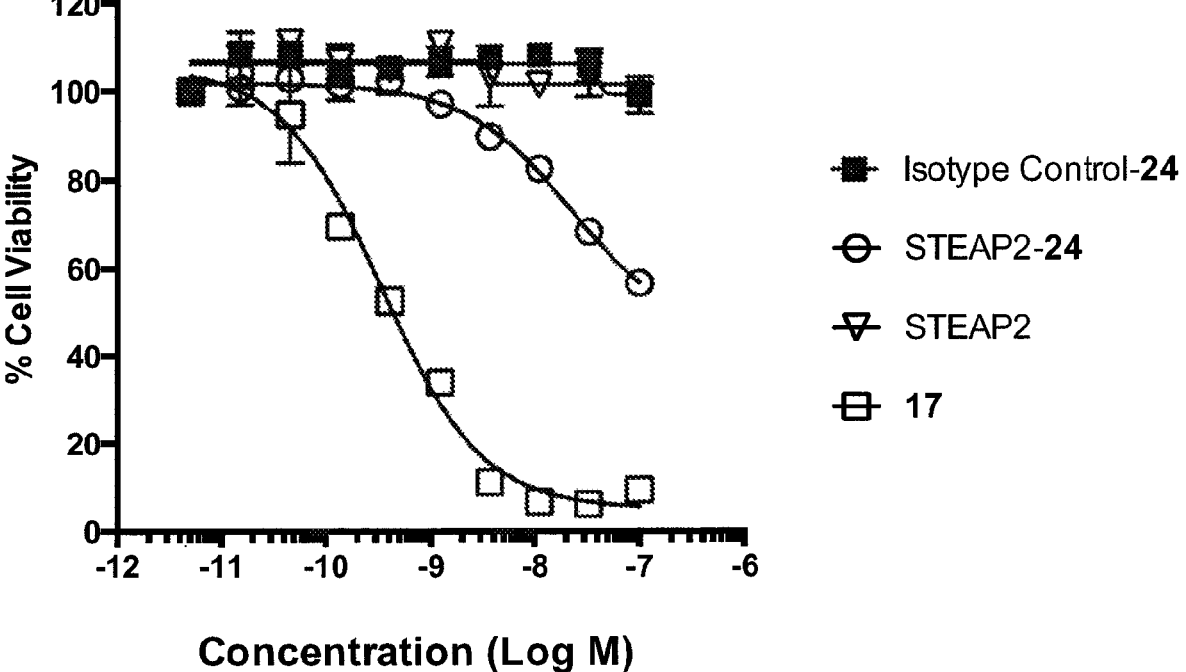
FIG. 8 depicts the plot of % Cell Viability C4-2 vs. $Log_{10}$ [M] of certain compounds tested in Example 28.

All $IC_{50}$s are expressed in nM concentration and % kill is reported for the highest dose. All curves and $IC_{50}$ values are corrected for payload equivalents. The plot of % Cell Viability vs. Log 10 [M] Drug is shown in FIGS. 6-8. Naked payload $IC_{50}$ values and percent cell kill are listed in Table 2.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

TABLE 2

| Compound # | Ovcar3 IC50 (nM) | Ovcar3 % kill | C4-2 IC50 (nM) | C4-2 % kill | SKBr-3 IC50 (nM) | SKBr-3 % kill |
|---|---|---|---|---|---|---|
| 8 | ++ | ** | + | **** | ++ | **** |
| 17 | +++++ | *** | +++ | **** | ++++ | ***** |
| 30a | +++ | *** | ++ | ***** | +++ | **** |
| 30b | | | + | * | +++ | **** |
| 30c | ++ | ** | + | ** | ++ | *** |
| 30d | | | ++ | **** | ++ | **** |
| 30e | | | ++ | **** | ++ | *** |
| 30f | | | ++ | **** | +++ | ***** |
| 30g | | | ++ | ***** | +++ | ***** |
| 30h | | | ++ | * | +++ | **** |

TABLE 2-continued

| Compound # | Ovcar3 | | C4-2 | | SKBr-3 | |
|---|---|---|---|---|---|---|
| | IC50 (nM) | % kill | IC50 (nM) | % kill | IC50 (nM) | % kill |
| 30i | | | + | ***** | ++ | ***** |
| 30j | ++ | ** | + | *** | +++ | **** |
| 30k | +++ | *** | + | | ++ | ***** |
| 30l | +++ | *** | + | | +++ | ***** |
| 30m | +++++ | ** | ++++ | ***** | ++++ | ***** |
| 30n | | | + | ***** | ++ | ***** |
| 30o | | | + | * | +++ | ***** |
| 30p | | | + | | + | * |
| 30q | | | + | *** | ++ | ***** |

+++++ indicates IC$_{50}$ (nM) greater than, or equal to, 0.001 and less than 0.01;

++++ indicates IC$_{50}$ (nM) greater than, or equal to, 0.01 and less than 0.1;

+++ indicates IC$_{50}$ (nM) greater than, or equal to, 0.1 and less than 1.0;

++ indicates IC$_{50}$ (nM) greater than, or equal to, 1.0 and less than 10; and + indicates IC$_{50}$ (nM) greater than, or equal to, 10.

***** indicates % kill greater than, or equal to, 99;

**** indicates % kill greater than, or equal to, 95 and less than 99;

*** indicates % kill greater than, or equal to, 90 and less than 95;

** indicates % kill greater than, or equal to, 85 and less than 90; and

* indicates % kill less than 85.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A compound of Formula I (I)

or a pharmaceutically acceptable salt or stereoisomer thereof, wherein:

A is arylene or heteroarylene;

L is a linker;

BA is a binding agent; and k is an integer from one to ten.

2. A compound of Formula II (II)

or a pharmaceutically acceptable salt or stereoisomer thereof, in A is a divalent radical of benzene, pyridine, naphthalene, or quinolone.

3. A compound of Formula P1

(P1)

wherein A is a divalent radical of benzene, pyridine, naphthalene, or quinolone; and RL is a reactive linker.

4. A compound of Formula PPII (PPII)

wherein A is a divalent radical of benzene, naphthalene, or quinolone.

5. The compound of claim 4, wherein

A is

R$^1$, independently at each occurrence, is selected from alkyl, alkenyl, alkynyl, alkoxy, aryl, alkaryl, arylalkyl, halo, haloalkyl, haloalkoxy, heteroalkyl, heteroaryl, heterocycloalkyl, cyano, nitro, and azido;

R$^A$ is alkyl;

n is an integer from zero to four.

6. The compound of claim 5, wherein R$^1$, independently at each occurrence, is selected from alkyl, alkoxy, halo, haloalkyl, and heterocycloalkyl.

7. The compound of claim 4, wherein the compound of Formula PPII is a compound of Formula PP5A1

(PP5A1)

wherein

R$^1$, independently at each occurrence, is selected from alkyl, alkoxy, halo, haloalkyl, and heterocycloalkyl; and n is an integer from zero to four.

8. The compound of claim 4, wherein the compound is selected from

393

-continued

394

-continued

395

-continued

396

-continued

397

-continued

398

-continued

9. A method of preparing a compound of Formula I (I)

comprising contacting a compound of P1

(P1)

with a binding agent under conjugation conditions, wherein

A is a divalent radical of benzene, pyridine, naphthalene, or quinolone;

L is a linker;

BA is a binding agent;

k is an integer from one to ten; and

RL is a reactive linker.

10. The method of claim 9, wherein:

A is $(R^1)_n$ $R^1$, independently at each occurrence, is selected from alkyl, alkenyl, alkynyl, alkoxy, aryl, alkaryl, arylalkyl, halo, haloalkyl, haloalkoxy, heteroalkyl, heteroaryl, heterocycloalkyl, cyano, nitro, $-OR^A$, $-SO_2R^A$, $R^A$, and azido;

$R^A$ is alkyl; and n is an integer from zero to four.

11. The method of claim 10, wherein $R^1$, independently at each occurrence, is selected from alkyl, alkoxy, halo, haloalkyl, and heterocycloalkyl; and n is an integer from zero to four.

12. The method of claim 9, wherein the compound of Formula P1 is prepared by contacting a compound of Formula II Formula (II)

with a RL,

RL is a reactive linker; and the compound of Formula II is prepared by contacting a compound of Formula PP5A with a suitable reducing agent (PP5A)

wherein $R^1$, independently at each occurrence, is selected from alkyl, alkenyl, alkynyl, alkoxy, aryl, alkaryl, arylalkyl, halo, haloalkyl, haloalkoxy, heteroalkyl, heteroaryl, heterocycloalkyl, cyano, nitro, $-OR^A$, $-SO_2R^A$, $R^A$, and azido;

$R^A$ is alkyl;

n is an integer from zero to four; and the suitable reducing agent is selected from a metal, a metal foil, a metal powder, dust of a metal, a metal amalgam, or metal filings.

13. A method of making a compound of Formula II (II)

wherein

A is a divalent radical of benzene, pyridine, naphthalene, or quinolone comprising:

(a) contacting a compound of Formula P2

P2 with a compound of Formula PP6

PP6 under Lewis acid synthesis conditions to form a compound of Formula PPII (PPII)

and (b) reducing the compound of Formula PPII by contacting the compound of Formula PPII with a reducing agent to form the compound of Formula II.

14. The method of claim 13 wherein

A is $R^1$, independently at each occurrence, is selected from alkyl, alkenyl, alkynyl, alkoxy, aryl, alkaryl, arylalkyl, halo, haloalkyl, haloalkoxy, heteroalkyl, heteroaryl, heterocycloalkyl, cyano, nitro, and azido;

$R^4$ is alkyl;

n is an integer from zero to four.

15. The method of claim 13, wherein $R^1$, independently at each occurrence, is selected from alkyl, alkoxy, halo, haloalkyl, and heterocycloalkyl.

16. A method of making a compound of Formula PPII, comprising contacting a compound of Formula P2 with a compound of Formula PP6 under Lewis acid synthesis conditions (PPII)

P2

-continued

PP6

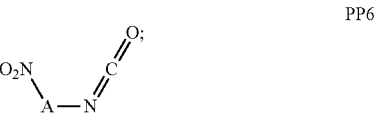

wherein A is a divalent radical of benzene, naphthalene, or quinolone.

17. The method of claim 16, wherein A is

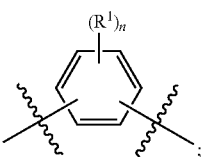

$R^1$, independently at each occurrence, is selected from alkyl, alkenyl, alkynyl, alkoxy, aryl, alkaryl, arylalkyl, halo, haloalkyl, haloalkoxy, heteroalkyl, heteroaryl, heterocycloalkyl, cyano, nitro, $$\begin{array}{ccc} \text{---}OR^A, & \text{---}SO_2R^A, & \text{---}\overset{O}{\overset{\|}{C}}R^A, \end{array}$$

and azido;

$R^A$ is alkyl;

n is an integer from zero to four.

18. The method of claim 16, wherein $R^1$, independently at each occurrence, is selected from alkyl, alkoxy, halo, haloalkyl, and heterocycloalkyl.

\* \* \* \* \*